(12) United States Patent
Rosentreter et al.

(10) Patent No.: US 7,135,486 B1
(45) Date of Patent: Nov. 14, 2006

(54) SUBSTITUTED 2-THIO-3,5-DICYANO-4-ARYL-6-AMINOPYRIDINES AND THE USE THEREOF

(75) Inventors: Ulrich Rosentreter, Wuppertal (DE); Rolf Henning, Wuppertal (DE); Marcus Bauser, Wuppertal (DE); Thomas Krämer, Wuppertal (DE); Andrea Vaupel, Riehen (CH); Walter Hübsch, Wuppertal (DE); Klaus Dembowsky, Boston, MA (US); Olga Salcher-Schraufstätter, Wuppertal (DE); Johannes-Peter Stasch, Solingen (DE); Thomas Krahn, Hagen (DE); Elisabeth Perzborn, Wuppertal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 280 days.

(21) Appl. No.: 10/110,284

(22) PCT Filed: Sep. 19, 2000

(86) PCT No.: PCT/EP00/09153

§ 371 (c)(1),
(2), (4) Date: Aug. 19, 2002

(87) PCT Pub. No.: WO01/25210

PCT Pub. Date: Apr. 12, 2001

(30) Foreign Application Priority Data

Oct. 1, 1999 (DE) .............................. 199 47 154

(51) Int. Cl.
*C07D 213/85* (2006.01)
*A61K 31/44* (2006.01)

(52) U.S. Cl. .................................. 514/344; 546/287
(58) Field of Classification Search ................ 514/344; 546/287
See application file for complete search history.

(56) References Cited

U.S. PATENT DOCUMENTS 5,227,485 A 7/1993 Quinn et al. ................ 544/262

FOREIGN PATENT DOCUMENTS

WO 9921617 6/1999

OTHER PUBLICATIONS

Dyachenko et al. Russian Journal of Organic Chemistry, vol. 34, No. 4, pp. 557-563, 1998.*
Chem. Abstr. *126*:23, Krivokolyko, S., Dyachenko, V., "Esters and Nitriles of 3-Phenylacrylic and 3-(2-furyl) Acrylic Acid in Synthesis of 6-Amino-3, 5-Dicyano-4-Phenyl (or 2-furyl) Pyridine-2 (1H) —Thiones and Selenones" (1997).

Chem Abstr. XP-002155853, Dyachenko, V., Litvinov, V., "Synthesis and Recyclization of 4-Aryl-2, 6-Diamino-3, 5-Dicyano-4H-Thiopyrans", Russian J. Org. Chem., 34: 557-563 (1998).
Chem Abstr. XP-002155854, Dyachenko, V., Litvinov, V., "Synthesis and Recyclization of 4-Aryl-2, 6-Diamino-3, 5-Dicyano-4H-Thiopyrans", Russian J. Org. Chem., 34: 557-563 (1998).
Chem Abstr. XP-002155855, Dyachenko, V., Litvinov, V., "Synthesis and Recyclization of 4-Aryl-2, 6-Diamino-3, 5-Dicyano-4H-Thiopyrans". Russian J. Org. Chem., 34: 557-563 (1998).
Chem Abstr. XP-002155856, Dyachenko, V., Litvinov, V., "Synthesis and Recyclization of 4-Aryl-2, 6-Diamino-3, 5-Dicyano-4H-Thiopyrans", Russian J. Org. Chem., 34: 557-563 (1998).
Chem Abstr. XP-002155857, Dyachenko, V., Litvinov, V., "Michael Reaction in Synthesis of 6-Amino-4-(4-Butoxyphenyl)-3,5-Dicyanopyridine-2(1H)-Thione" (1998).
Chem Abstr. XP-002155858, Dyachenko, V., Litvinov, V., "Michael Reaction in Synthesis of 6-Amino-4-(4-Butoxyphenyl)-3,5-Dicyanopyridine-2(1H)-Thione", Chem. Of Heterocyclic Compounds, 34: 188-194 (1998).
Chem Abstr. XP-002155859, Dyachenko, V., Litvinov, V., "Michael Reaction in Synthesis of 6-Amino-4-(4-Butoxyphenyl)-3,5-Dicyanopyridine-2(1H)-Thione", Chem. Of Heterocyclic Compounds, 34: 188-194 (1998).
Chem Abstr. XP-002155860, Dyachenko, V., Krivokolysko, S., Sharanin, Y., Litvinov, V., "New Method for the Synthesis of 6-Amino-4-Aryl-3, 5-Dicyano-3, 4-Dihydropyridine-2(1H)-Thiones by Recyclization of 4-Aryl-2, 6-Diamino-4H-Thiopyranes", Chem. Of Heterocyclic Compounds, 33: 793-798 (1997).
Chem Abstr. XP-002155861, Sharanin, Y., Krivokolysko, S., Dyachenko, V., "Cyclization Reactions of Nitriles Liv.* Synthesis and Properties of 6-Amino-4-Aryl-3, 5-Dicyanopyridin-2(1H)-Ones, The Corresponding Thiones, The Pyridylidenemalononitriles, and Their Hydrogenated Analogs", J. Org. Chem., 30: 620-626 (1994).

(Continued)

*Primary Examiner*—Zinna Northington Davis

(57) ABSTRACT

This application relates to compounds of formula (I),

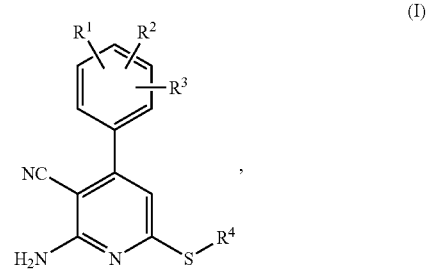

(I)

wherein $R^1$, $R^2$, $R^3$, and $R^4$ are defined as recited in the claims, or a tautomer, salt, hydrate, or alkoxide thereof. A process for preparing such materials, pharmaceutical compositions containing them, and methods of treating a cardiovascular disorder by administering them to a patient are also disclosed and claimed.

17 Claims, No Drawings

OTHER PUBLICATIONS

Chem Abstr. XP-002155862, Sharanin, Y., Krivokolysko, S., Dyachenko, V., "Cyclization Reactions of Nitriles Liv.* Synthesis and Properties of 6-Amino-4-Aryl-3, 5-Dicyanopyridin-2(1H)-Ones, The Corresponding Thiones, The Pyridylidenemalononitriles, and Their Hydrogenated Analogs", J. Org. Chem., 30: 620-626 (1994).

Chem Abstr. XP-002155863, Sharanin, Y., Krivokolysko, S., Dyachenko, V., "Cyclization Reactions of Nitriles Liv.* Synthesis and Properties of 6-Amino-4-Aryl-3, 5-Dicyanopyridin-2(1H)-Ones, The Corresponding Thiones, The Pyridylidenemalononitriles, and Their Hydrogenated Analogs", J. Org. Chem., 30: 620-626 (1994).

Chem Abstr. XP-002155864, Sharanin, Y., Krivokolysko, S., Dyachenko, V., "Cyclization Reactions of Nitriles Liv.* Synthesis and Properties of 6-Amino-4-Aryl-3, 5-Dicyanopyridin-2(1H)-Ones, The Corresponding Thiones, The Pyridylidenemalononitriles, and Their Hydrogenated Analogs", J. Org. Chem., 30: 620-626 (1994).

Chem Abstr. XP-002155865, Sharanin, Y., Krivokolysko, S., Dyachenko, V., "Cyclization Reactions of Nitriles Liv.* Synthesis and Properties of 6-Amino-4-Aryl-3, 5-Dicyanopyridin-2(1H)-Ones, The Corresponding Thiones, The Pyridylidenemalononitriles, and Their Hydrogenated Analogs", J. Org. Chem., 30: 620-626 (1994).

Chem Abstr. XP-002155866, Sharanin, Y., Krivokolysko, S., Dyachenko, V., "Cyclization Reactions of Nitriles Liv.* Synthesis and Properties of 6-Amino-4-Aryl-3, 5-Dicyanopyridin-2(1H)-Ones, The Corresponding Thiones, The Pyridylidenemalononitriles, and Their Hydrogenated Analogs", J. Org. Chem., 30: 620-626 (1994).

Chem Abstr. XP-002038897, Jacobson, K., van Galen, P., Williams, M., "Adenosine Receptors: Pharmacology, Structure-Activity Relationships, and Therapeutic Potential", J. Med. Chem., 35: 407-422 (1992).

Poulsen, S., Quinn, R., "Adenosine Receptors: New Opportunities for Future Drugs", Bioorganic & Medicinal Chem., 6: 619-641 (1998).

Olah, M., Ren, H., Ostrowski, J., Jacobson, K., Stiles, G., "Cloning, Expression, and Characterization of the Unique Bovine $A_1$ Adenosine Receptor", J. of Biol. Chem., 267: 10764-10770 (1992).

Klotz, K., Hessling, J., Hegler, J., Owman, C., Kull, B., Fredholm, B., Lohse, M., "Comparative Pharmacology of Human Adenosine Receptor Subtypes—Characterization of Stably Transfected Receptors in CHO Cells", Naunyn-Schmeideberg's Arch Pharmacol., 357: 1-9 (1998).

Dyachenko, V., Krivokolysko, S., Sharanin, Y., Litvinov, V., "New Route to 6-Amino-4-Aryl-3,5-Dicyano-Pyridine-2(1H)-Thiones", Russian J. Organic Chem., 33: 1014-1017 (1997).

* cited by examiner

SUBSTITUTED 2-THIO-3,5-DICYANO-4-ARYL-6-AMINOPYRIDINES AND THE USE THEREOF

The present invention relates to substituted 2-thio-3,5-dicyano-4-aryl-6-amino-pyridines, to a process for their preparation and to their use as active compounds for medicaments.

The present invention furthermore provides the use of adenosine-receptor-selective ligands for the prophylaxis and/or treatment of various disorders.

Adenosine, a nucleoside consisting of adenine and D-ribose, is an endogenous factor having cell-protective activity, in particular under cell-damaging conditions with limited oxygen and substrate supply, such as, for example, in the case of ischemia in various organs (for example heart and brain).

Adenosine is formed intracellularly as an intermediate during the degradation of adenosine 5'-monophosphate (AMP) and S-adenosylhomocysteine, but it can be released from the cell, in which case it acts as a hormone-like substance or neurotransmitter by binding to specific receptors.

Under normoxic conditions, the concentration of free adenosine in the extracellular space is very low. However, under ischemic or hypoxic conditions, the extracellular concentration of adenosine in the affected organs is increased dramatically. Thus, it is known, for example, that adenosine inhibits platelet degradation and increases the blood supply to the coronary vessels of the heart. Furthermore, it acts on the heart rate, on the release of neurotransmitters and on lymphocyte differentiation.

The aim of these actions of adenosine is to increase the oxygen supply of the affected organs and/or to reduce the metabolism of these organs in order to adjust the metabolism of the organ to the blood supply of the organ under ischemic or hypoxic conditions.

The action of adenosine is mediated via specific receptors. To date, subtypes A1, A2a, A2b and A3 are known. The actions of these adenosine receptors are mediated intracellularly by the messenger cAMP. In the case of the binding of adenosine to the A2a or A2b receptors, the intracellular cAMP is increased via activation of the membrane-bond adenylate cyclase, whereas binding of adenosine to A1 or A3 receptors results in a decrease of the intracellular cAMP concentration via inhibition of adenylate cyclase.

According to the invention, "Adenosine-receptor-selective ligands" are substances which bind selectively to one or more subtypes of the adenosine receptors, thus either mimicking the action of adenosine (adenosine agonists) or blocking its action (adenosine antagonists).

According to their receptor selectivity, adenosine-receptor-selective ligands can be divided into different categories, for example ligands which bind selectively to the A1 or A2 receptors of adenosine and in the case of the latter also, for example, those which bind selectively to the A2a or the A2b receptors of adenosine. Also possible are adenosine receptor ligands which bind selectively to a plurality of subtypes of the adenosine receptors, for example ligands which bind selectively to the A1 and the A2, but not to the A3 receptors of adenosine.

The abovementioned receptor selectivity can be determined by the effect of the substances on cell lines which, after stable transfection with the corresponding cDNA, express the receptor subtypes in question (see the publication M. E. Olah, H. Ren, J. Ostrowski, K. A. Jacobson, G. L. Stiles, "Cloning, expression, and characterization of the unique bovine A1 adenosine receptor. Studies on the ligand binding site by site-directed mutagenesis." in *J. Biol. Chem.* 267 (1992) pages 10764–10770, the disclosure of which is hereby fully incorporated by way of reference).

The effect of the substances on such cell lines can be monitored by biochemical measurement of the intracellular messenger cAMP (see the publication K. N. Klotz, J. Hessling, J. Hegler, C. Owman, B. Kull, B. B. Fredholm, M. J. Lohse, "Comparative pharmacology of human adenosine receptor subtypes—characterization of stably transfected receptors in CHO cells" in *Naunyn Schmiedebergs Arch. Pharmacol.* 357 (1998) pages 1–9, the disclosure of which is hereby fully incorporated by way of reference).

The "adenosine-receptor-specific" ligands known from the prior art are mainly derivatives based on natural adenosine (S.-A. Poulsen and R. J. Quinn, "Adenosine receptors: new opportunities for future drugs" in *Bioorganic and Medicinal Chemistry* 6 (1998) pages 619–641). However, most of the adenosine ligands known from the prior art have the disadvantage that their action is not really receptor-specific, that their activity is less than that of natural adenosine or that they have only very weak activity after oral administration. Thus, because of the disadvantages mentioned above, they are mainly only used for experimental purposes.

It is now an object of the following invention to find or provide compounds which have a wide therapeutic range and can serve as active compounds for the prophylaxis and/or treatment of various diseases.

In particular, it is an object of the present invention to find or provide substances which preferably act as adenosine-receptor-selective ligands and are suitable for the prophylaxis and/or treatment of various disorders, in particular disorders of the cardiovascular system (cardiovascular disorders) or inflammatory disorders, but additionally also disorders of the urogenital system, the respiratory tract, the central nervous system, the diabetes (in particular diabetes mellitus) and cancer.

It is a further object of the present invention to find or provide adenosine-receptor-selective ligands having a high specificity of action for the abovementioned purposes.

Accordingly, the present invention relates to compounds of the general formula (I)

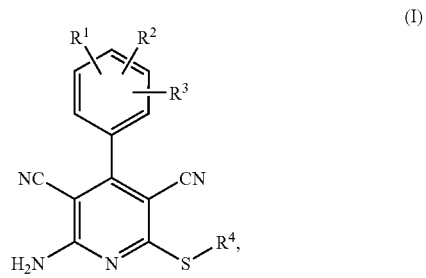

in which:
R$^1$, R$^2$, R$^3$ are identical or different and independently of one another are selected from the group of the following substituents:
  hydrogen;
  hydroxyl;
  optionally substituted (C$_1$–C$_8$)-alkyl;
  optionally substituted (C$_6$–C$_{10}$)-aryl;
  optionally substituted (C$_1$–C$_8$)-alkoxy;
  —O—(CH$_2$)$_n$—CH=CH$_2$ where n=0, 1 or 2;

halogen;
nitro;
cyano;
—C(O)—$R^5$;
—C(O)—$NR^6R^7$;
—$NR^6R^7$;
—$NR^6$—C(O)—$R^8$;
—O—C(O)—$R^8$;
—$SO_2$—$NR^6R^7$; and
—$NR^6$—$SO_2R^8$,
where:
$R^5$ denotes:
  hydrogen;
  hydroxyl;
  optionally substituted ($C_1$–$C_8$)-alkyl;
  optionally substituted ($C_3$–$C_7$)-cycloalkyl;
  optionally substituted ($C_1$–$C_8$)-alkoxy;
  optionally substituted ($C_6$–$C_{10}$)-aryl;
  optionally substituted ($C_6$–$C_{10}$)-aryloxy; or
  —O—$(CH_2)_n$—[($C_6$–$C_{10}$)-aryl] where n=1, 2 or 3,
    where the ($C_6$–$C_{10}$)-aryl group may be fused via two adjacent ring atoms to optionally substituted ($C_4$–$C_7$)-cycloalkyl,
or
$R^5$ represents a 5- to 7-membered saturated or unsaturated heterocycle which for its part may be mono- or polysubstituted by
  an oxo group (═O);
  halogen;
  optionally substituted ($C_1$–$C_8$)-alkyl;
  nitro;
  cyano;
  hydroxyl;
  optionally substituted ($C_6$–$C_{10}$)-aryl; or
  by ($C_1$–$C_8$)-alkoxy,
or
$R^5$ represents optionally substituted 5- to 6-membered heteroaryl having up to 3 heteroatoms from the group consisting of N, O and S,
  where the heterocycle and the heteroaryl ring may each optionally be fused via two adjacent ring atoms to optionally substituted ($C_6$–$C_{10}$)-aryl or optionally substituted ($C_4$–$C_7$)-cycloalkyl,
and
$R^6$ and $R^7$ are identical or different and represent
  hydrogen;
  optionally substituted ($C_1$–$C_8$)-alkyl;
  optionally substituted ($C_6$–$C_{10}$)-aryl; or
  represent optionally substituted 5- to 6-membered heteroaryl having up to 3 heteroatoms from the group consisting of N, O and S
or
$R^6$ and $R^7$ together with the nitrogen atom to which they are optionally attached form a 5- to 7-membered saturated or unsaturated heterocycle having up to 3 heteroatoms from the group consisting of N, O and S which for its part may optionally be mono- or polysubstituted by identical or different substituents from the group consisting of
  an oxo group (═O);
  halogen;
  ($C_1$–$C_8$)-alkyl;
  nitro;
  cyano;
  hydroxyl;
  ($C_6$–$C_{10}$)-aryl; or
  ($C_1$–$C_8$)-alkoxy,
and
$R^8$ represents hydroxyl;
  $NR^6R^7$ where $R^6$ and $R^7$ are as defined above;
  optionally substituted ($C_1$–$C_8$)-alkyl;
  ($C_1$–$C_8$)-alkoxy;
  optionally substituted ($C_6$–$C_{10}$)-aryl;
  ($C_6$–$C_{10}$)-aryloxy; or
  —O—$(CH_2)_n$—[($C_6$–$C_{10}$)-aryl] where n=1, 2 or 3,
and
$R^4$ represents straight-chain or branched ($C_1$–$C_8$)-alkyl or ($C_2$–$C_8$)-alkenyl which are optionally mono- or polysubstituted by
  hydroxyl;
  halogen;
  cyano;
  —C(O)—$R^5$ where $R^5$ is as defined above;
  —C(O)—$NR^6R^7$ where $R^6$ and $R^7$ are as defined above;
  —$NR^6R^7$ where $R^6$ and $R^7$ are as defined above;
  —$NR^6$C(O)—$R^8$ where $R^6$ and $R^8$ are as defined above;
  —$SO_2$—$NR^6R^7$ where $R^6$ and $R^7$ are as defined above;
  —$NR^6$—$SO_2$—$R^8$ where $R^6$ and $R^8$ are as defined above;
  —C(O)—$(CH_2)_n$—C(O)—$R^8$ where n=0 to 2 and $R^8$ is as defined above;
  ($C_1$–$C_8$)-alkoxy;
  optionally substituted ($C_6$–$C_{10}$)-aryloxy;
  optionally substituted 5- to 6-membered heteroaryl having up to 3 heteroatoms from the group consisting of N, O and S;
  optionally substituted ($C_6$–$C_{10}$)-aryl; or
  by a 5- to 7-membered saturated or unsaturated heterocycle having up to 3 heteroatoms from the group consisting of N, O and S which for its part may optionally be mono- or polysubstituted by identical or different substituents from the group consisting of an oxo group (═O); halogen; ($C_1$–$C_8$)-alkyl; nitro; cyano; hydroxyl; ($C_6$–$C_{10}$)-aryl; or by ($C_1$–$C_8$)-alkoxy,
  where the heterocycle and the heteroaryl ring may each optionally be fused via two adjacent ring atoms to optionally substituted ($C_6$–$C_{10}$)-aryl,
or
$R^4$ represents a 5- to 7-membered saturated or unsaturated heterocycle having up to 3 heteroatoms from the group consisting of N, O and S, which for its part may optionally be mono- or polysubstituted by identical or different substituents from the group consisting of an oxo group (═O); halogen; ($C_1$–$C_8$)-alkyl; nitro; cyano; hydroxyl; ($C_6$–$C_{10}$)-aryl; or by ($C_1$–$C_8$)-alkoxy, and which may optionally be fused via two adjacent ring atoms to optionally substituted ($C_6$–$C_{10}$)-aryl or optionally substituted ($C_4$–$C_7$)-cycloalkyl,
and their tautomers and their respective salts, hydrates and alkoxides,
except for the following compounds of the general formula (I), in which the radicals $R^1$, $R^2$, $R^3$ and $R^4$ are as defined below:
  $R^1$═$R^2$═H; $R^3$═para-OH; $R^4$═—$CH_2$—Z where Z═CN, C(O)—$OC_2H_5$, 4-Br—$C_6H_4$—CO, 4-n-butyl-$C_6H_4$—CO, H, $C_6H_5$, C(O)—O—$CH_2$—$C_6H_5$, C(O)—$OCH_3$, C(O)—OH, 2-oxo-benzo-pyranyl-3-carbonyl, 4-Cl—$C_6H_4$—CO, 3-Br—$C_6H_4$—CO, 4-$C_6H_5$—$C_6H_4$—CO, 4-$CH_3$—$C_6H_4$—CO, 3,4-$Cl_2$—$C_6H_3$—CO;
  $R^1$═$R^2$═H; $R^3$═meta-OH; $R^4$═—$CH_2$—Z where Z═4-Br—$C_6H_4$—NH—CO, 2-oxo-benzo-pyranyl-3-carbonyl, 4-Cl—$C_6H_4$—CO;

$R^1=R^2=H$; $R^3=$para-O—C(O)—CH$_3$; $R^4=$—CH$_2$—Z where Z=4-CH$_3$—C$_6$H$_4$—CO, H, 2-oxo-benzopyranyl-3-carbonyl, (CH$_2$)$_3$—CH$_3$, 4-C$_6$H$_5$—C$_6$H$_4$;

$R^1=R^2=R^3=H$; $R^4=$—CH$_2$—Z where Z=CH$_3$, CN, 2-naphthyl;

$R^1=R^2=H$; $R^3=$para-butoxy; $R^4=$—CH$_2$—Z where Z=4-Cl—C$_6$H$_5$, C(O)—OCH$_3$, C(O)—C$_6$H$_5$, CH=CH$_2$, C(O)—NH$_2$, H, 4-Br—C$_6$H$_4$—CO, 4-Cl—C$_6$H$_4$—CO, C(O)—OC$_2$H$_5$, C(O)—O—CH$_2$—C$_6$H$_5$, 2-oxo-benzopyranyl-3-carbonyl, C(O)—NH—C$_6$H$_5$, CN;

$R^1=R^2=H$; $R^3=$para-bromo; $R^4=$—CH$_2$—Z where Z=4-Br—C$_6$H$_4$—CO, 4-Cl—C$_6$H$_4$—CO, C(O)—NH$_2$, C(O)—OCH$_3$, 4-Cl—C$_6$H$_5$, 4-Br—C$_6$H$_4$—NH—CO;

$R^1=R^2=H$; $R^3=$meta-fluoro; $R^4=$—CH$_2$—Z where Z=4-Br—C$_6$H$_4$—CO, C(O)—NH$_2$, C(O)—O—CH$_2$—C$_6$H$_5$, CN;

$R^1=R^2=H$; $R^3=$para-chloro; $R^4=$—CH$_2$—Z where Z=2-naphthyl, CH$_3$;

$R^1=R^2=H$; $R^3=$para-OCH$_3$; $R^4=$—CH$_2$—Z where Z=2-naphthyl, CH$_3$;

$R^1=R^2=H$; $R^3=$meta-NO$_2$; $R^4=$—CH$_2$—Z where Z=CH$_3$.

Some of the abovementioned substances which can be used in accordance with the present invention for the prophylaxis and/or treatment of disorders are novel, and some are also known from the literature (see Dyachenko et al., Russian Journal of Chemistry, Vol. 33, No. 7, 1997, pages 1014–1017 and Vol. 34, No. 4, 1998, pages 557–563; Dyachenko et al., Chemistry of Heterocyclic Compounds, Vol. 34, 1998, pages 188–194; Elnagdi et al., Zeitschrift für Naturforschung, Vol. 47b, 1992, pages 572–578; Riguera et al., Eur. J. Med. Chem. 33, 1998, pages 887–897; *J. Vaquero, Thesis*, University of Alcala de Henares, Madrid, Spain, 1981). However, in the literature, a therapeutic use of the known compounds has hitherto not been described. The first time this has happened is in the context of the present invention.

Accordingly, the present invention also provides the use of the abovementioned compounds of the general formula (I), including the compounds excluded above, for the prophylaxis and/or treatment of disorders.

Depending on the substitution pattern, the compounds of the formula (I) can exist in stereoisomeric forms which are either like image and mirror image (enantiomers) or not like image and mirror image (diastereomers). The invention relates both to the enantiomers or diastereomers and to their respective mixtures. The racemic forms, like the diastereomers, can be separated in a known manner into the stereoisomerically uniform components. Likewise, the present invention also relates to the other tautomers of the compounds of the formula (I) and their salts.

Physiologically acceptable salts of the compounds of formula (I) can be salts of the substances according to the invention with mineral acids, carboxylic acids or sulfonic acids. Particular preference is given, for example, to salts with hydrochloric acid, hydrobromic acid, sulfuric acid, phosphoric acid, methanesulfonic acid, ethanesulfonic acid, toluenesulfonic acid, benzenesulfonic acid, naphthalene disulfonic acid, trifluoroacetic acid, acetic acid, propionic acid, lactic acid, tartaric acid, citric acid, fumaric acid, maleic acid or benzoic acid.

Salts which may be mentioned include salts with customary bases, such as, for example, alkali metal salts (for example sodium or potassium salts), alkaline earth metal salts (for example calcium or magnesium salts) or ammonium salts, derived from ammonia or organic amines such as, for example, diethylamine, triethylamine, ethyldiisopropylamine, procaine, dibenzylamine, N-methylmorpholine, dihydroabietylamine, 1-ephenamine or methylpiperidine.

Definitions in the Context of the Present Invention:

Halogen generally represents fluorine, chlorine, bromine or iodine. Preference is given to fluorine, chlorine or bromine. Very particular preference is given to fluorine or chlorine.

In the context of the present invention, (C$_1$–C$_8$)-alkyl, (C$_1$–C$_6$)-alkyl and (C$_1$–C$_4$)-alkyl represent a straight-chain or branched alkyl radical having 1 to 8; 1 to 6 and 1 to 4 carbon atoms, respectively. Examples which may be mentioned are: methyl, ethyl, n-propyl, isopropyl, n-butyl, isobutyl, tert-butyl, n-pentyl, isopentyl, n-hexyl, isohexyl, n-heptyl and n-octyl. Preference is given to a straight-chain or branched alkyl radical having 1 to 6 carbon atoms. Particular preference is given to a straight-chain or branched alkyl radical having 1 to 4 carbon atoms.

Optionally substituted (C$_1$–C$_8$)-alkyl, (C$_1$–C$_6$)-alkyl and (C$_1$–C$_4$)-alkyl, as used in the present invention, denotes an above-defined straight-chain or branched alkyl radical having 1 to 8; 1 to 6 and 1 to 4 carbon atoms, respectively, which for its part can be mono- or polysubstituted by identical or different substituents. Substituents which may be mentioned are in particular the following substituents: halogen (fluorine, chlorine, bromine, iodine); cyano; nitro; carboxyl; hydroxyl; straight-chain or branched (C$_1$–C$_8$)-alkoxy, preferably (C$_1$–C$_6$)-alkoxy, in particular (C$_1$–C$_4$)-alkoxy, where the alkoxy radical for its part may optionally be substituted; straight-chain or branched (C$_2$–C$_8$)-alkenyl, preferably (C$_2$–C$_6$)-alkenyl, in particular (C$_2$–C$_4$)-alkenyl, where the alkenyl radical for its part may optionally be substituted; (C$_6$–C$_{10}$)-aryl, in particular phenyl or naphthyl, where the (C$_6$–C$_{10}$)-aryl radical for its part may optionally be substituted; (C$_1$–C$_4$)-alkylsulfonyloxy, where the (C$_1$–C$_4$)-alkylsulfonyloxy radical for its part may optionally be substituted; phenylsulfonyl or p-tolylsulfonyl; straight-chain or branched (C$_1$–C$_8$)-thioalkyl, where the thioalkyl radical for its part may optionally be substituted; straight-chain or branched mono-, di- and/or trihalogeno-(C$_1$–C$_8$)-alkyl, in particular trifluoromethyl; straight-chain or branched mono-, di- and/or trihalogeno-(C$_1$–C$_8$)-alkoxy, in particular trifluoromethoxy; acyl; amino, N-[(C$_1$–C$_8$)-alkyl]-amino and/or N-di-[(C$_1$–C$_8$)-alkyl]-amino, where the alkyl radical for its part may optionally be substituted; and (C$_1$–C$_8$)-alkoxycarbonyl, where the alkoxycarbonyl radical for its part may optionally be substituted.

In the context of the present invention, (C$_6$–C$_{10}$)-aryl represents an aromatic radical having 6 to 10 carbon atoms. Preferred aryl radicals are phenyl and naphthyl.

In the context of the present invention, the term optionally substituted (C$_6$–C$_{10}$)-aryl represents an aromatic radical as defined above having 6 to 10 carbon atoms which for its part may be mono- or polysubstituted by identical or different substituents, in particular by: halogen (fluorine, chlorine, bromine, iodine); cyano; nitro; carboxyl; hydroxyl; straight-chain or branched (C$_1$–C$_8$)-alkyl, preferably (C$_1$–C$_6$)-alkyl, in particular (C$_1$–C$_4$)-alkyl, where the alkyl radical for its part may optionally be substituted; straight-chain or branched (C$_1$–C$_8$)-alkoxy, preferably (C$_1$–C$_6$)-alkoxy, in particular (C$_1$–C$_4$)-alkoxy, where the alkoxy radical for its part may optionally be substituted; straight-chain or branched ($C_2$–$C_8$)-alkenyl, preferably ($C_2$–$C_6$)-alkenyl, in particular ($C_2$–$C_4$)-alkenyl, where the alkenyl radical for its part may optionally be substituted; straight-chain or branched ($C_1$–$C_8$)-thioalkyl, where the thioalkyl radical for its part may optionally be substituted; straight-chain or branched mono-, di- and/or trihalogeno-($C_1$–$C_8$)-alkyl, in particular trifluoromethyl; straight-chain or branched mono-, di- and/or trihalogeno-($C_1$–$C_8$)-alkoxy, in particular trifluoromethoxy; acyl; amino, N-[($C_1$–$C_8$)-alkyl]-amino and/or N-di-[($C_1$–$C_8$)-alkyl]-amino, where the alkyl radical for its part may optionally be substituted; N-[($C_1$–$C_6$)-alkoxy]-aldimino; ($C_1$–$C_8$)-alkoxycarbonyl, where the alkoxycarbonyl radical for its part may optionally be substituted; and ($C_6$–$C_{10}$)-aryl, in particular phenyl or naphthyl, where the ($C_6$–$C_{10}$)-aryl radical for its part may optionally be substituted.

($C_6$–$C_{10}$)-Aryloxy represents a group —O—($C_6$–$C_{10}$)-aryl, in particular a group —O-phenyl or —O-naphthyl, where otherwise reference may be made to the above definition of ($C_6$–$C_1$)-aryl.

Optionally substituted ($C_6$–$C_{10}$)-aryloxy denotes a group —O—($C_6$–$C_{10}$)-aryl as defined above where, with respect to the substituents of the ($C_6$–$C_{10}$)-aryl group, reference may be made to the above definition under optionally substituted ($C_6$–$C_{10}$)-aryl.

($C_1$–$C_8$)-Alkoxy, ($C_1$–$C_6$)-alkoxy and ($C_1$–$C_4$)-alkoxy, as used in the present invention and also in the definitions of ($C_1$–$C_8$)-alkoxycarbonyl represents a straight-chain or branched alkoxy radical having 1 to 8; 1 to 6 and 1 to 4 carbon atoms, respectively. Examples which may be mentioned are: methoxy, ethoxy, n-propoxy, isopropoxy, n-butoxy, isobutoxy, tert-butoxy, n-pentoxy, isopentoxy, n-hexoxy, isohexoxy, n-heptoxy and n-octoxy. Preference is given to a straight-chain or branched alkoxy radical having 1 to 6 carbon atoms. Particular preference is given to a straight-chain or branched alkoxy radical having 1 to 4 carbon atoms.

In the context of the present invention, optionally substituted ($C_1$–$C_8$)-alkoxy, ($C_1$–$C_6$)-alkoxy and ($C_1$–$C_4$)-alkoxy denotes a straight-chain or branched alkoxy radical as defined above having 1 to 8, 1 to 6 and 1 to 4 carbon atoms, respectively, which may optionally be mono- or polysubstituted by identical or different substituents, in particular by the following substituents: halogen (fluorine, chlorine, bromine, iodine); cyano; nitro; carboxyl; hydroxyl; straight-chain or branched ($C_2$–$C_8$)-alkenyl, preferably ($C_2$–$C_6$)-alkenyl, in particular ($C_2$–$C_4$)-alkenyl, where the alkenyl radical for its part may optionally be substituted; straight-chain or branched ($C_1$–$C_8$)-thioalkyl, where the thioalkyl radical for its part may optionally be substituted; straight-chain or branched mono-, di- and/or trihalogeno-($C_1$–$C_8$)-alkyl, in particular trifluoromethyl; straight-chain or branched mono-, di- and/or trihalogeno-($C_1$–$C_8$)-alkoxy, in particular trifluoromethoxy; acyl; amino, N-[($C_1$–$C_8$)-alkyl]-amino and/or N-di-[($C_1$–$C_8$)-alkyl]-amino, where the alkyl radical for its part may optionally be substituted; or ($C_1$–$C_8$)-alkoxycarbonyl, where the alkoxycarbonyl radical for its part may optionally be substituted.

In the context of the invention, ($C_3$–$C_7$)-Cycloalkyl generally represents a carbon ring having 3 to 7 carbon atoms, such as, for example, cyclopropyl, cyclobutyl, cyclopentyl, cyclohexyl or cycloheptyl.

In the context of the invention, optionally substituted ($C_3$–$C_7$)-cycloalkyl generally represents a ($C_3$–$C_7$)-cycloalkyl radical as defined above which may optionally be mono- or polysubstituted by identical or different substituents, in particular by a ($C_1$–$C_8$)-alkyl radical, preferably a ($C_1$–$C_6$)-alkyl radical, very particularly preferably a ($C_1$–$C_4$)-alkyl radical, which for its part may in turn be mono- or polysubstituted as defined above.

In the context of the invention, a 5- to 6-membered aromatic heterocycle having up to 3 heteroatoms from the group consisting of S, N and O generally represents a monocyclic heteroaromatic radical which is attached via a ring carbon atom of the heteroaromatic radical and, if appropriate, also via a ring nitrogen atom of the heteroaromatic radical. Examples which may be mentioned are: furanyl (for example furan-2-yl, furan-3-yl), pyrrolyl (for example pyrrol-1-yl, pyrrol-2-yl, pyrrol-3-yl), thienyl, thiazolyl, oxazolyl, imidazolyl, triazolyl, pyridyl, pyrimidyl, pyridazinyl. Preference is given to pyridyl, pyrimidyl, pyridazinyl, furanyl, imidazolyl and thiazolyl.

In the context of the invention, an optionally substituted 5- to 6-membered aromatic heterocycle having up to 3 heteroatoms from the group consisting of S, N and O generally represents a heterocycle as defined above which may be mono- or polysubstituted by identical or different substituents from the group consisting of nitro; amino; guanidino; aminocarbonyl; halogen, preferably chlorine or fluorine; ($C_1$–$C_6$)-alkyl, preferably ($C_1$–$C_4$)-alkyl, as defined above, which for its part may optionally be substituted; or by ($C_6$–$C_{10}$)-aryl as defined above which for its part may optionally be substituted.

Compounds which are preferred in the context of the invention are compounds of the general formula (I), in which:
$R^1$, $R^2$, $R^3$ are identical or different and independently of one another are selected from the group of the following substituents:
hydrogen;
hydroxyl;
optionally substituted ($C_1$–$C_6$)-alkyl;
optionally substituted phenyl or naphthyl;
optionally substituted ($C_1$–$C_6$)-alkoxy;
—O—$(CH_2)_n$—CH=$CH_2$ where n=1 or 2;
fluorine, chlorine, bromine;
nitro;
cyano;
—C(O)—$R^5$;
—C(O)—$NR^6R$;
—$NR^6R^7$;
—$NR^6$—C(O)—$R^8$;
—O—C(O)—$R^8$;
—$SO_2$—$NR^6R^7$; and
—$NR^6$—$SO_2R^8$,
where:
$R^5$ denotes:
hydrogen;
hydroxyl;
optionally substituted ($C_1$–$C_6$)-alkyl;
optionally substituted ($C_3$–$C_7$)-cycloalkyl;
optionally substituted ($C_1$–$C_6$)-alkoxy;
optionally substituted phenyl or naphthyl;
optionally substituted phenyloxy or naphthyloxy; or
—O—$(CH_2)_n$-phenyl where n=1, 2 or 3, where the phenyl or naphthyl group may be fused via two adjacent ring atoms to optionally substituted $(C_4$–$C_7)$-cycloalkyl, or $R^5$ represents a 5- to 7-membered saturated or unsaturated heterocycle which for its part may be mono- or polysubstituted by
an oxo group (=O);
fluorine, chlorine, bromine;
optionally substituted $(C_1$–$C_6)$-alkyl;
nitro;
cyano;
hydroxyl;
optionally substituted phenyl or naphthyl; or
by $(C_1$–$C_6)$-alkoxy, or $R^5$ represents optionally substituted 5- to 6-membered heteroaryl having up to 3 heteroatoms from the group consisting of N, O and S,
where the heterocycle and the heteroaryl ring may each optionally be fused via two adjacent ring atoms to optionally substituted phenyl or naphthyl or optionally substituted $(C_4$–$C_7)$-cycloalkyl, and $R^6$ and $R^7$ are identical or different and represent
hydrogen;
optionally substituted $(C_1$–$C_6)$-alkyl;
optionally substituted phenyl or naphthyl; or
represent optionally substituted 5- to 6-membered heteroaryl having up to 3 heteroatoms from the group consisting of N, O and S or $R^6$ and $R^7$ together with the nitrogen atom to which they are optionally attached form a 5- to 7-membered saturated or unsaturated heterocycle having up to 3 heteroatoms from the group consisting of N, O and S which for its part may optionally be mono- or polysubstituted by identical or different substituents from the group consisting of
an oxo group (=O);
fluorine, chlorine, bromine;
$(C_1$–$C_6)$-alkyl;
nitro;
cyano;
hydroxyl;
phenyl or naphthyl; or
$(C_1$–$C_6)$-alkoxy, and $R^8$ represents $NR^6R^7$ where $R^6$ and $R^7$ are as defined above;
optionally substituted $(C_1$–$C_6)$-alkyl;
$(C_1$–$C_6)$-alkoxy;
optionally substituted phenyl or naphthyl;
phenyloxy or naphthyloxy; or
—O—$(CH_2)_n$-phenyl where n=1, 2 or 3, and $R^4$ represents straight-chain or branched $(C_1$–$C_6)$-alkyl or $(C_2$–$C_6)$-alkenyl which are optionally mono- or polysubstituted by
hydroxyl;
fluoro, chloro, bromine;
cyano;
—C(O)—$R^5$ where $R^5$ is as defined above;
—C(O)—$NR^6R^7$ where $R^6$ and $R^7$ are as defined above;
—$NR^6R^7$ where $R^6$ and $R^7$ are as defined above;
—$NR^6$—C(O)—$R^8$ where $R^6$ and $R^7$ are as defined above;
—$SO_2$—$NR^6R^7$ where $R^6$ and $R^7$ are as defined above;
—$NR^6$—$SO_2$—$R^8$ where $R^6$ and $R^8$ are as defined above;
—C(O)—$(CH_2)_n$—C(O)—$R^8$ where n=0 to 2 and $R^8$ is as defined above;
$(C_1$–$C_6)$-alkoxy;
optionally substituted phenyloxy or naphthyloxy;
optionally substituted 5- to 6-membered heteroaryl having up to 3 heteroatoms from the group consisting of N, O and S;
optionally substituted phenyl or naphthyl; or
by a 5- to 7-membered saturated or unsaturated heterocycle having up to 3 heteroatoms from the group consisting of N, O and S, which for its part may optionally be mono- or polysubstituted by identical or different substituents from the group consisting of an oxo group (=O); fluorine, chlorine, bromine; $(C_1$–$C_6)$-alkyl; nitro; cyano; hydroxyl; phenyl or naphthyl; or by $(C_1$–$C_6)$-alkoxy,
where the heterocycle and the heteroaryl ring may each optionally be fused via two adjacent ring atoms to optionally substituted phenyl or naphthyl, or $R^4$ represents a 5- to 7-membered saturated or unsaturated heterocycle having up to 3 heteroatoms from the group consisting of N, O and S,
which for its part may optionally be mono- or polysubstituted by identical or different substituents from the group consisting of an oxo group (=O); fluorine, chlorine, bromine; $(C_1$–$C_6)$-alkyl; nitro; cyano; hydroxyl; phenyl or naphthyl; or by $(C_1$–$C_6)$-alkoxy and which may optionally be fused via two adjacent ring atoms to optionally substituted phenyl or naphthyl or optionally substituted $(C_4$–$C_7)$-cycloalkyl, and their tautomers and their respective salts, hydrates and alkoxides, except for the following compounds of the general formula (I), in which the radicals $R^1$, $R^2$, $R^3$ and $R^4$ are as defined below:

$R^1$=$R^2$=H; $R^3$=para-OH; $R^4$=—$CH_2$—Z where Z=CN, C(O)—$OC_2H_5$, 4-Br—$C_6H_4$—CO, 4-n-butyl-$C_6H_4$—CO, H, $C_6H_5$, C(O)—O—$CH_2$—$C_6H_5$, C(O)—$OCH_3$, C(O)—OH, 2-oxo-benzo-pyranyl-3-carbonyl, 4-Cl—$C_6H_4$—CO, 3-Br—$C_6H_4$—CO, 4-$C_6H_5$—$C_6H_4$—CO, 4-$CH_3$—$C_6H_4$—CO, 3,4-$Cl_2$—$C_6H_3$—CO;

$R^1$=$R^2$=H; $R^3$=meta-OH; $R^4$=—$CH_2$—Z where Z=4-Br—$C_6H_4$—NH—CO, 2-oxo-benzo-pyranyl-3-carbonyl, 4-Cl—$C_6H_4$—CO;

$R^1$=$R^2$=H; $R^3$=para-O—C(O)—$CH_3$; $R^4$=—$CH_2$—Z where Z=4-$CH_3$—$C_6H_4$—CO, H, 2-oxo-benzopyranyl-3-carbonyl, $(CH_2)_3$—$CH_3$, 4-$C_6H_5$—$C_6H_4$;

$R^1$=$R^2$=$R^3$=H; $R^4$=—$CH_2$—Z where Z=$CH_3$, CN, 2-naphthyl;

$R^1$=$R^2$=H; $R^3$=para-butoxy; $R^4$=—$CH_2$—Z where Z=4-Cl—$C_6H_5$, C(O)—$OCH_3$, C(O)—$C_6H_5$, CH=$CH_2$, C(O)—$NH_2$, H, 4-Br—$C_6H_4$—CO, 4-Cl—$C_6H_4$—CO, C(O)—$OC_2H_5$, C(O)—O—$CH_2$—$C_6H_5$, 2-oxo-benzopyranyl-3-carbonyl, C(O)—NH—$C_6H_5$, CN;

$R^1$=$R^2$=H; $R^3$=para-bromo; $R^4$=—$CH_2$—Z where Z=4-Br—$C_6H_4$—CO, 4-Cl—$C_6H_4$—CO, C(O)—$NH_2$, C(O)—$OCH_3$, 4-Cl—$C_6H_5$, 4-Br—$C_6H_4$—NH—CO;

$R^1$=$R^2$=H; $R^3$=meta-fluoro; $R^4$=—$CH_2$—Z where Z=4-Br—$C_6H_4$—CO, C(O)—$NH_2$, C(O)—O—$CH_2$—$C_6H_5$, CN;

$R^1=R^2=H$; $R^3$=para-chloro; $R^4=$—$CH_2$—Z where Z=2-naphthyl, $CH_3$;
$R^1=R^2=H$; $R^3$=para-$OCH_3$; $R^4=$—$CH_2$—Z where Z=2-naphthyl, $CH_3$;
$R^1=R^2=H$; $R^3$=meta-$NO_2$; $R^4=$—$CH_2$—Z where Z=$CH_3$.

Particularly preferred compounds are the compounds of the general formula (I)

in which:

$R^1, R^2, R^3$ are identical or different and independently of one another are selected from the group of the following substituents:
hydrogen;
hydroxyl;
optionally substituted $(C_1–C_4)$-alkyl;
optionally substituted phenyl;
optionally substituted $(C_1–C_4)$-alkoxy;
—O—$(CH_2)_n$—CH=$CH_2$ where n=1;
fluorine, chlorine;
nitro;
cyano;
—C(O)—$R^5$;
—C(O)—$NR^6R^7$;
—$NR^6R^7$;
—$NR^6$—C(O)—$R^8$;
—O—C(O)—$R^8$;
—$SO_2$—$NR^6R^7$; and
—$NR^6$—$SO_2R^8$,
where:
$R^5$ denotes:
hydrogen;
hydroxyl;
optionally substituted $(C_1–C_4)$-alkyl;
optionally substituted $(C_3–C_7)$-cycloalkyl;
optionally substituted $(C_1–C_4)$-alkoxy;
optionally substituted phenyl;
optionally substituted phenyloxy; or
—O—$(CH_2)_n$-phenyl where n=1,
where the phenyl group may be fused via two adjacent ring atoms to optionally substituted $(C_5–C_6)$-cycloalkyl,
or
$R^5$ represents a 5- to 7-membered saturated or unsaturated heterocycle which for its part may be mono- or polysubstituted by
an oxo group (=O);
fluorine, chlorine;
optionally substituted $(C_1–C_4)$-alkyl;
nitro;
cyano;
hydroxyl;
optionally substituted phenyl; or
by $(C_1–C_4)$-alkoxy,
or
$R^5$ represents optionally substituted 5- to 6-membered heteroaryl having up to 3 heteroatoms from the group consisting of N, O and S, selected from the group consisting of furanyl, pyrrolyl, thienyl, thiazolyl, oxazolyl, imidazolyl, triazolyl, pyridyl, pyrimidyl and pyridazinyl,
where the heterocycle and the heteroaryl ring may each optionally be fused via two adjacent ring atoms to optionally substituted phenyl or optionally substituted $(C_5–C_6)$-cycloalkyl, and $R^6$ and $R^7$ are identical or different and represent
hydrogen;
optionally substituted $(C_1–C_4)$-alkyl;
optionally substituted phenyl; or
represent optionally substituted 5- to 6-membered heteroaryl having up to 3 heteroatoms from the group consisting of N, O and S selected from the group consisting of furanyl, pyrrolyl, thienyl, thiazolyl, oxazolyl, imidazolyl, triazolyl, pyridyl, pyrimidyl and pyridazinyl,
or
$R^6$ and $R^7$ together with the nitrogen atom to which they are optionally attached form a 5- to 7-membered saturated or unsaturated heterocycle having up to 3 heteroatoms from the group consisting of N, O and S which for its part may optionally be mono- or polysubstituted by identical or different substituents from the group consisting of
an oxo group (=O);
fluorine, chlorine;
$(C_1–C_4)$-alkyl;
nitro;
cyano;
hydroxyl;
phenyl; or
$(C_1–C_4)$-alkoxy,
and
$R^8$ represents $NR^6R^7$ where $R^6$ and $R^7$ are as defined above;
optionally substituted $(C_1–C_4)$-alkyl;
$(C_1–C_4)$-alkoxy;
optionally substituted phenyl;
phenyloxy; or
—O—$(CH_2)_n$-phenyl where n=1,
and
$R^4$ represents straight-chain or branched $(C_1–C_4)$-alkyl or $(C_2–C_4)$-alkenyl which are optionally mono- or polysubstituted by
hydroxyl;
fluorine, chlorine;
cyano;
—C(O)—$R^5$ where $R^5$ is as defined above;
—C(O)—$NR^6R^7$ where $R^6$ and $R^7$ are as defined above;
—$NR^6R^7$ where $R^6$ and $R^7$ are as defined above;
—$NR^6$—C(O)—$R^8$ where $R^6$ and $R^8$ are as defined above;
—$SO_2$—$NR^6R^7$ where $R^6$ and $R^7$ are as defined above;
—$NR^6$—$SO_2$—$R^8$ where $R^6$ and $R^8$ are as defined above;
—C(O)—$(CH_2)_n$—C(O)—$R^8$ where n=0 to 2 and $R^8$ is as defined above;
$(C_1–C_4)$-alkoxy;
optionally substituted phenyloxy;
optionally substituted 5- to 6-membered heteroaryl having up to 3 heteroatoms from the group consisting of N, O and S selected from the group consisting of furanyl, pyrrolyl, thienyl, thiazolyl, oxazolyl, imidazolyl, triazolyl, pyridyl, pyrimidyl and pyridazinyl;
optionally substituted phenyl; or
by a 5- to 7-membered saturated or unsaturated heterocycle having up to 3 heteroatoms from the group consisting of N, O and S which for its part may optionally be mono- or polysubstituted by identical or different substituents from the group consisting of an oxo group (=O); fluorine, chlorine; $(C_1–C_4)$-alkyl; nitro; cyano; hydroxyl; phenyl; or by $(C_1–C_4)$-alkoxy, where the heterocycle and the heteroaryl ring may each optionally be fused via two adjacent rings atoms to optionally substituted phenyl,
or
R⁴ represents a 5- to 7-membered saturated or unsaturated heterocycle having up to 3 heteroatoms from the group consisting of N, O and S,
which for its part may optionally be mono- or polysubstituted by identical or different substituents from the group consisting of an oxo group (=O); fluorine, chlorine; (C₁–C₄)-alkyl; nitro; cyano; hydroxyl; phenyl; or by (C₁–C₄)-alkoxy and
which may optionally be fused via two adjacent ring atoms to optionally substituted phenyl or optionally substituted (C₅–C₆)-cycloalkyl,
and their tautomers and their respective salts, hydrates and alkoxides,
except for the following compounds of the general formula (I), in which the radicals R¹, R², R³ and R⁴ are as defined below:
R¹=R²=H; R³=para-OH; R⁴=—CH₂—Z where Z=CN, C(O)—OC₂H₅, 4-Br—C₆H₄—CO, 4-n-butyl-C₆H₄—CO, H, C₆H₅, C(O)—O—CH₂—C₆H₅, C(O)—OCH₃, C(O)—OH, 2-oxo-benzo-pyranyl-3-carbonyl, 4-Cl—C₆H₄—CO, 3-Br—C₆H₄—CO, 4-C₆H₅—C₆H₄—CO, 4-CH₃—C₆H₄—CO, 3,4-Cl₂—C₆H₃—CO;
R¹=R²=H; R³=meta-OH; R⁴=—CH₂—Z where Z=4-Br—C₆H₄—NH—CO, 2-oxo-benzo-pyranyl-3-carbonyl, 4-Cl—C₆H₄—CO;
R¹=R²=H; R³=para-O—C(O)—CH₃; R⁴=—CH₂—Z where Z=4-CH₃—C₆H₄—CO, H, 2-oxo-benzopyranyl-3-carbonyl, 4-C₆H₅—C₆H₄;
R¹=R²=R³=H; R⁴=—CH₂—Z where Z=CH₃, CN;
R¹=R²=H; R³=para-butoxy; R⁴=—CH₂—Z where Z=4-Cl—C₆H₅, C(O)—OCH₃, C(O)—C₆H₅, CH=CH₂, C(O)—NH₂, H, 4-Br—C₆H₄—CO, 4-Cl—C₆H₄—CO, C(O)—OC₂H₅, C(O)—O—CH₂—C₆H₅, 2-oxo-benzopyranyl-3-carbonyl, C(O)—NH—C₆H₅, CN;
R¹=R²=H; R³=meta-fluoro; R⁴=—CH₂—Z where Z=4-Br—C₆H₄—CO, C(O)—NH₂, C(O)—O—CH₂—C₆H₅, CN;
R¹=R²=H; R³=para-chloro; R⁴=—CH₂—Z where Z=CH₃;
R¹=R²=H; R³=para-OCH₃; R⁴=—CH₂—Z where Z=CH₃;
R¹=R²=H; R³=meta-NO₂; R⁴=—CH₂—Z where Z=CH₃.
Particular preference according to the invention is given to compounds of the general formula (I)
in which:
R¹, R², R³ are identical or different and independently of one another are selected from the group of the following substituents:
hydrogen;
hydroxyl;
methyl;
trifluoromethyl;
methoxy;
radicals of the formulae —O—CH₂—CH₂—OH, —O—CH₂—COOH or —O—CH₂—CH=CH₂;
fluorine, chlorine or bromine;
nitro;
cyano;
—C(O)OH or —C(O)OCH₃;
—C(O)NH₂;
—NH₂;
—NH—C(O)—CH₃;
—O—C(O)—CH₃ or —O—C(O)—C₂H₅;
radicals of the formulae

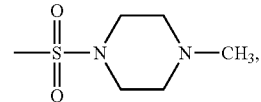

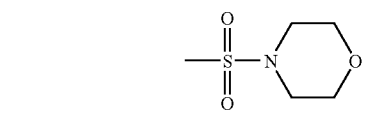

or

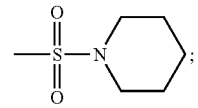

and
—NH—SO₂CH₃ or —NH—SO₂C₆H₅,
and
R⁴ represents straight-chain or branched (C₁–C₄)-alkyl which is optionally mono- or polysubstituted by
hydroxyl;
amino;
—C(O)—OCH₃;
—C(O)—NH₂, —C(O)—HNCH₃, —C(O)—HNC₂H₅, or —C(O)—HNC₆H₅;
—NHC(O)NH₂, —NHC(O)NHCH₃, —NHC(O)NHC₂H₅, —NHC(O)OCH₃ or —NHC(O)OC₂H₅;
—SO₂—NH₂;
—NH—SO₂—CH₃ or —NH—SO₂—C₂H₅;
—OCH₃;
phenyl, which may be substituted by nitro, cyano, fluorine, methoxy, difluoromethoxy, methoxycarbonyl or p-tolylsulfonylmethyl;
pyridyl, furyl, imidazolyl, benzimidazolyl or thiazolyl, which may in each case be mono- or disubstituted by identical or different substituents from the group consisting of methyl, nitro and chlorine;
oxadiazolyl which may be substituted by phenyl or methoxyphenyl;
or
a radical of the formula

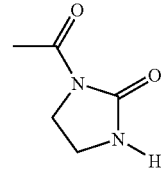

or
R⁴ represents allyl or 3,3-dimethylallyl,
and their tautomers and their respective salts, hydrates and alkoxides, except for the following compounds of the general formula (I), in which the radicals $R^1$, $R^2$, $R^3$ and $R^4$ are as defined below:

$R^1=R^2=H$; $R^3$=para-OH; $R^4=$—$CH_2$—Z where Z=H, $C_6H_5$, C(O)—$OCH_3$;

$R^1=R^2=H$; $R^3$=para-O—C(O)—$CH_3$; $R^4=$—$CH_2$—Z where Z=H;

$R^1=R^2=R^3=H$; $R^4=$—$CH_2$—Z where Z=$CH_3$;

$R^1=R^2=H$; $R^3$=meta-fluoro; $R^4=$—$CH_2$—Z where Z=C(O)—$NH_2$;

$R^1=R^2=H$; $R^3$=para-chloro; $R^4=$—$CH_2$-Z where Z=$CH_3$;

$R^1=R^2=H$; $R^3$=para-$OCH_3$; $R^4=$—$CH_2$—Z where Z=$CH_3$;

$R^1=R^2=H$; $R^3$=meta-$NO_2$; $R^4=$—$CH_2$—Z where Z=$CH_3$.

Very particular preference according to the invention is given to compounds of the general formula (I)

in which:

$R^1$, $R^2$, $R^3$ are identical or different and independently of one another are selected from the group of the following substituents:

hydrogen;
hydroxyl;
methyl;
methoxy;
radicals of the formulae —O—$CH_2$—$CH_2$—OH, —O—$CH_2$—COOH or —O—$CH_2$—CH=$CH_2$;
fluorine or chlorine;
nitro;
cyano;
—C(O)OH or —C(O)$OCH_3$;
—C(O)$NH_2$;
—$NH_2$;
—NH—C(O)$CH_3$;
—O—C(O)—$CH_3$ or —O—C(O)—$C_2H_5$;
radicals of the formulae

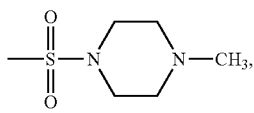

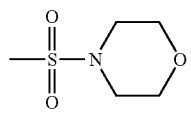

or

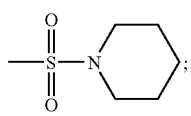

and
—NH—$SO_2CH_3$ or —NH—$SO_2C_6H_5$,
and
$R^4$ represents straight-chain or branched ($C_1$–$C_4$)-alkyl which is optionally mono- or polysubstituted by hydroxyl;

amino;
—C(O)—$OCH_3$;
—C(O)—$NH_2$, —C(O)—$HNCH_3$, —C(O)—$HNC_2H_5$, or —C(O)—$HNC_6H_5$;
—NHC(O)$NH_2$, —NHC(O)$NHCH_3$, —NHC(O)$NHC_2H_5$, —NHC(O)$OCH_3$ or —NHC(O)$OC_2H_5$;
—$SO_2$—$NH_2$;
—NH—$SO_2$—$CH_3$ or —NH—$SO_2$—$C_2H_5$;
—$OCH_3$;
phenyl;
ortho-nitrophenyl; or
a radical of the formula

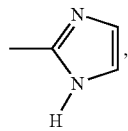

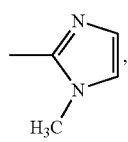

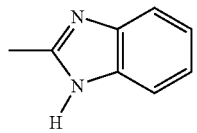

or

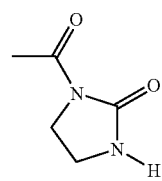

or
$R^4$ represents allyl,
and their tautomers and their respective salts, hydrates and alkoxides, except for the following compounds of the general formula (I), in which the radicals $R^1$, $R^2$, $R^3$ and $R^4$ are as defined below:

$R^1=R^2=H$; $R^4$=para-OH; $R^4=$—$CH_2$—Z where Z=H, $C_6H_5$, C(O)—$OCH_3$;

$R^1=R^2=H$; $R^3$=para-O—C(O)—$CH_3$; $R^4=$—$CH_2$—Z where Z=H;

$R^1=R^2=R^3=H$; $R^4=$—$CH_2$—Z where Z=$CH_3$;

$R^1=R^2=H$; $R^3$=meta-fluoro; $R^4=$—$CH_2$—Z where Z=C(O)—$NH_2$;

$R^1=R^2=H$; $R^3$=para-chloro; $R^4=$—$CH_2$—Z where Z=$CH_3$;

$R^1=R^2=H$; $R^3=$para-$OCH_3$; $R^4=-CH_2-Z$ where $Z=CH_3$;

$R^1=R^2=H$; $R^3=$meta-$NO_2$; $R^4=-CH_2-Z$ where $Z=CH_3$.

The present invention also provides a process for preparing the compounds of the general formula (I).

According to a first variant of the process according to the invention, the compounds of the general formula (I) are prepared by reacting compounds of the general formula (II)

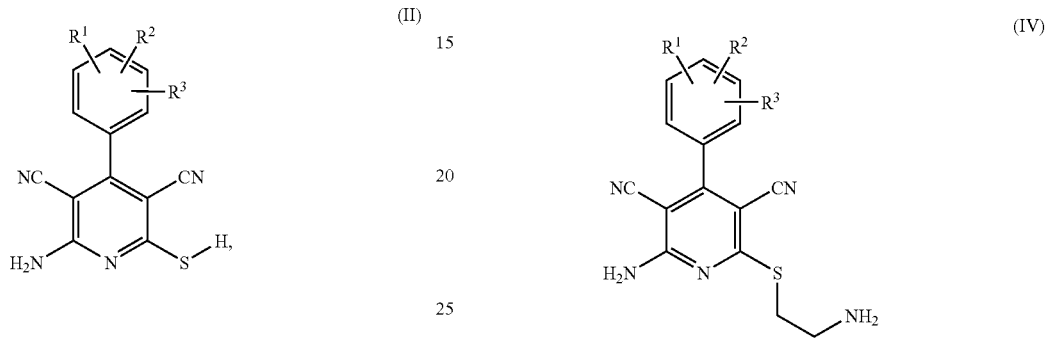

in which the radicals $R^1$, $R^2$ and $R^3$ are as defined above
with compounds of the general formula (III)

$R^4-X$     (III), in which $R^4$ is as defined above
and

X represents a nucleofugic group (preferably halogen, in particular chlorine, bromine or iodine, or mesylate, tosylate, triflate or 1-imidazolyl), in inert solvents, if appropriate in the presence of a base.

The process described above can be illustrated in an exemplary manner by the equation below:

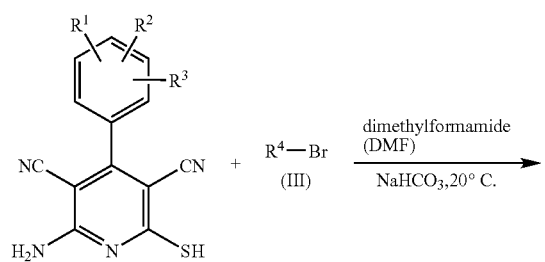

If the radical $R^4$ in the general formula (I) has the meaning of alkyl, substituted by the radicals $-NR^6-C(O)-R^8$, $-NR^6-C(O)-NR^6R^7$, $-NR^6-SO_2-R^8$, where the radicals $R^6$, $R^7$ and $R^8$ are as defined above, it is alternatively, according to a second variant of the process according to the invention, also possible to prepare the compounds of the general formula (I) by initially reacting the compounds of the general formula (II) with 2-bromoethylamine to give compounds of the general formula (IV)

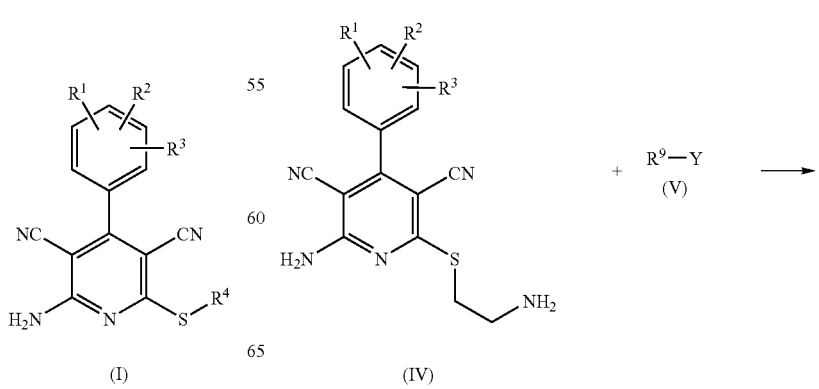

which are then reacted with compounds of the general formula $R^9-Y$     (V), in which $R^9$ has the meaning $-C(O)-R^8$, $-C(O)-O-R^8$, $-C(O)-NR^6R^7$, $-SO_2-R^8$ where $R^8$ is as defined above and Y represents a nucleofugic group, preferably halogen, in particular chlorine, bromine or iodine, or mesylate, tosylate, triflate or 1-imidazolyl, or else $R^9$ has the meaning $R^6$ and Y represents the group $O=C=N-$, in inert solvents, if appropriate in the presence of a base.

The second variant, described above, of the process according to the invention can be illustrated in an exemplary manner by the following equation:

-continued

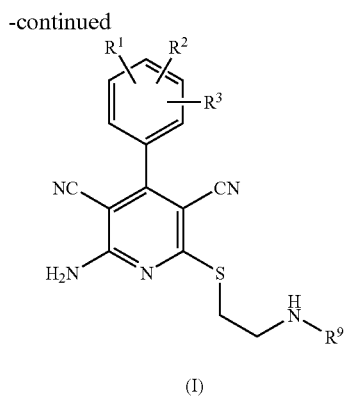

(I)

The nucleofugic group X, which is sometimes also referred to as leaving group, can be introduced into the reaction separately or else be generated in situ by customary methods, for example by the "Mitsunobu reaction".

Suitable solvents for the process according to the invention are all organic solvents which are inert under the reaction conditions. These include alcohols such as methanol, ethanol and isopropanol, ketones such as acetone and methyl ethyl ketone, acyclic and cyclic ethers such as diethyl ether and tetrahydrofuran, esters such as ethyl acetate or butyl acetate, hydrocarbons such as benzene, xylene, toluene, hexane or cyclohexane, dimethylformamide, acetonitrile, pyridine, dimethyl sulfoxide (DMSO), chlorinated hydrocarbons such as dichloromethane, chlorobenzene or dichloroethane or hexamethylphosphoric triamide. Water is also suitable for use as solvent. Particular preference is given to dimethylformamide. It is also possible to use mixtures of the solvents mentioned above.

Suitable bases are the customary inorganic or organic bases. These preferably include alkali metal hydroxides, such as, for example, sodium hydroxide or potassium hydroxide, or alkali metal carbonates, such as sodium carbonate or potassium carbonate or sodium bicarbonate or potassium bicarbonate, or sodium methoxide or potassium methoxide or sodium ethoxide or potassium ethoxide or potassium tert-butoxide, or else amides, such as sodium amide, lithium bis-(trimethylsilyl)amide or lithium diisopropylamide, or organometallic compounds, such as butyllithium or phenyllithium, or else amines, such as triethylamine and pyridine. Preference is given to the alkali metal carbonates and alkali metal bicarbonates.

Here, the base can be employed in an amount of from 1 to 10 mol, preferably from 1 to 5 mol, in particular from 1 to 4 mol, based on 1 mol of the compounds of the general formula (II) or (IV).

The reaction generally takes place in a temperature range of from −78° C. to reflux temperature. preferably in the range from −78° C. to +40° C., in particular at room temperature.

The reaction can be carried out at atmospheric, elevated or reduced pressure (for example in the range from 0.5 to 5 bar). In general, the reaction is carried out at atmospheric pressure.

The person skilled in the art is familiar with numerous modifications of the conditions mentioned above which are within the knowledge of the average expert and within the scope of the present invention.

The compounds of the general formulae (II) are likewise known per se to the person skilled in the art or can be prepared by customary methods known from the literature. Reference may be made in particular to the following publications, the respective content of which is expressly incorporated herein by way of reference:

Dyachenko et al., Russian Journal of Chemistry, Vol. 33, No. 7, 1997, pages 1014–1017 and Vol. 34, No. 4, 1998, pages 557–563;

Dyachenko et al., Chemistry of Heterocyclic Compounds, Vol. 34, No. 2, 1998, pages 188–194;

Qintela et al., European Journal of Medicinal Chemistry, Vol. 33, 1998, pages 887–897;

Kandeel et al., Zeitschrift für Naturforschung 42b, 107–111 (1987).

It is also possible to prepare the compounds of the general formula (II) from compounds of the general formula (VI) by reaction with an alkali metal sulfide. This preparation method can be illustrated in an exemplary manner by the equation below:

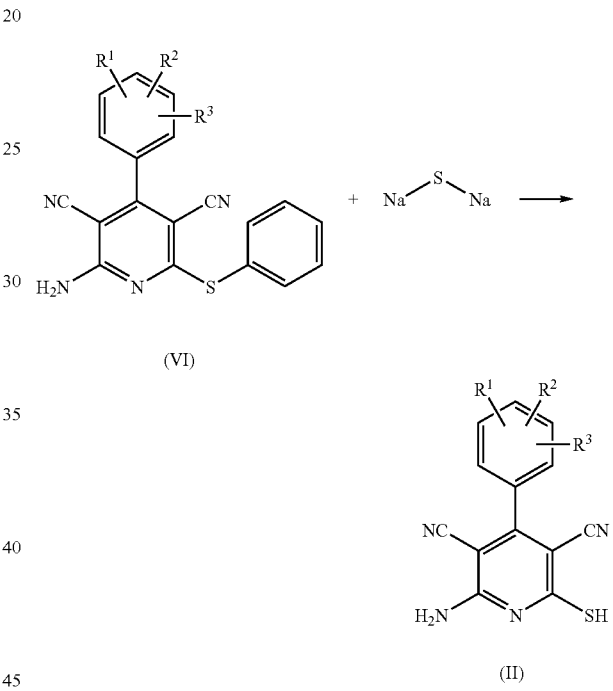

The alkali metal sulfide used is preferably sodium sulfide in an amount of from 1 to 10 mol, preferably from 1 to 5 mol, in particular from 1 to 4 mol, based on 1 mol of the compounds of the general formula (VI).

Suitable solvents are all organic solvents which are inert under the reaction conditions. These include N,N-dimethylformamide, N-methylpyrrolidinone, hexamethylphosphoric triamide, pyridine and acetonitrile. Particularly preference is given to N,N-dimethylformamide. It is also possible to use mixtures of the solvents mentioned above.

The reaction is generally carried out in a temperature range of from +20° C. to reflux temperature, preferably in the range from +20° C. to +120° C., in particular at from +60° C. to +100° C.

The reaction can be carried out at atmospheric, elevated or reduced pressure (for example in the range from 0.5 to 5 bar). In general, the reaction is carried out at atmospheric pressure.

The person skilled in the art is familiar with numerous modifications of the conditions mentioned above which are within the knowledge of the average expert and within the scope of the present invention.

The compounds of the general formulae (VI) are likewise known per se to the person skilled in the art or can be prepared by customary methods known from the literature. Reference may be made in particular to the publication Kambe et al., *Synthesis*, 531 (1981) the content of which is expressly incorporated herein by way of reference.

The compounds of the general formulae (III) or (V) are either commercially available or known per se to the person skilled in the art or can be prepared by customary methods.

Surprisingly, the compounds of the general formula (I) have an unforeseeable useful pharmacological activity spectrum and are therefore suitable in particular for the prophylaxis and/or treatment of disorders.

This is because it has now been found, unexpectedly, that the substances of the formula (I) above are suitable for the prophylaxis and/or treatment of a large number of disorders, i.e. in particular, for example, disorders of the cardiovascular system (cardiovascular disorders); urogenital disorders; respiratory disorders; inflammatory and neuroinflammatory disorders; diabetes, in particular diabetes mellitus; cancer; and finally also neurodegenerative disorders, such as, for example, Parkinson's disease, and also pain.

In the context of the present invention, cardiovascular disorders are to be understood as meaning, in particular, for example the following disorders: coronary heart disease; hypertension (high blood pressure); restinosis such as, for example, restinosis after balloon dilatation of peripheral blood vessels; arteriosclerosis; tachycardia; arrhythmias; peripheral and cardiovascular disorders; stable and unstable angina pectoris; and atrial fibrillation.

The compounds of the general formula (I) are furthermore also suitable for reducing the myocardial area effected by an infarct.

The compounds of the general formula (I) are furthermore suitable for the treatment and prophylaxis of thromboembolic disorders and ischemias such as myocardial infarction, stroke and transitory ischemic attacks.

A further area of indication for which the compounds of the general formula (I) are suitable is the prophylaxis and/or therapy of urogenital disorders, such as, for example, irritable bladder, erectile dysfunction and female sexual dysfunction, and additionally also the prophylaxis and/or treatment of inflammatory disorders, such as, for example, asthma and inflammable dermatoses, of neuroinflammatory disorders of the central nervous system, such as, for example, conditions after cerebral infarction, Alzheimer's disease, furthermore also neurodegenerative disorders such as Parkinson's disease, and also pain.

A further area of indication is respiratory disorders such as, for example, asthma, chronic bronchitis, pulmonary emphysema, bronchiectases, cystic fibrosis (mucoviscidosis) and pulmonary hypertension.

The compounds of the general formula (I) are furthermore also suitable for the prophylaxis and/or therapy of hepatic fibrosis and cirrhosis of the liver.

Finally, the compounds of the general formula (I) are also suitable for the prophylaxis and/or therapy of diabetes, in particular diabetes mellitus.

Accordingly, the present invention also relates to the use of the substances of the general formula (I) for preparing medicaments and pharmaceutical compositions for the prophylaxis and/or treatment of the clinical features mentioned above.

The present invention furthermore relates to a method for the prophylaxis and/or the treatment of the clinical pictures mentioned above using substances of the general formula (I).

The pharmaceutical activity of the abovementioned compounds of the general formula (I) can be explained by their action as selective ligands on individual subtypes or a plurality of subtypes of the adenosine receptors, in particular as selective ligands on adenosine A1, adenosine A2a and/or adenosine A2b receptors, preferably as selective ligands on adenosine A1 and/or adenosine A2b receptors.

In the context of the present invention, "selective" are adenosine receptor ligands where, firstly, a clear effect on one or more adenosine receptor subtypes and, secondly, no or a considerably weaker effect on one or more other adenosine receptor subtypes can be observed, where, with respect to the test methods for the selectivity of action, reference is made to the test methods described in section A. II.

Compared to adenosine receptor ligands of the prior art, the substances of the general formula (I) are much more selective. Thus, for example, compounds of the general formula (I) in which $R^4$ represents $(C_1-C_4)$-alkyl which is substituted by a group of the formula —$C(O)NR^6R^7$, where $R^6$ and $R^7$ are identical or different and are hydrogen or optionally substituted $(C_1-C_3)$-alkyl, are generally selective on adenosine A2b receptors.

On the other hand, compounds of the general formula (I) in which $R^4$ represents $(C_1-C_4)$-alkyl substituted by one or more hydroxyl groups generally act selectively on adenosine A1 receptors.

Compounds of the general formula (I) in which $R^4$ represents $(C_1-C_4)$-alkyl substituted by imidazolyl or optionally substituted benzyl, in turn, generally act selectively on adenosine A1 and adenosine A2b receptors.

This receptor selectivity can be determined by biochemical measurement of the intracellular messenger cAMP in cells which specifically only express one subtype of the adenosine receptors. In the case of agonists, an increase in the intracellular cAMP concentration is observed; in the case of antagonists, a decrease in the intracellular cAMP concentration after prior stimulation with adenosine or adenosine-like substances is observed (see the publications B. Kull, G. Arslan, C. Nilsson, C. Owman, A. Lorenzen, U. Schwabe, B. B. Fredholm, "Differences in the order of potency for agonists but not antagonists at human and rat adenosine A2A receptors", *Biochem. Pharmacol.*, 57 (1999) pages 65–75; and S. P. Alexander, J. Cooper, J. Shine, S. J. Hill, "Characterization of the human brain putative A2B adenosine receptor expressed in Chinese hamster ovary (CHO.A2B4) cells", *Br. J. Pharmacol.*, 119 (1996) pages 1286–90, the respective disclosure of which is hereby expressly incorporated by way of reference).

Accordingly, the present invention also provides the use of selective adenosine receptor ligands, in particular of selective adenosine A1, adenosine A2a and/or adenosine A2b receptor ligands, for preparing medicaments and pharmaceutical compositions for the prophylaxis and/or treatment of disorders, in particular, for example, disorders of the cardiovascular system (cardiovascular disorders); urogenital disorders; inflammatory and neuroinflammatory disorders; neurodegenerative disorders; respiratory disorders; hepatic fibrosis, cirrhosis of the liver; cancer; and finally diabetes, in particular diabetes mellitus, where, with respect to the individual areas of indication, reference is also made to what has been said above.

Thus, compounds of the general formula (I) which bind selectively to adenosine A1 receptors are preferably suitable for myocardial protection and for the prophylaxis and/or treatment of tachycardias, atrial arrhythmias, cardiac insufficiency, of acute kidney failure, diabetes and of pain. Compounds of the general formula (I) which bind selectively to adenosine A2a receptors, on the other hand, are preferably suitable for the prophylaxis and/or treatment of thromboembolic disorders, of neurodengenerative disorders such as Parkinson's disease and also for wound healing. Compounds of the general formula (I) which bind selectively to adenosine A2b receptors, in turn, are preferably suitable for the prophylaxis and/or therapy of hepatic fibrosis, of myocardial infarction, of neuroinflammatory disorders, Alzheimer's disease, of urogenital incontinence and also of respiratory disorders such as, for example, asthma and chronic bronchitis.

The present invention also provides medicaments and pharmaceutical compositions comprising at least one selective adenosine and/or adenosine A2b receptor ligand, preferably at least one compound of the general formula (I), together with one or more pharmacologically acceptable excipients or carriers, and their use for the purposes mentioned above.

Suitable for administering the compounds of the general formula (I) are all customary administration forms, i.e. oral, parenteral, inhalative, nasal, sublingual, rectal or external, such as, for example, transdermal, with particular preference oral or parenteral. In the case of parenteral administration, particular mention may be made of intravenous, intramuscular and subcutaneous administration, for example as a subcutaneous depot. Very particular preference is given to oral administration.

Here, the active compounds can be administered on their own or in the form of preparations. Suitable preparations for oral administration are inter alia tablets, capsules, pellets, sugar-coated tablets, pills, granules, solid and liquid aerosols, syrups, emulsions, suspensions and solutions. Here, the active compound has to be present in such a quantity that a therapeutic effect is obtained. In general, the active compound can be present in a concentration of from 0.1 to 100% by weight, in particular from 0.5 to 90% by weight, preferably from 5 to 80% by weight. In particular, the concentration of the active compound should be 0.5–90% by weight, i.e. the active compound should be present in quantitites sufficient to achieve the dosage range mentioned.

To this end, the active compounds can be converted in a manner known per se into the customary preparations. This is achieved using inert nontoxic pharmaceutically suitable carriers, excipients, solvents, vehicles, emulsifiers and/or dispersants.

Excipients which may be mentioned are, for example: water, nontoxic organic solvents such as, for example, paraffins, vegetable oils (for example sesame oil), alcohols (for example ethanol, glycerol), glycols (for example polyethylene glycol), solid carriers, such as natural or synthetic ground minerals (for example talc or silicates), sugars (for example lactose), emulsifiers, dispersants (for example polyvinylpyrrolidone) and glidants (for example magnesium sulfate).

In the case of oral administration, tablets may, of course, also contain additives such as sodium citrate, together with adjuvants such as starch, gelatin and the like. Aqueous preparations for oral administration may furthermore be admixed with flavor enhancers or colorants.

In general, it has been found to be advantageous to administer, in the case of parenteral administration, quantities of from about 0.1 to about 10 000 µg/kg, preferably from about 1 to about 1 000 µg/kg, in particular from about 1 µg/kg to about 100 µg/kg, of bodyweight, to obtain effective results. In the case of oral administration, the quantity is from about 0.1 to about 10 mg/kg, preferably from about 0.5 to about 5 mg/kg, in particular from about 1 to about 4 mg/kg, of bodyweight.

In spite of this, it may still be required, depending on bodyweight, administration route, individual response to the active compound, the type of preparation and the time or interval at which administration takes place, to deviate from the quantities mentioned.

The present invention is illustrated by the examples below; however, these examples are only intended to facilitate a better understanding of the invention and not to restrict the invention in any way.

A. EVALUATION OF THE PHYSIOLOGICAL ACTIVITY

I. Demonstration of the Cardiovascular Action

Langendorff Heart of the Rat:

After opening the thoracic cage of anesthetized rats, the heart is removed quickly and introduced into a conventional Langendorff apparatus. The coronary arteries are perfused at a constant volume (10 ml/min), and the resulting perfusion pressure is recorded via an appropriate pressure sensor. In this arrangement, a decrease of the perfusion pressure corresponds to a relaxation of the coronary arteries. At the same time, the pressure which is developed by the heart during each contraction is measured via a balloon introduced into the left ventricle and a further pressure sensor. The frequency of the isolated beating heart is calculated from the number of contractions per time unit.

In this test arrangement, the following values were obtained for the coronary perfusion pressure (the stated percentage refers to the reduction of the coronary perfusion pressure in percent at the respective concentration):

| Compound of the formula (I) used | Reduction of the coronary perfusion pressure in percent at a concentration of | |
|---|---|---|
| | $10^{-7}$ g/ml | $10^{-6}$ g/ml |
| $R^1 = R^2 = H$<br>$R^3$ = para-$CH_3$<br>$R^4$ = —$CH_2$—CH(OH)($CH_2OH$)<br>(compound of example A 198) | no effect observed | about 26% |
| $R^1 = R^2 = H$<br>$R^3$ = para-$CH_3$<br>$R^4$ = —$CH_2$-phenyl<br>(compound of example A 189) | no effect observed | about 37% |

-continued

Compound of the formula (I) used

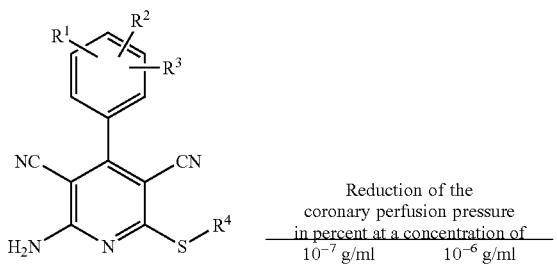

| | Reduction of the coronary perfusion pressure in percent at a concentration of | |
|---|---|---|
| | $10^{-7}$ g/ml | $10^{-6}$ g/ml |
| $R^1 = R^2 = H$<br>$R^3 =$ meta-OH<br>$R^4 = -CH_2-CH_2OH$<br>(compound of example A 43) | about 42% | about 68% |
| $R^1 = R^2 = H$<br>$R^3 =$ para-OH<br>$R^4 = -CH_2-CH_2OH$<br>(compound of example 21) | about 40% | about 75% |
| $R^1 = R^2 = H$<br>$R^3 =$ para-OH<br>$R^4 =$ 2-imidazolylmethyl<br>(compound of example A 379) | about 64% | about 63% |

At the stated concentrations, the substances tested had no effect on the pressure developed during the contraction in the left ventricle and no effect on the heart rate. Thus, it was demonstrated that the substances act selectively only on coronary perfusion.

II. Demonstration of the Receptor Selectivity (Adenosine A1, A2a, A2b and A3 Receptor Selectivity)

Cells of the permanent line CHO (Chinese Hamster Ovary) were stably transfected with cDNA for the adenosine receptor subtypes A1, A2a, A2b and A3. Binding of the substances to the A2a or A2b receptor subtypes was determined by measuring the intracellular cAMP concentration in these cells using a conventional radioimmunological assay (cAMP-RIA, IBL GmbH, Hamburg, Germany).

In the case of the action of the substances as agonists, binding of the substances is expressed in an increase of the intracellular cAMP concentration. In these experiments, the adenosine analogue NECA (5-N-ethylcarboxamido-adenosine), which binds unselectively, but with high affinity, to all adenosine receptor subtypes and has agonistic action (Klotz, K. N., Hessling, J., Hegler, J., Owman, C., Kull, B., Fredholm, B. B., Lohse, M. J., Comparative pharmacology of human adenosine receptor subtypes—characterization of stably transfected receptors in CHO cells, Naunyn Schmiedebergs Arch Pharmacol, 357 (1998), 1–9) was used as reference compound.

The adenosine receptors A1 and A3 are coupled to a Gi protein, i.e. stimulation of these receptors results in an inhibition of adenylate cyclase and thus a reduction of the intracellular cAMP level. To identify A1/A3 receptor agonists, the adenylate cyclase is stimulated using forskolin. However, additional stimulation of the A1/A3 receptors inhibits adenylate cyclase, so that it is possible to detect A1/A3 receptor agonists by a comparatively low concentration of cAMP in the cell.

To demonstrate an antagonistic effect on adenosine receptors, the recombinant cells transfected with the corresponding receptor were prestimulated with NECA, and the effect of the substances on a reduction of the intracellular cAMP concentration by this prestimulation was examined. In these experiments, XAC (xanthine amine congener), which binds unselectively, but with high affinity, to all adenosine receptor subtypes and has antagonistic action (Müller, C. E., Stein, B., Adenosine receptor antagonists: structures and potential therapeutic applications, Current Pharmaceutical Design, 2 (1996), 501–530) was used as reference compound.

In the experiments below, the intracellular cAMP concentration in CHO cells which had been transfected with cDNA for the A2b receptor was determined. What is stated is the cAMP concentration in percent in all cells in a well of a microtiter plate, based on the control value obtained without any substances acting on the cells:

Compound of the formula (I) used

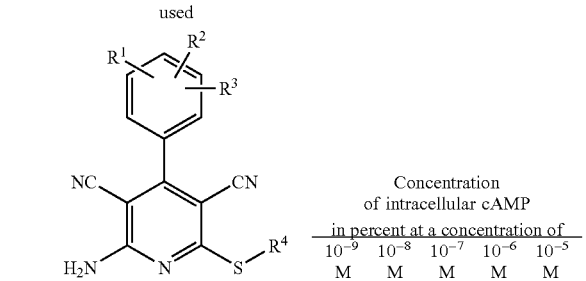

| | Concentration of intracellular cAMP in percent at a concentration of | | | | |
|---|---|---|---|---|---|
| | $10^{-9}$ M | $10^{-8}$ M | $10^{-7}$ M | $10^{-6}$ M | $10^{-5}$ M |
| NECA (reference) | 363 | 340 | 858 | 1226 | 1263 |
| $R^1 = R^2 = H$<br>$R^3 =$ para-OH<br>$R^4 = -CH_2-C(O)NH_2$<br>(compound of example A 1) | | | 837 | 947 | 900 |
| $R^1 = R^2 = H$<br>$R^3 =$ para-OH<br>$R^4 = -CH_2-CH_2OH$<br>(compound of example 21) | | | 253 | 432 | 384 |
| $R^1 = R^2 = H$<br>$R^3 =$ meta-OH<br>$R^4 = -CH_2-CH_2OH$<br>(compound of example A 43) | | | 347 | 674 | 784 |
| $R^1 = R^2 = H$<br>$R^3 =$ meta-OH<br>$R^4 = -CH_2-CH(CH3)OH$<br>(compound of example A 46) | | | 463 | 716 | 753 |
| $R^1 = R^2 = H$<br>$R^3 =$ H<br>$R^4 = -CH_2-CH_2OH$<br>(compound of example A 104) | 100 | 178 | 438 | 586 | 571 |
| $R^1 = R^2 = H$<br>$R^3 =$ para-OH<br>$R^4 =$ 2-imidazolylmethyl<br>(compound of example A 379) | 870 | 846 | 861 | 936 | 1140 |

In these experiments, it was possible to block the action of all substances by the antagonist XAC, which is unselective, but highly specific for adenosine receptors.

In the experiments below, the intracellular cAMP concentration in CHO cells which had been transfected with cDNA for the A2a receptor was determined. What is stated is the cAMP concentration in percent in all cells in a well of a microtiter plate, based on the control value obtained without any substances acting on the cells:

| Compound of the formula (I) used | Concentration of intracellular cAMP in percent at a concentration of | | | | |
|---|---|---|---|---|---|
| | $10^{-9}$ M | $10^{-8}$ M | $10^{-7}$ M | $10^{-6}$ M | $10^{-5}$ M |
| NECA (reference) | 585 | 800 | 1301 | 1992 | 2075 |
| $R^1 = R^2 = H$<br>$R^3$ = para-OH<br>$R^4$ = —CH$_2$—C(O)NH$_2$<br>(compound of example A 1) | | | 92 | 117 | 208 |
| $R^1 = R^2 = H$<br>$R^3$ = para-OH<br>$R^4$ = —CH$_2$—CH$_2$OH<br>(compound of example 21) | | | | 143 | 117 |
| $R^1 = R^2 = H$<br>$R^3$ = meta-OH<br>$R^4$ = —CH$_2$—CH$_2$OH<br>(compound of example A 43) | | | 117 | 200 | 317 |
| $R^1 = R^2 = H$<br>$R^3$ = meta-OH<br>$R^4$ = —CH$_2$—CH(CH3)OH<br>(compound of example A 46) | | | 67 | 108 | 183 |
| $R^1 = R^2 = H$<br>$R^3$ = H<br>$R^4$ = —CH$_2$—CH$_2$OH<br>(compound of example A 104) | 104 | 107 | 107 | 146 | 212 |
| $R^1 = R^2 = H$<br>$R^3$ = para-OH<br>$R^4$ = 2-imidazolylmethyl<br>(compound of example A 379) | 93 | 160 | 218 | 235 | 291 |

In these experiments, it was possible to block the action of all substances by the antagonist XAC, which is unselective, but highly specific for adenosine receptors.

In the following experiments, the intracellular cAMP concentration in CHO cells transfected with the cDNA for the A1 receptor was determined. What is stated is the cAMP concentration in percent in all cells of a well of a microtiter plate, based on the control value obtained without the action of any substance but after prestimulation with 1 μM of forskolin for 15 min (in these measurements, the cAMP concentration without prestimulation with forskolin is 18%):

| Compound of the formula (I) used | Concentration of intracellular cAMP in percent at a concentration of | | |
|---|---|---|---|
| | $10^{-7}$ M | $10^{-6}$ M | $10^{-5}$ M |
| NECA (reference) | 24 | 24 | 28 |
| $R^1 = R^2 = H$<br>$R^3$ = meta-OH<br>$R^4$ = —CH$_2$—CH$_2$OH<br>(compound of example A 43) | 18 | 24 | 22 |
| $R^1 = R^2 = H$<br>$R^3$ = H<br>$R^4$ = —CH$_2$—CH$_2$OH<br>(compound of example A 104) | 28 | 23 | 21 |
| $R^1 = R^2 = H$<br>$R^3$ = para-OH<br>$R^4$ = 2-imidazolylmethyl<br>(compound of example A 379) | 34 | 34 | 35 |

Thus, the compound of example A 1 has a clear agonistic effect on cells which express the adenosine receptor A2b and virtually no effect on cells with the A2a receptor. In contrast, the compounds from example A 43 and A 104 have a clear agonistic effect on cells with the A 1 receptor, virtually no effect on cells with A2a receptors and a considerably weaker effect on cells with the A2b receptor and are therefore selective adenosine A1 receptor agonists. The compound of example A 379, on the other hand, has a clear agonistic effect on cells with the A2b receptor, virtually no effect on cells with A2a receptors and a comparably weaker effect on cells with the A1 receptor and is thus a selective adenosine A2b receptor agonist.

B. SYNTHESIS EXAMPLES

Example 1

2-{[6-Amino-3,5-dicyano-4-(4-hydroxyphenyl)-2-pyridinyl]sulfanyl}-N-methyl-acetamide

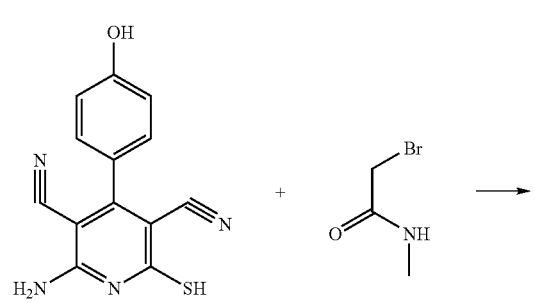

-continued

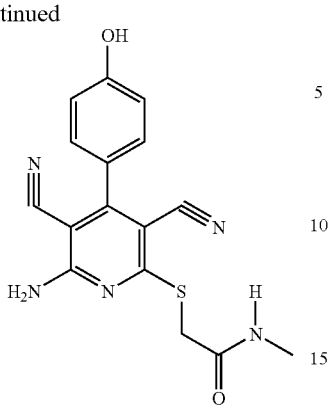

At room temperature (RT), 53.6 mg (0.2 mmol) of 2-amino-4-(4-hydroxyphenyl)-6-sulfanyl-3,5-pyridinedicarbonitrile and 45.6 mg (0.3 mmol) of N-methylbromoacetamide are stirred in 0.5 ml of dimethylformamide (DMF) together with 33.6 mg (0.4 mmol) of NaHCO$_3$ for 4 hours. Thin-layer chromatography (TLC) (CH$_2$Cl$_2$/CH$_3$OH 10:1) shows complete conversion. The entire mixture is diluted with water and ethyl acetate (EA) and the EA phase is dried with MgSO$_4$ and concentrated under reduced pressure. The residue crystallizes from methanol.

Yield: 45 mg (66.3% of theory), white crystals

Mass spectrum: molecular mass calculated: 339, found [M+H]$^+$=340.3

Example 2

2-{[6-Amino-3,5-dicyano-4-(4-hydroxyphenyl)-2-pyridinyl]sulfanyl}-N,N-diethylacetamide

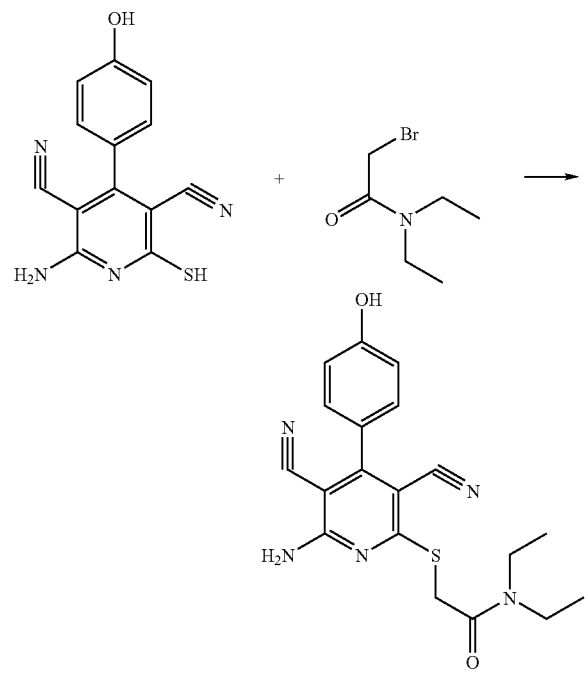

At RT, 53.6 mg (0.2 mmol) of 2-amino-4-(4-hydroxyphenyl)-6-sulfanyl-3,5-pyridinedicarbonitrile and 58.2 mg (0.3 mmol) of N,N-diethylbromoacetamide are stirred in 0.5 ml of DMF together with 33.6 mg (0.4 mmol) of NaHCO$_3$ for 4 hours. TLC (CH$_2$Cl$_2$/CH$_3$OH 10:1) shows complete conversion. The entire mixture is diluted with water and ethyl acetate and the EA phase is dried with MgSO$_4$ and concentrated under reduced pressure. The residue crystallizes from methanol.

Yield: 50 mg (65.5% of theory), white crystals

Mass spectrum: molecular mass calculated: 381, found [M+H]$^+$=382

Example 3

2-{[6-Amino-3,5-dicyano-4-(4-hydroxyphenyl)-2-pyridinyl]sulfanyl}-N-ethylacetamide

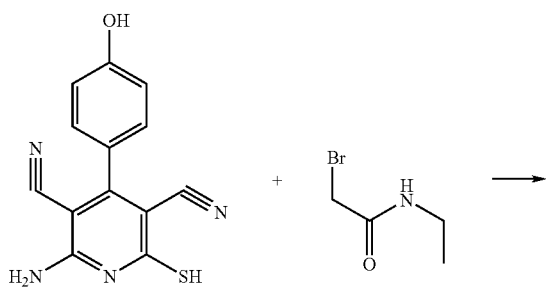

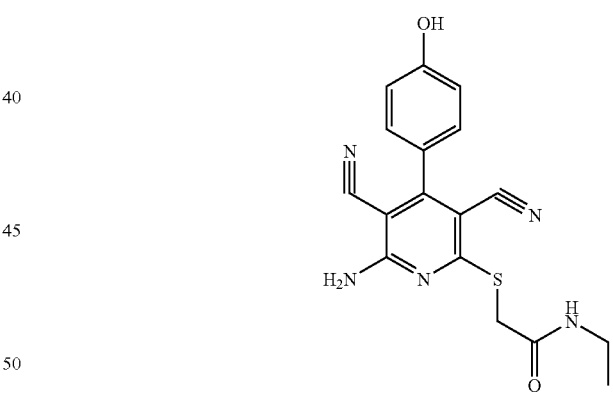

At RT 0.76 g (2 mmol) of 2-amino-4-(4-hydroxyphenyl)-6-sulfanyl-3,5-pyridinedicarbonitrile and 0.5 g (3 mmol) of N-ethylbromoacetamide are stirred in 5 ml of DMF together with 0.34 g (4 mmol) of NaHCO$_3$ for 4 hours. After dilution with water, the mixture is extracted with ethyl acetate and the ethyl acetate phase is dried with MgSO$_4$ and concentrated under reduced pressure. The solid residue obtained after concentration is stirred with methanol. The crystals are filtered off with suction and dried under reduced pressure.

Yield: 0.49 g (69.5% of theory), crystals

Mass spectrum: molecular mass calculated: 353, found [M+H]$^+$=354.2

Example 4

2-Amino-6-[(2-aminoethyl)sulfanyl]-4-(4-hydroxyphenyl)-3,5-pyridinedicarbonitrile

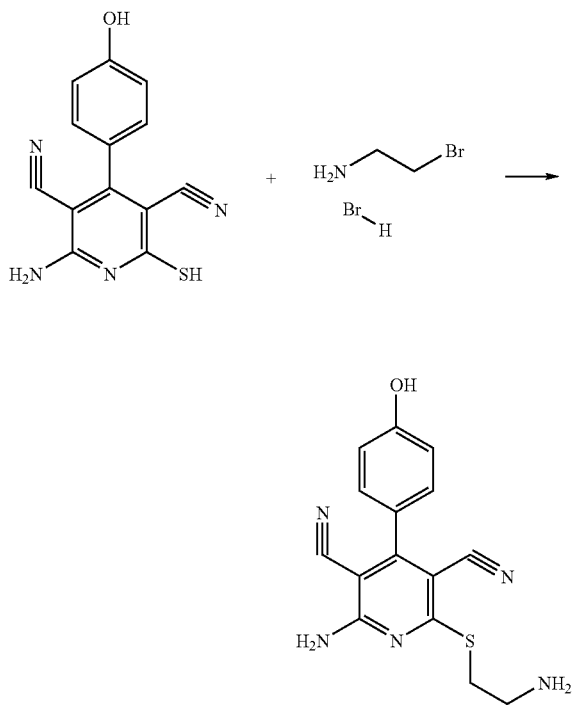

268 mg (1 mmol) of 2-amino-4-(4-hydroxyphenyl)-6-sulfanyl-3,5-pyridinedicarbonitrile, 105 mg (1 mmol) of 2-bromoethylamine hydrobromide and 168 mg (2 mmol) of NaHCO$_3$ are stirred in 1 ml of DMF for 1 hour. The entire mixture is diluted with a few milliliters of 1N HCl. The crystals are filtered off with suction and dried under reduced pressure.

Yield: 200 mg (64.2% of theory), yellow crystals
Mass spectrum: molecular mass calculated: 311, found [M+H]$^+$=312

Example 5

N-(2-{[6-Amino-3,5-dicyano-4-(4-hydroxyphenyl)-2-pyridinyl]sulfanyl}ethyl)-acetamide

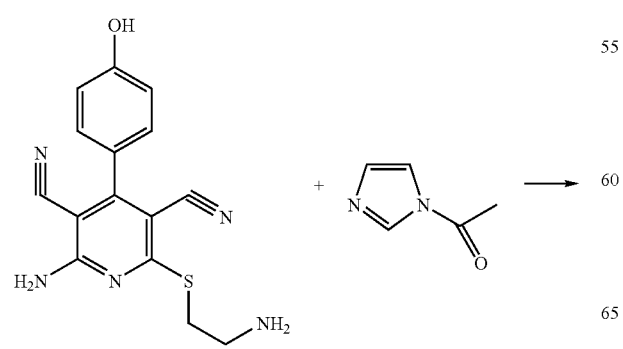

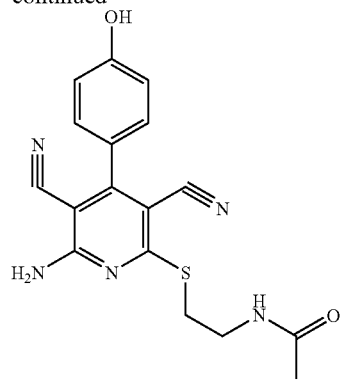

At RT 60 mg (0.2 mmol) of 2-amino-6-[(2-aminoethyl)sulfanyl]-4-(4-hydroxyphenyl)-3,5-pyridinedicarbonitrile and 30 mg (0.3 mmol) of N-acetylimidazole are stirred in 0.5 ml of DMF for 1 hour. Water is slowly added dropwise, the mixture becomes slightly turbid and the crude product crystallizes out. The product is filtered off with suction, washed with water and dried under reduced pressure. This gives 53 mg of yellow crystals. The crystals are dissolved in 1 ml of a 1:1 mixture of CH$_2$Cl$_2$/CH$_3$OH, and a few drops of concentrated ammonia are added (removal of diacetylated byproduct). The mixture is stirred at RT for 5 hours. The product crystallizes out when the reaction solution is concentrated. The product is filtered off with suction and washed with methanol.

Yield: 37 mg (52.3% of theory), almost white crystals
Mass spectrum: molecular mass calculated: 353, found [M+H]$^+$=354

Example 6

2-{[6-Amino-3,5-dicyano-4-(4-hydroxyphenyl)-2-pyridinyl]sulfanyl}methylcarbamate

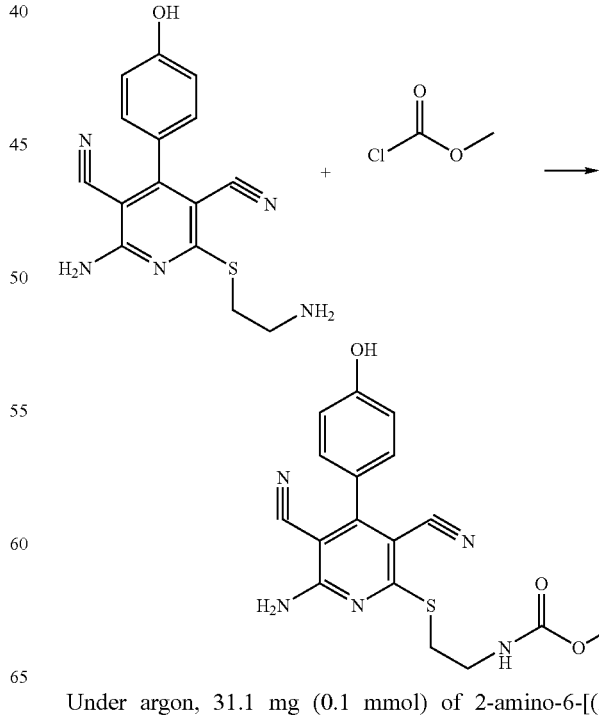

Under argon, 31.1 mg (0.1 mmol) of 2-amino-6-[(2-aminoethyl)sulfanyl]-4-(4-hydroxyphenyl)-3,5-pyridinedicarbonitrile are suspended at RT in 1 to 2 ml of dichloromethane, and the mixture is cooled to from −20 to −25° C. At this temperature, 30.3 mg (0.3 mmol) of triethylamine and 28,3 mg (0.3 mmol) of methyl chloroformate are added. The mixture is stirred at −20 C for 30 minutes and then allowed to warm to 0° C. over a period of 1 hour. The mixture is concentrated under reduced pressure, 4 ml of a 2 molar $NH_3$ solution in methanol are added and the mixture is stirred at RT for 1 hour. The mixture is then concentrated, dissolved in 600 µl of DMSO and purified by preparative HPLC.

HPLC Conditions:
Column: GROM-SIL 120 ODS 4 HE 5µ 50×20 mm
Precolumn: GROM-SIL ODS 4 HE 15µ 10×20 mm
Wavelength: 220 nm
Flow rate: 25 ml/min
Gradient:
A=acetonitrile+0.1% trifluoroacetic acid
B=water+0.1% trifluoroacetic acid
0 min: 10% A; 1.75 min. 10% A; 5.5 min. 90% A; 8 min. 90% A;
8.1 min. 10% A; 9 min. 10% A
Injection volume: 600 µl of DMSO solution
Yield: 21.7 mg (58.7% of theory) of product
Mass spectrum: molecular mass calculated: 369, found $[M+H]^+=370.1$

Example 7

2-{[6-Amino-3,5-dicyano-4-(4-hydroxyphenyl)-2-pyridinyl]sulfanyl}ethylcarbamate

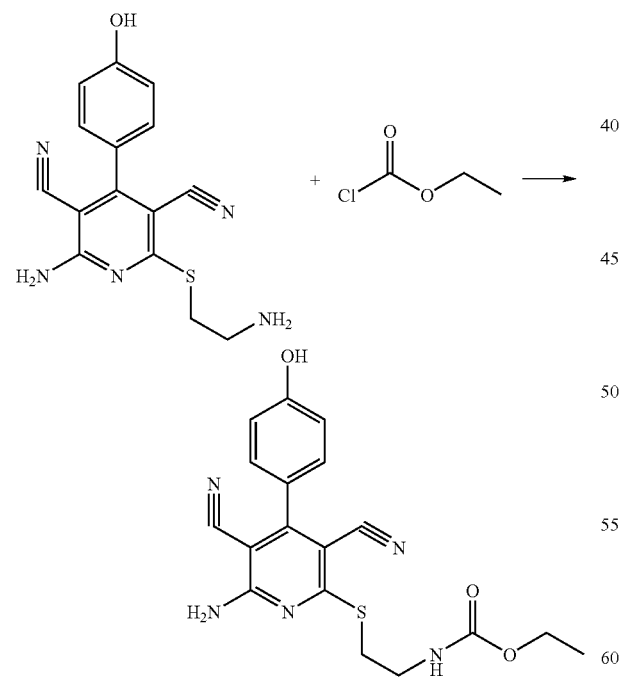

Under argon, 31.1 mg (0.1 mmol) of 2-amino-6-[(2-aminoethyl)sulfanyl]-4-(4-hydroxyphenyl)-3,5-pyridinedicarbonitrile are suspended at RT in 1 to 2 ml of dichloromethane, and the mixture is cooled to from −20 to −25° C. At this temperature, 30.3 mg (0.3 mmol) of triethylamine and 32.6 mg (0.3 mmol) of ethyl chloroformate are added. The mixture is stirred at −20° C. for 30 minutes and then allowed to warm to 0° C. over a period of 1 hour. The mixture is concentrated under reduced pressure, 4 ml of a 2 molar $NH_3$ solution in methanol are added and the mixture is stirred at RT for 1 hour. The mixture is then concentrated, dissolved in 600 µl of DMSO and purified by preparative HPLC.

HPLC Conditions:
Column: GROM-SIL 120 ODS 4 HE 5µ 50×20 mm
Precolumn: GROM-SIL ODS 4 HE 15µ 10×20 mm
Wavelength: 220 nm
Flow rate: 25 ml/min
Gradient:
A=acetonitrile+0.1% trifluoroacetic acid
B=water+0.1% trifluoroacetic acid
0 min: 10% A; 1.75 min. 10% A; 5.5 min. 90% A; 8 min. 90% A;
8.1 min. 10% A; 9 min. 10% A
Injection volume: 600 µl of DMSO solution
Yield: 20.5 mg (53.5% of theory) of product
Mass spectrum: molecular mass calculated: 383, found $[M+H]^+=384.2$

Example 8

4-[2-Amino-3,5-dicyano-6-({2-[(methoxycarbonyl)amino]ethyl}sulfanyl)-4-pyridinyl]-phenyl-methyl-carbonate

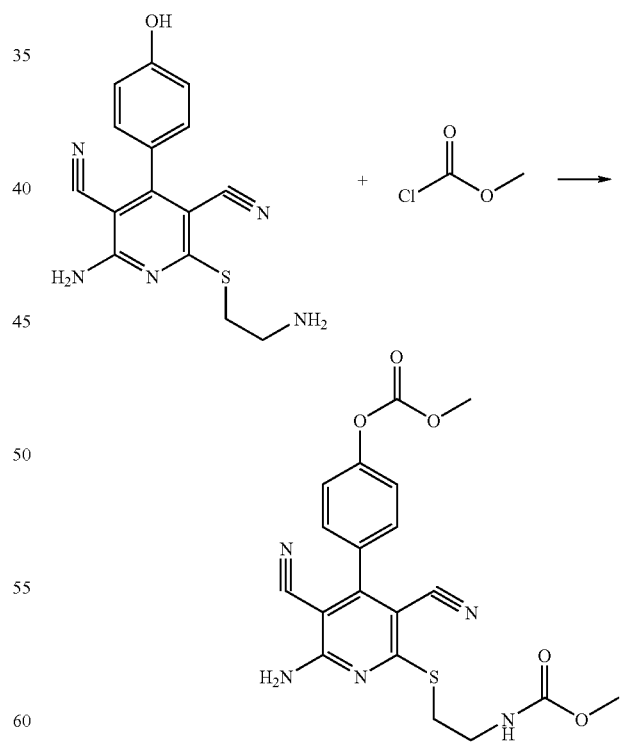

Under argon, 31.1 mg (0.1 mmol) of 2-amino-6-[(2-aminoethyl)sulfanyl]-4-(4-hydroxyphenyl)-3,5-pyridinedicarbonitrile are suspended at RT in 1 to 2 ml of dichloromethane, and the mixture is cooled to from −20 to −25° C. At this temperature, 10.1 mg (0.1 mmol) of triethylamine and 9.4 mg (0.1 mmol) of methyl chloroformate are added. The mixture is stirred at −20° C. for 30 minutes and then allowed to warm to 0° C. over a period of 1 hour. The mixture is then concentrated dissolved in 600 µl of DMSO and purified by preparative HPLC.

HPLC Conditions:
Column: GROM-SIL 120 ODS 4 HE 5µ 50×20 mm
Precolumn: GROM-SIL ODS 4 HE 15µ 10×20 mm
Wavelength: 220 nm
Flow rate: 25 ml/min
Gradient:
A=acetonitrile+0.1% trifluoroacetic acid
B=water+0.1% trifluoroacetic acid
0 min: 10% A; 1.75 min. 10% A; 5.5 min. 90% A; 8 min. 90% A;
8.1 min. 10% A; 9 min. 10% A
Injection volume: 600 µl of DMSO solution
Yield: 11.2 mg (26.2% of theory) of product
Mass spectrum: molecular mass calculated: 427, found $[M+H]^+=428.2$ Example 9

4-[2-Amino-3,5-dicyano-6-({2-[(methoxycarbonyl)amino]ethyl}sulfanyl)-4-pyridinyl]phenyl-ethylcarbonate

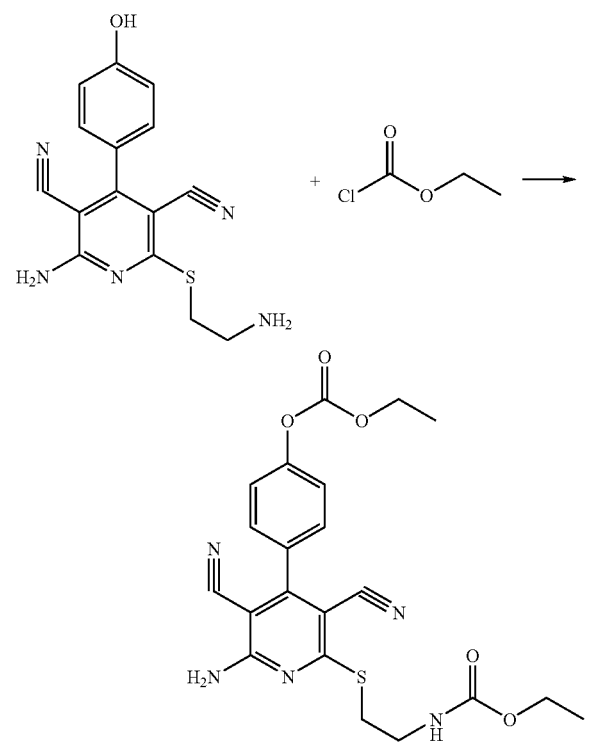

Under argon 31.1 mg (0.1 mmol) of 2-amino-6-[(2-aminoethyl)sulfanyl]-4-(4-hydroxyphenyl)-3,5-pyridinedicarbonitrile are suspended at RT in 1 to 2 ml of dichloromethane, and the mixture is cooled to from −20 to −25° C. At this temperature, 10.1 mg (0.1 mmol) of triethylamine and 10.9 mg (0.1 mmol) of ethyl chloroformate are added. The mixture is stirred at −20° C. for 30 minutes and then allowed to warm to 0° C. over a period of 1 hour. The mixture is then concentrated, dissolved in 600 µl of DMSO and purified by preparative HPLC.

HPLC Conditions:
Column: GROM-SIL 120 ODS 4 HE 5µ 50×20 mm
Precolumn: GROM-SIL ODS 4 HE 15µ 10×20 mm
Wavelength: 220 nm
Flow rate: 25 ml/min
Gradient:
A=acetonitrile+0.1% trifluoroacetic acid
B=water+0.1% trifluoroacetic acid
0 min: 10% A; 1.75 min. 10% A; 5.5 min. 90% A; 8 min. 90% A;
8.1 min. 10% A; 9 min. 10% A
Injection volume: 600 µl of DMSO solution
Yield: 15.2 mg (33.4% of theory) of product
Mass spectrum: molecular mass calculated: 455, found $[M+H]^+=456.2$ Example 10

N-(2-{[6-Amino-3,5-dicyano-4-(4-hydroxyphenyl)-2-pyridinyl]sulfanyl}-ethyl)urea

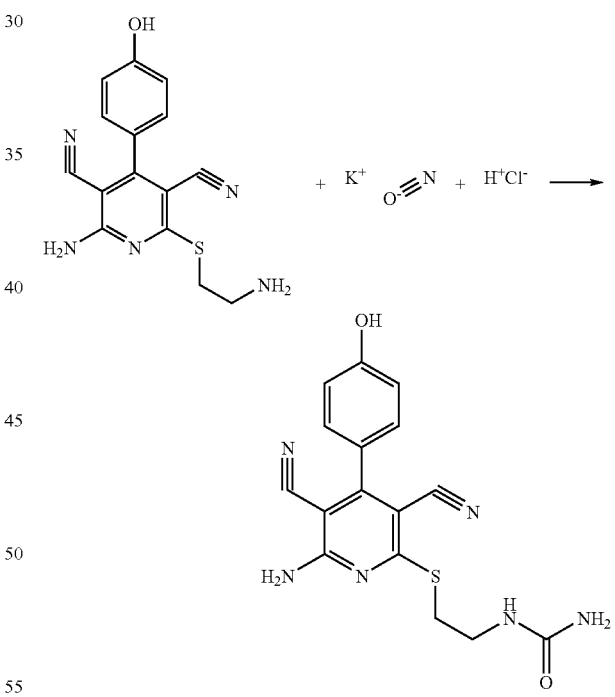

31.1 mg (0.1 mmol) of 2-amino-6-[(2-aminoethyl)sulfanyl]-4-(4-hydroxyphenyl)-3,5-pyridinedicarbonitrile are suspended in 0.91 ml of 1N HCl, and 8.1 mg (0.1 mmol) of potassium cyanate are added. After the addition of a few drops of methanol, the mixture is stirred at 50° C. for a total of 10 hours. The crystals are filtered off with suction and washed with water and ether.

Yield: 16 mg (45.1% of theory) of product
Mass spectrum: molecular mass calculated: 354, found $[M+H]^+=355.1$

Example 11

N-(2-{[6-Amino-3,5-dicyano-4-(4-hydroxyphenyl)-2-pyridinyl]sulfanyl}ethyl)-N'-methylurea

Example 12

N-(2-{[6-amino-3,5-dicyano-4-(4-hydroxyphenyl)-2-pyridinyl]sulfanyl}ethyl)-N'-methylurea

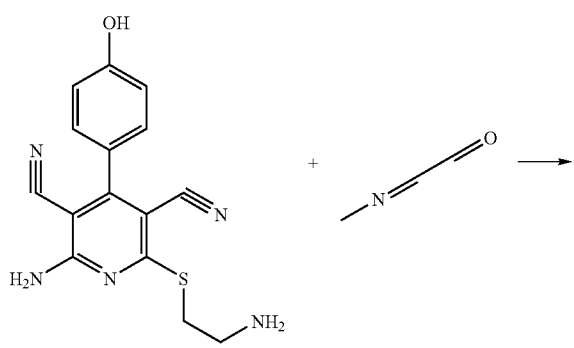

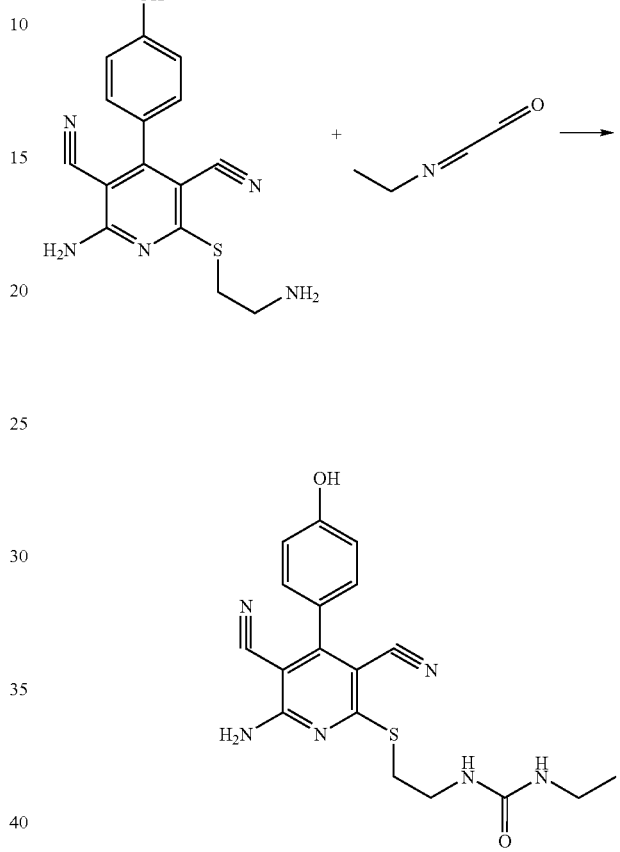

62.2 mg (0.2 mmol) of 2-amino-6-[(2-aminoethyl)sulfanyl]-4-(4-hydroxyphenyl)-3,5-pyridinedicarbonitrile are suspended in 0.4 ml of DMF, and 11.4 mg (0.2 mmol) of methyl isocyanate are added at room temperature. The mixture is stirred overnight, filtered and purified by preparative HPLC.

HPLC Conditions:
Column: GROM-SIL 120 ODS 4 HE 5µ 50×20 mm
Precolumn: GROM-SIL ODS 4 HE 15µ 10×20 mm
Wavelength: 220 nm
Flow rate: 25 ml/min
Gradient:
A=acetonitrile+0.1% trifluoroacetic acid
B=water+0.1% trifluoroacetic acid
0 min: 10% A; 1.75 min. 10% A; 5.5 min. 90% A; 8 min. 90% A;
8.1 min. 10% A; 9 min. 10% A
Injection volume: 400 µl of DMF solution
Yield: 45.9 mg (62.3% of theory) of product
Mass spectrum: molecular mass calculated: 368, found $[M+H]^+ = 369.2$ 62.2 mg (0.2 mmol) of 2-amino-6-[(2-aminoethyl)sulfanyl]-4-(4-hydroxyphenyl)-3,5-pyridinedicarbonitrile are suspended in 0.4 ml of DMF, and 14.2 mg (0.2 mmol) of ethyl isocyanate are added at room temperature. The mixture is stirred overnight, filtered and purified by preparative HPLC.

HPLC Conditions:
Column: GROM-SIL 120 ODS 4 HE 5µ 50×20 mm
Precolumn: GROM-SIL ODS 4 HE 15µ 10×20 mm
Wavelength: 220 nm
Flow rate: 25 mm
Gradient:
A=acetonitrile+0.1% trifluoroacetic acid
B=water+0.1% trifluoroacetic acid
0 min: 10% A; 1.75 min. 10% A; 5.5 min. 90% A; 8 min. 90% A;
8.1 min. 10% A; 9 min. 10% A
Injection volume: 400 µl of DMF solution
Yield: 37.6 mg (49.2% of theory) of product
Mass spectrum: molecular mass calculated: 382, found $[M+H]^+ = 383.2$

Example 13

3,5-Dicyano-4-(3,5-dichloro-4-hydroxyphenyl)-2-carbamoylmethyl-6-amino-pyridine

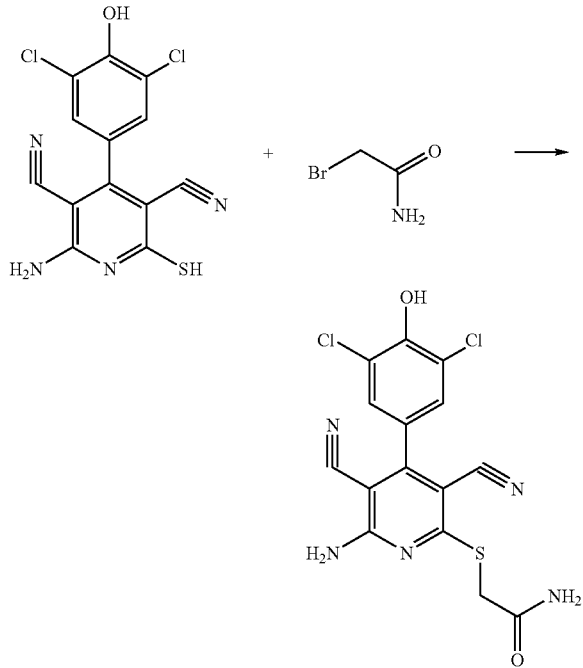

337.2 mg (1 mmol) of 2-amino-4-(3,5-dichloro-4-hydroxyphenyl)-6-sulfanyl-3,5-pyridinedicarbonitrile and 207 mg (1.5 mmol) of bromoacetamide are dissolved in 4 ml of DMF, 336 mg (4 mmol) of $NaHCO_3$ are added and the mixture is stirred at RT for 8 hours. The mixture is diluted with water and washed with ethyl acetate. The aqueous phase is acidified with 1N HCl and the resulting crystals are filtered off with suction and dried.

Yield: 180 mg (45.7% of theory) of product

Mass spectrum: molecular mass calculated: 393, found $[M+H]^+=394.1$

Example 14

2-[(6-Amino-3,5-dicyano-4-{4-[(4-methylpiperazino)sulfonyl]phenyl}-2-pyridinyl)sulfanyl]acetamide

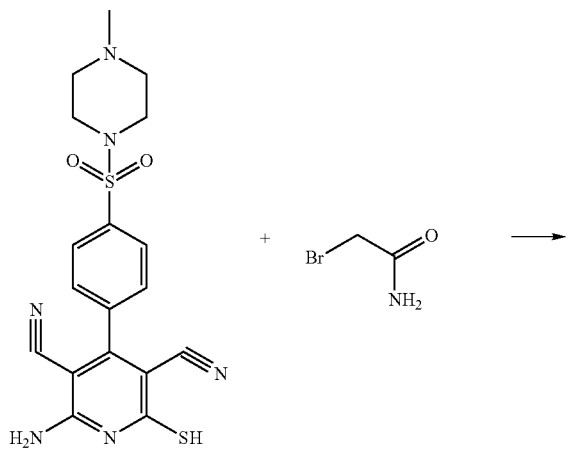

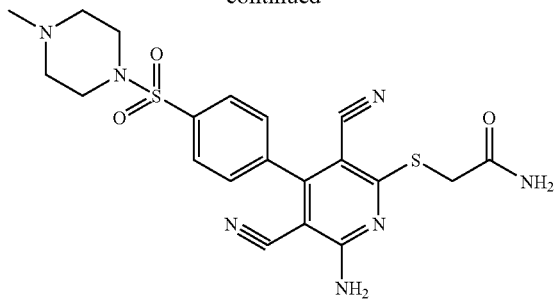

84 mg (0.163 mmol) of 2-amino-4-{4-[(4-methylpiperazino)sulfonyl]phenyl}-6-sulfanyl-3,5-pyridinedicarbonitrile N-methylmorpholinium salt together with 53.3 mg (0.244 mmol) of bromoacetamide and 54.7 mg (0.65 mmol) of $NaHCO_3$ are stirred in 0.5 ml of DMF overnight. After filtration, the reaction solution is initially purified by preparative HPLC. The isolated fraction is reconcentrated under reduced pressure and the residue is purified by preparative thin-layer chromatography.

Yield: 14 mg (18.2% of theory) of product

Mass spectrum: molecular mass calculated: 471, found $[M+H]^+=472.1$

Example 15

2-({6-Amino-3,5-dicyano-4-[4-(piperidinosulfanyl)phenyl]-2-pyridinyl}-sulfanyl)acetamide

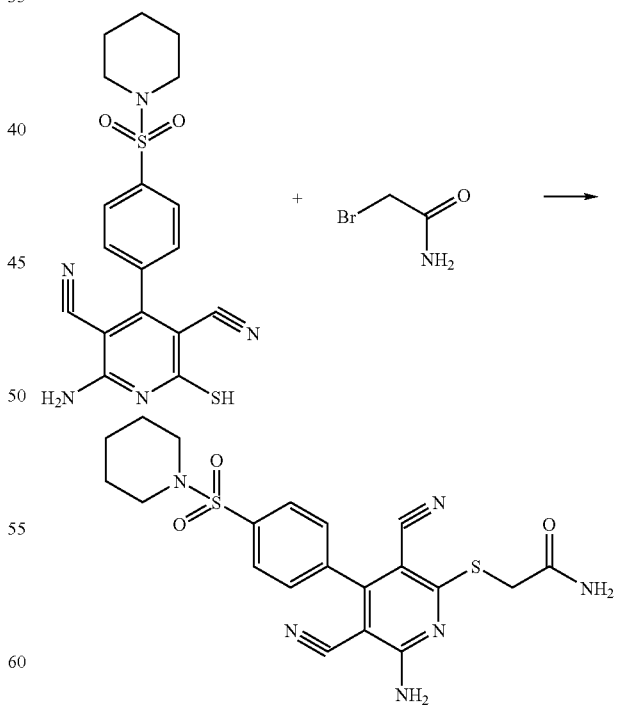

82 mg (0.164 mmol) of 2-amino-4-{4-(piperidinosulfonyl)phenyl}-6-sulfanyl-3,5-pyridinedicarbonitrile N-methylmorpholinium salt together with 53.5 mg (0.246 mmol) of bromoacetamide and 55 mg (0.65 mmol) of $NaHCO_3$ are stirred in 0.5 ml of DMF overnight. After filtration, the reaction solution is purified by preparative HPLC.

HPLC Conditions:
Column: GROM-SIL 120 ODS 4 HE 5µ 50×20 mm
Precolumn: GROM-SIL ODS 4 HE 15µ 10×20 mm
Wavelength: 220 mm
Flow rate: 25 ml/min
Gradient:
A=acetonitrile+0.1% trifluoroacetic acid
B=water+0.1% trifluoroacetic acid
0 min: 10%; 1.75 min. 10% A; 5.5 min. 90% A; 8 min. 90% A;
8.1 min. 10% A; 9 min. 10% A
Injection volume: 400 µl of DMF solution
Yield: 42.8 mg (57.2% of theory) of product
NMR [400 MHz, DMSO-$d_6$]: 1.4 m (2H), 1.6 m (4H), 3.0 tr (4H), 3.9 s (2H), 7.25 s (1H), 7.5 s (1H), 7.8 d (2H), 7.9 d (2H), 8.1 s broad (2H)

Example 16

2-({6-Amino-3,5-dicyano-4-[4-(morpholinosulfonyl)phenyl]-2-pyridinyl}-sulfanyl)acetamide

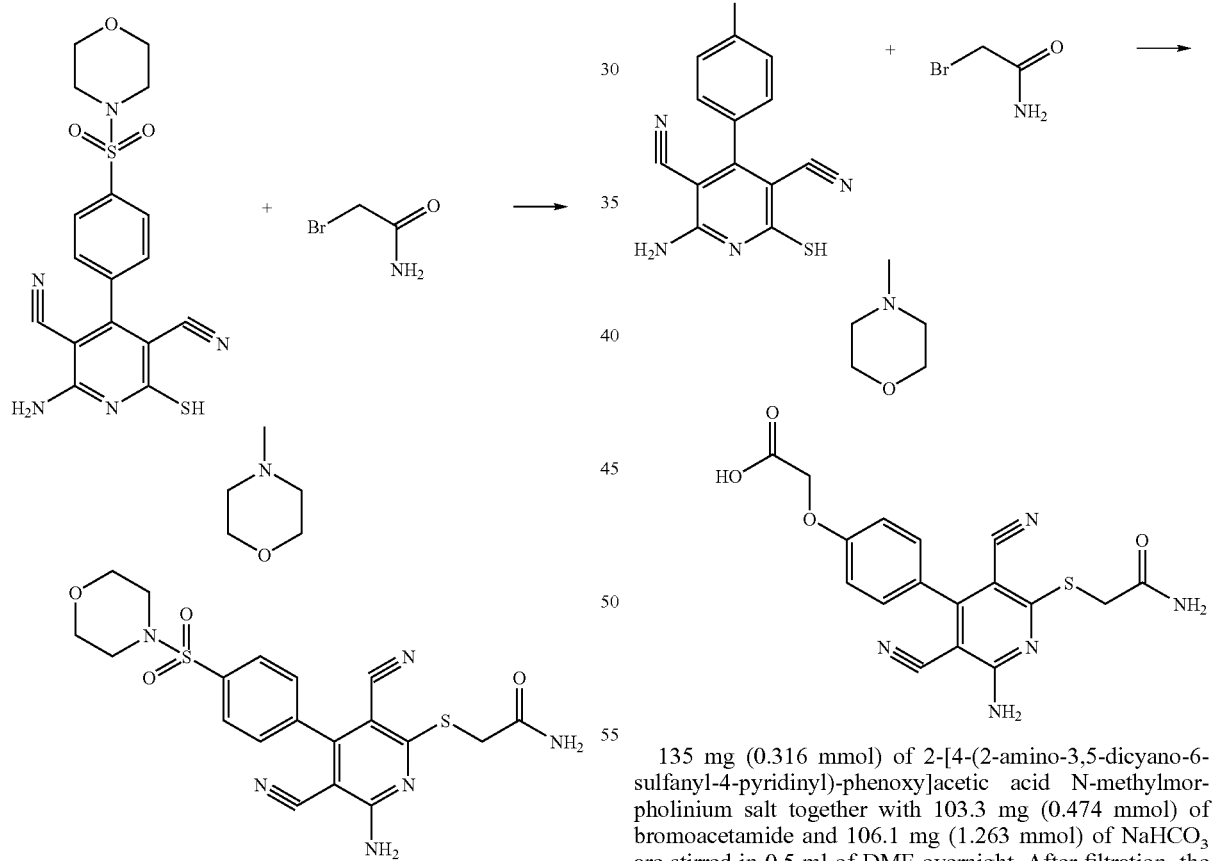

90 mg (0.179 mmol) of 2-amino-4-{4-(morpholinosulfonyl)phenyl}-6-sulfanyl-3,5-pyridinedicarbonitrile N-methylmorpholinium salt together with 58.5 mg (0.269 mmol) of bromoacetamide and 60 mg (0.71 mmol) of NaHCO$_3$ are stirred in 0.5 ml of DMF overnight. After filtration, the reaction solution is purified by preparative HPLC.

HPLC Conditions:
Column: GROM-SIL 120 ODS 4 HE 5µ 50×20 mm
Precolumn: GROM-SIL ODS 4 HE 15µ 10×20 mm
Wavelength: 220 mm
Flow rate: 25 ml/min
Gradient:
A=acetonitrile+0.1% trifluoroacetic acid
B=water+0.1% trifluoroacetic acid
0 min: 10%; 1.75 min. 10% A; 5.5 min. 90% A; 8 min. 90% A;
8.1 min. 10% A; 9 min. 10% A
Injection volume: 400 µl of DMF solution
Yield: 43.7 mg (53.2% of theory) of product
NMR[400 MHz, DMSO-$d_6$]: 2.9 tr (4H), 3.65 tr (4H), 3.9 s (2H), 7.25 s (1H), 7.5 s (1H), 7.85 d (2H), 7.95 d (2H), 8.15 s broad (2H)

Example 17

2-(4-{2-Amino-6-[(2-amino-2-oxoethyl)sulfanyl]-3,5-dicyano-4-pyridinyl}-phenoxy)acetic acid

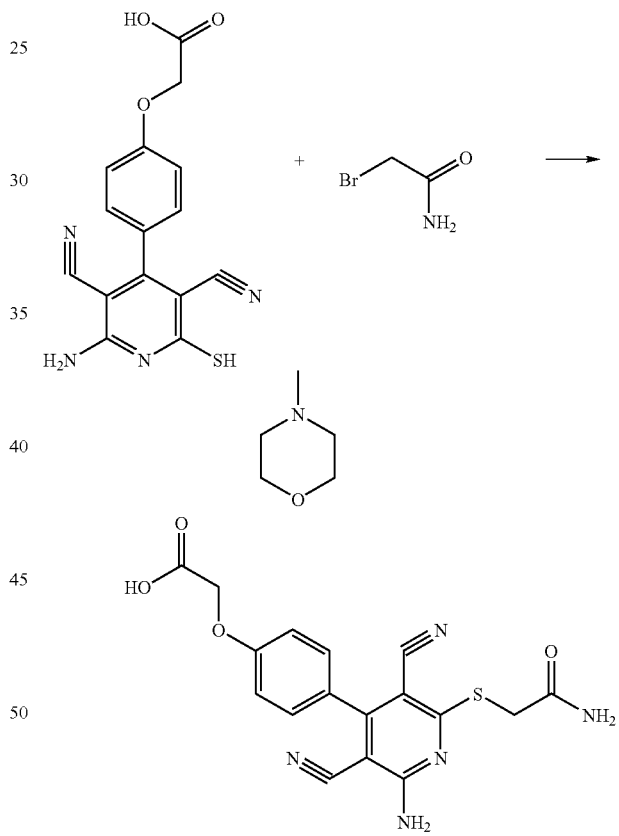

135 mg (0.316 mmol) of 2-[4-(2-amino-3,5-dicyano-6-sulfanyl-4-pyridinyl)-phenoxy]acetic acid N-methylmorpholinium salt together with 103.3 mg (0.474 mmol) of bromoacetamide and 106.1 mg (1.263 mmol) of NaHCO$_3$ are stirred in 0.5 ml of DMF overnight. After filtration, the reaction solution is prepurified by preparative HPLC. The isolated fraction is reconcentrated under reduced pressure and the residue is purified by preparative thin-layer chromatography.

Yield: 14 mg (11.6% of theory) of product
Mass spectrum: molecular mass calculated: 383, found [M+Na]$^+$=406.2

Example 18

4-{2-Amino-6-[(2-amino-2-oxoethyl)sulfanyl]-3,5-dicyano-4-pyridinyl}-benzoic acid

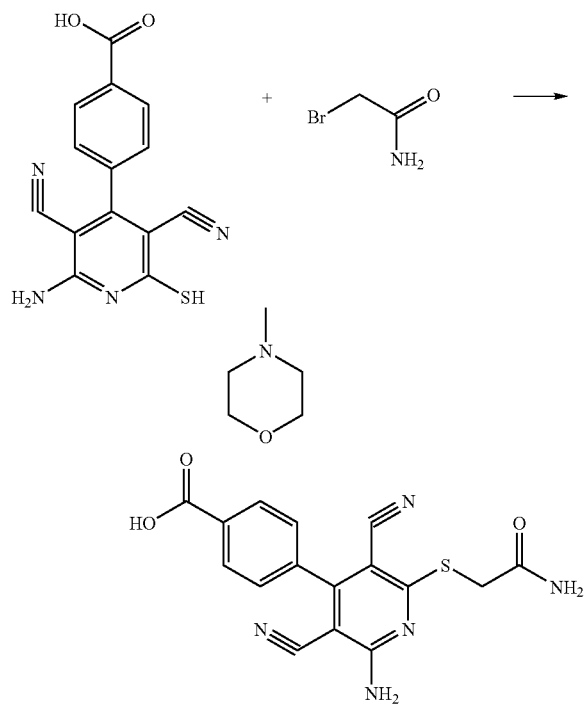

72 mg (0.18 mmol) of 2-[4-(2-amino-3,5-dicyano-6-sulfanyl-4-pyridinyl)benzoic acid N-methylmorpholinium salt together with 59.2 mg (0.27 mmol) of bromoacetamide and 60.9 mg (0.72 mmol) of NaHCO$_3$ are stirred in 0.5 ml of DMF overnight. After filtration, the reaction solution is prepurified by preparative HPLC. The isolated fraction is reconcentrated under reduced pressure and the residue is purified by preparative thin-layer chromatography.

Yield: 11 mg (17.2% of theory) of product

Mass spectrum: molecular mass calculated: 353, found [M+H]$^+$=353.9

Example 19

Methyl 4-{2-amino-6-[(2-amino-2-oxoethyl)sulfanyl]-3,5-dicyano-4-pyridinyl}-benzoate

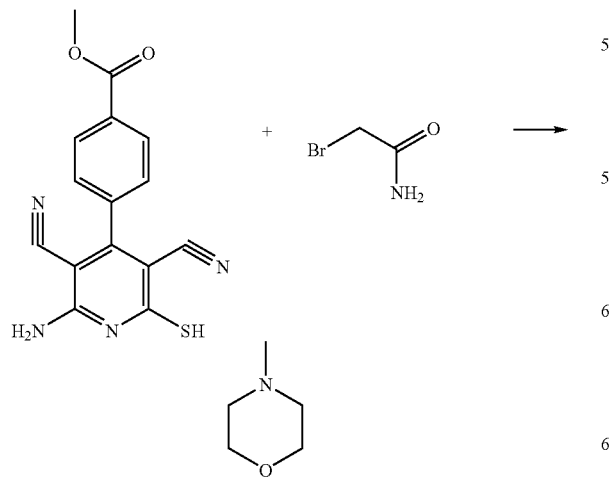

-continued

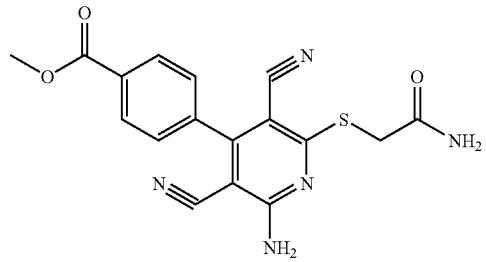

89 mg (0.216 mmol) of methyl 4-(2-amino-3,5-dicyano-6-sulfanyl-4-pyridinyl)-benzoate N-methylmorpholinium salt together with 70.7 mg (0.324 mmol) of bromoacetamide and 72.7 mg (0.86 mmol) of NaHCO$_3$ are stirred in 0.5 ml of DMF overnight. After filtration, the reaction solution is purified by preparative HPLC.

HPLC Conditions:
Column: GROM-SIL 120 ODS 4 HE 5μ 50×20 mm
Precolumn: GROM-SIL ODS 4 HE 15μ 10×20 mm
Wavelength: 220 mm
Flow rate: 25 m/min
Gradient:
A=acetonitrile+0.1% trifluoroacetic acid
B=water+0.1% trifluoroacetic acid
0 min: 10%; 1.75 min. 10% A; 5.5 min. 90% A; 8 min. 90% A;
8.1 min. 10% A; 9 min. 10% A
Injection volume: 400 μl of DMF solution
Yield: 40.4 mg (50.8% of theory) of product
NMR [400 MHz, DMSO-d$_6$]: 3.9 s (2H), 7.25 s (1H), 7.5 s (1H), 7.7 d (2H), 8.1 d (2H), 8.1 s broad (2H)

Example 20

2-({4-[4-(Acetylamino)phenyl]-6-amino-3,5-dicyano-2-pyridinyl}sulfanyl)-acetamide

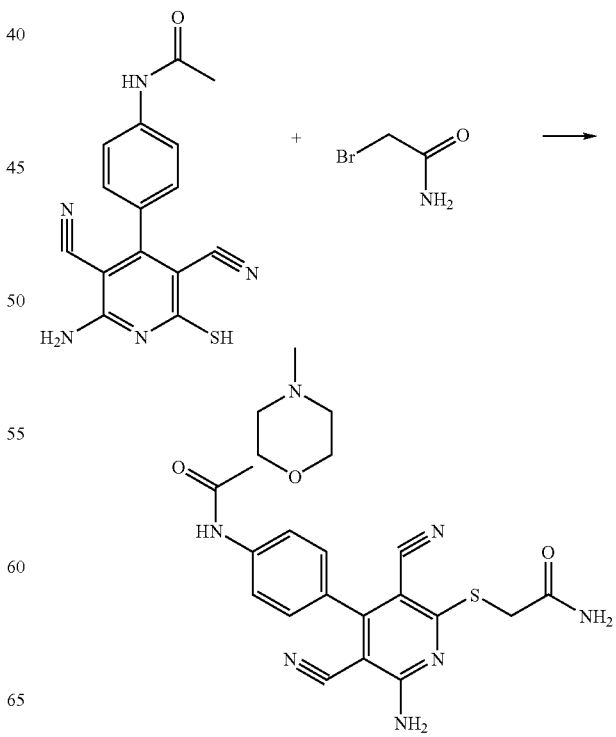

44 mg (0.11 mmol) of N-[4-(2-amino-3,5-dicyano-6-sulfanyl-4-pyridinyl)phenyl]-acetamide N-methylmorpholinium salt together with 35 mg (0.16 mmol) of bromoacetamide and 36 mg (0.43 mmol) of NaHCO₃ are stirred in 0.5 ml of DMF overnight. After filtration, the reaction solution was purified by preparative HPLC.

HPLC Conditions:
  Column: GROM-SIL 120 ODS 4 HE 5µ 50×20 mm
  Precolumn: GROM-SIL ODS 4 HE 15µ 10×20 mm
  Wavelength: 220 mm
  Flow rate: 25 ml/min
  Gradient:
  A=acetonitrile+0.1% trifluoroacetic acid
  B=water+0.1% trifluoroacetic acid
  0 min: 10%; 1.75 min. 10% A; 5.5 min. 90% A; 8 min. 90% A;
  8.1 min. 10% A; 9 min. 10% A
  Injection volume: 400 µl of DMF solution
  Yield: 18.3 mg (46.6% of theory) of product
  NMR [400 MHz, DMSO-$d_6$]: 2.1 s (3H), 3.9 s (2H), 7.25 s (1H), 7.5 d (3H), 7.7 d (2H), 8.0 s broad (2H), 10.25 s (1H)

Example 21

2-Amino-6-[(2-hydroxyethyl)sulfanyl]-4-(4-hydroxyphenyl)-3,5-pyridinedicarbonitrile

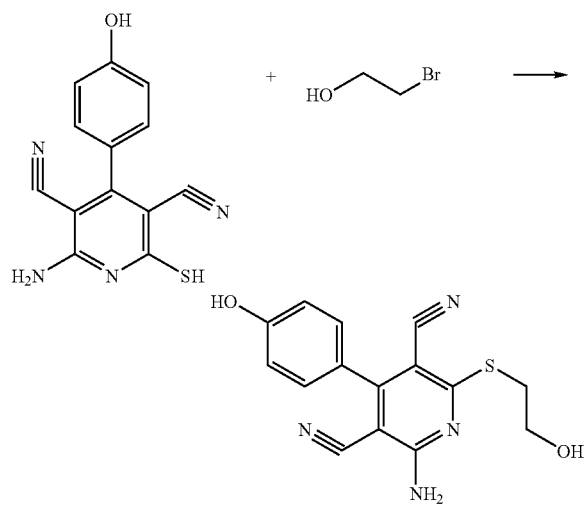

26.8 mg (0.1 mmol) of 2-amino-4-(4-hydroxyphenyl)-6-sulfanyl-3,5-pyridinedicarbonitrile are dissolved in 0.2 ml of dimethylformamide. 20 mg (0.238 mmol) of solid sodium bicarbonate are added, followed by a solution of 18.74 mg (0.15 mmol) of 2-bromoethanol in 0.06 ml of dimethylformamide. The reaction mixture is shaken overnight and, after filtration, purified by preparative HPLC.

HPLC Conditions:
  Column: GROM-SIL 120 ODS 4 HE 5µ 50×20 mm
  Precolumn: GROM-SIL ODS 4 HE 15µ 10×20 mm
  Wavelength: 220 nm
  Flow rate: 25 ml/min
  Gradient:
  A=acetonitrile+0.1% trifluoroacetic acid
  B=water+0.1% trifluoroacetic acid
  0 min: 10%; 1.75 min. 10% A; 5.5 min. 90% A; 8 min. 90% A;
  8.1 min. 10% A; 9 min. 10% A
  Injection volume: 300 µl of DMSO solution
  Retention time: 3.97 min Yield: 14.1 mg (45.1% of theory)
Mass spectrum: molecular mass calculated: 312, found [M+H]⁺=313

Example 22

1. Step:

N-[4-(2,2-Dicyanovinyl)phenyl]acetamide

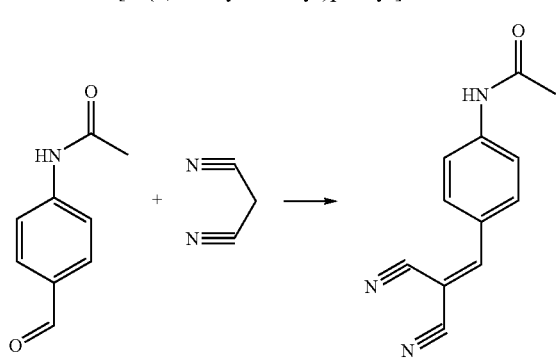

32.6 g (0.2 mol) of 4-acetaminobenzaldehyde and 13.74 g (0.208 mol) of malononitrile are initially charged in 140 ml of ethanol, and 24 drops of piperidine are added. The mixture is stirred at reflux for 30 min. After cooling, the crystals are filtered off with suction and dried.
Yield: 38.6 g (90.6% of theory) of product
Mass spectrum: molecular mass calculated: 211, found [M+H]⁺=212

2. Step

N-{4-[2-Amino-3,5-dicyano-6-(phenylsulfanyl)-4-pyridinyl]phenyl}acetamide

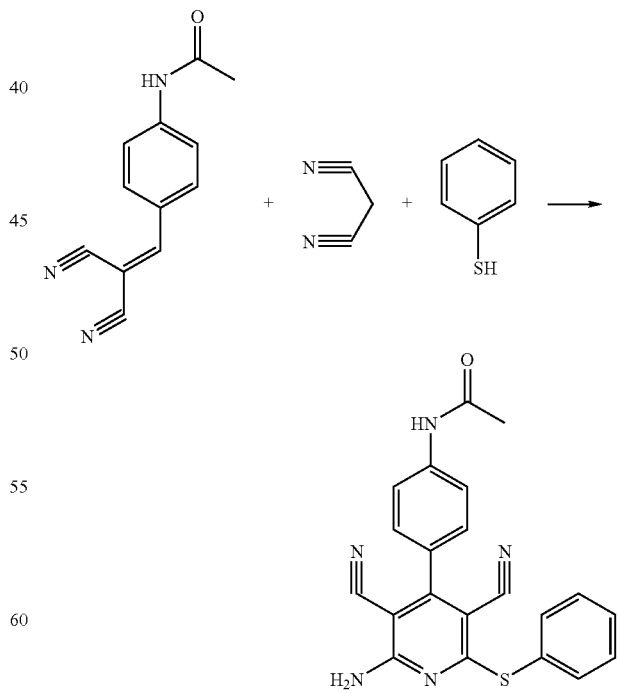

19 g (0.09 mol) of N-[4-(2,2-dicyanovinyl)phenyl]acetamide, 5.95 g (0.09 mol) of malononitrile and 9.91 g (0.09 mol) of thiophenol are initially charged in 120 ml of ethanol, and 0.4 ml of triethylamine are added. The mixture is stirred at reflux for 2 h, during which the product crystallizes. After cooling, the product is filtered off with suction and dried under reduced pressure.

Yield: 10.25 g (29.6% of theory) of product

Mass spectrum: molecular mass calculated: 385, found [M+H]$^+$=386

3. Step

N-[4-(2-Amino-3,5-dicyano-6-sulfanyl-4-pyridinyl)phenyl]acetamide

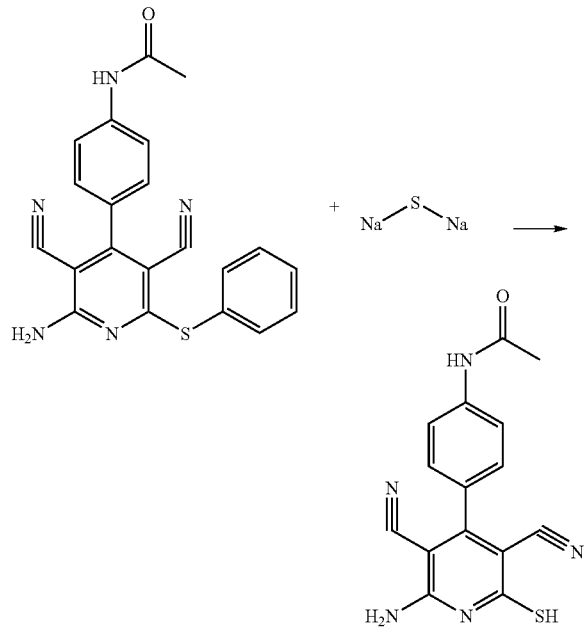

Under argon, 1.16 g (3 mmol) of N-{4-[2-amino-3,5-dicyano-6-(phenylsulfanyl)-4-pyridinyl]phenyl}-acetamide are dissolved in 10 ml of DMF, 0.78 g (10 mmol) of sodium sulfide are added and the mixture is stirred at 80° C. for 2 h. 20 ml of 1N HCl are then added and the resulting crystals are filtered off with suction and dried under reduced pressure.

Yield: 428 mg (46.1% of theory) of product

Mass spectrum: molecular mass calculated: 309, found [M+H]$^+$=310.1

4. Step

2-[({4-[4-(Acetylamino)phenyl]-6-amino-3,5-dicyano-2-pyridinyl}sulfanyl)-methyl]-1H-imidazol-1-ium trifluoracetate

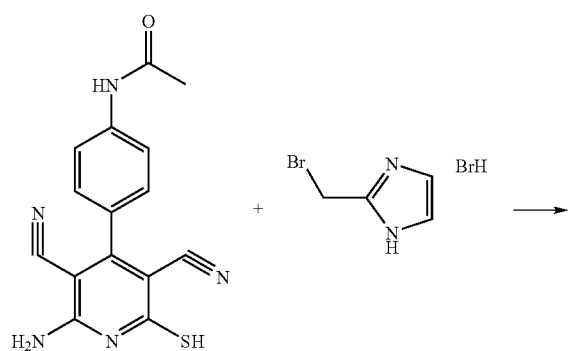

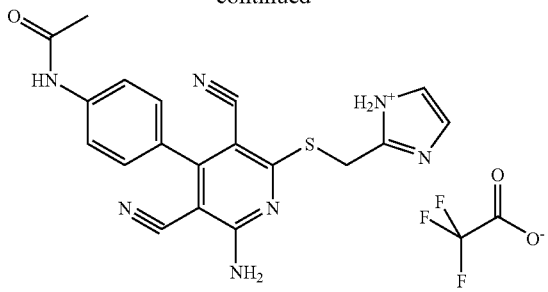

309 mg (1 mmol) of N-[4-(2-amino-3,5-dicyano-6-sulfanyl-4-pyridinyl)phenyl]-acetamide, 241 mg (1 mmol) of 2-(bromomethyl)-1H-imidazole hydrobromide and 336 mg (4 mmol) of NaHCO$_3$ in 2 ml of DMF are stirred at RT. After 2 h, 4 to 5 ml of water are added and the beige crystals are filtered off with suction and dried under reduced pressure. The crystals (310 mg) are dissolved in DMSO and purified by prep. HPLC using 9 injections. The corresponding fraction is concentrated under reduced pressure and the crystalline residue is suspended in water, filtered off with suction and dried under reduced pressure.

HPLC Conditions:

Column: Kromasil 100 C18 5 µm 50×20 mm

Precolumn: GROM-SIL ODS 4 HE 15µ 10×20 mm

Wavelength: 220 nm

Flow rate: 25 ml/min

Gradient:

A=acetonitrile+0.1% trifluoroacetic acid

B=water+0.1% trifluoroacetic acid 0 min: 10% A; 2 min. 10% A; 6 min. 90% A; 7 min. 90% A;

7.1 min. 10% A; 8 min. 10% A

Injection volume: 500 µl of DMSO solution

Retention time: 3.6 min

Yield: 234 mg (60% of theory) of product

Mass spectrum: molecular mass calculated: 389, found [M+H]$^+$=390.1

$^1$H-NMR (300 MHz, DMSO-d$_6$): δ=2.1 s (3H), 4.7 s (1H), 7.4 d (2H), 7.55 s (1H), 7.7 d (2H), 8.1 s broad (2H), 10.25 s (1H), 14.2 s broad (1H)

The compounds listed in the tables below (examples A 1 to A 377, A 378 to A 413 and B 1 to B 375) were prepared analogously to the procedures given above. Identity and purity of the compounds was demonstrated by LC-MS.

The compounds of examples A 1 to A 413 were either isolated as crystals or, if they did not crystallize directly from the reaction solution, purified by preparative HPLC.

The compounds of examples B 1 to B 375 were prepared on a 10 µmol scale, analogously to the procedures above. These compounds were purified and identified by a preparative HPLC-MS system.

In the tables below, structures having a group —N— are in each case understood to contain a group —NH— and structures having a group —N are in each case to be understood as containing a group —NH$_2$.

| Ex. No. | Product | Starting material A | Starting material B | Molecular mass calculated | [M + H]+ found | Yield (% of theory) |
|---|---|---|---|---|---|---|
| A1 | (structure) | bromoacetamide | (pyridine structure) | 325 | 326 | 57.5 |
| A2 | (structure) | bromoacetic acid | (pyridine structure) | 326 | 327 | 7.0 |
| A3 | (structure) | 1-bromo-2-hydroxypropane | (pyridine structure) | 326 | 327 | 52.7 |

| Ex. No. | Product | Starting material A | Starting material B | Molecular mass calculated | [M + H]+ found | Yield (% of theory) |
|---|---|---|---|---|---|---|
| A4 | (structure) | (structure) | (structure) | 339 | 340 | 67.5 |
| A5 | (structure) | (structure) | (structure) | 340 | 341 | 60.8 |
| A6 | (structure) | (structure) | (structure) | 354 | 355 | 53.6 |

-continued

| Ex. No. | Product | Starting material A | Starting material B | Molecular mass calculated | [M + H]+ found | Yield (% of theory) |
|---|---|---|---|---|---|---|
| A7 | | | | 366 | 367 | 30.0 |
| A8 | | | | 386 | 387 | 57.2 |
| A9 | | | | 394 | 395 | 12.2 |

-continued

| Ex. No. | Product | Starting material A | Starting material B | Molecular mass calculated | [M + H]+ found | Yield (% of theory) |
|---|---|---|---|---|---|---|
| A10 | (4-fluorophenyl ketone thioether pyridine product) | 2-bromo-1-(4-fluorophenyl)ethanone | 2-amino-4-(4-hydroxyphenyl)-6-mercaptopyridine-3,5-dicarbonitrile | 404 | 405 | 39.3 |
| A11 | (N-phenyl propanamide thioether pyridine product) | 2-bromo-N-phenylpropanamide | 2-amino-4-(4-hydroxyphenyl)-6-mercaptopyridine-3,5-dicarbonitrile | 415 | 416 | 58.2 |
| A12 | (N-(2,4-dimethylphenyl) acetamide thioether pyridine product) | 2-bromo-N-(2,4-dimethylphenyl)acetamide | 2-amino-4-(4-hydroxyphenyl)-6-mercaptopyridine-3,5-dicarbonitrile | 430 | 431 | 25.1 |

-continued

| Ex. No. | Product | Starting material A | Starting material B | Molecular mass calculated | [M + H]+ found | Yield (% of theory) |
|---|---|---|---|---|---|---|
| A13 | | | | 446 | 447 | 28.1 |
| A14 | | | | 456 | 457 | 29.6 |
| A15 | | | | 470 | 471 | 62.2 |

-continued

| Ex. No. | Product | Starting material A | Starting material B | Molecular mass calculated | [M + H]+ found | Yield (% of theory) |
|---|---|---|---|---|---|---|
| A16 | | | | 342 | 343 | 54.0 |
| A17 | | | | 352 | 353 | 73.8 |
| A18 | | | | 402 | 403 | 65.6 |

-continued

| Ex. No. | Product | Starting material A | Starting material B | Molecular mass calculated | [M + H]+ found | Yield (% of theory) |
|---|---|---|---|---|---|---|
| A19 | (product structure) | (structure) | (structure) | 416 | 417 | 51.9 |
| A20 | (product structure) | (structure) | (structure) | 341 | 342 | 29.7 |
| A21 | (product structure) | (structure) | (structure) | 354 | 355 | 84.4 |

| Ex. No. | Product | Starting material A | Starting material B | Molecular mass calculated | [M + H]+ found | Yield (% of theory) |
|---|---|---|---|---|---|---|
| A22 | | | | 355 | 356 | 10.0 |
| A23 | | | | 355 | 356 | 35.2 |
| A24 | | | | 368 | 369 | 77.1 |

-continued

| Ex. No. | Product | Starting material A | Starting material B | Molecular mass calculated | [M + H]+ found | Yield (% of theory) |
|---|---|---|---|---|---|---|
| A25 | (structure) | methyl bromoacetate | (nitrophenyl pyridine thiol) | 369 | 370 | 70.9 |
| A26 | (structure) | methyl 2-bromopropanoate | (nitrophenyl pyridine thiol) | 383 | 384 | 68.1 |
| A27 | (structure) | 1-bromo-3,3-dimethylbutan-2-one | (nitrophenyl pyridine thiol) | 395 | 396 | 60.2 |

-continued

| Ex. No. | Product | Starting material A | Starting material B | Molecular mass calculated | [M + H]+ found | Yield (% of theory) |
|---|---|---|---|---|---|---|
| A28 | | | | 415 | 416 | 58.0 |
| A29 | | | | 423 | 424 | 31.2 |
| A30 | | | | 433 | 434 | 36.2 |

-continued

| Ex. No. | Product | Starting material A | Starting material B | Molecular mass calculated | [M + H]+ found | Yield (% of theory) |
|---|---|---|---|---|---|---|
| A31 | | | | 444 | 445 | 51.1 |
| A32 | | | | 459 | 460 | 46.7 |

| Ex. No. | Product | Starting material A | Starting material B | Molecular mass calculated | [M + H]+ found | Yield (% of theory) |
|---|---|---|---|---|---|---|
| A33 | 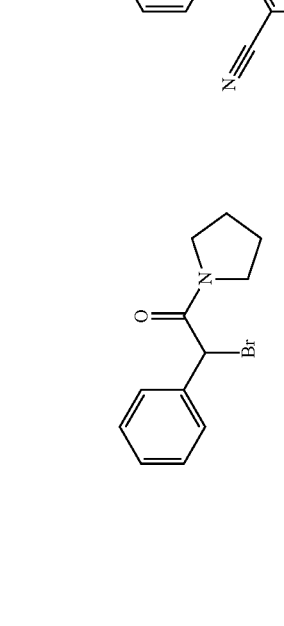 | 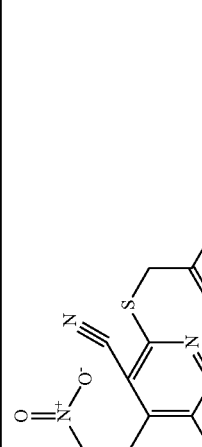 | 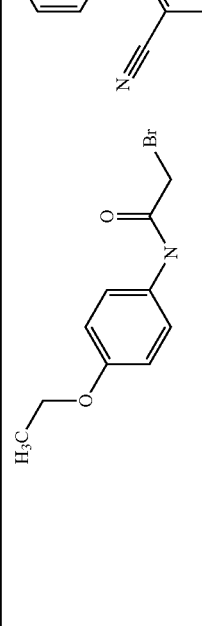 | 475 | 476 | 49.7 |
| A34 | 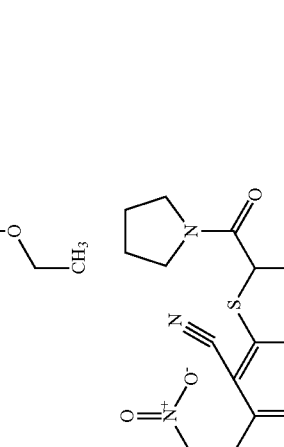 | 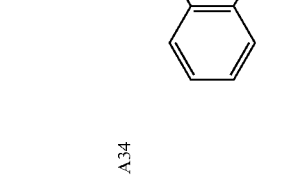 | 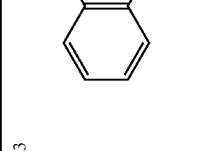 | 485 | 486 | 47.1 |

-continued

| Ex. No. | Product | Starting material A | Starting material B | Molecular mass calculated | [M + H]+ found | Yield (% of theory) |
|---|---|---|---|---|---|---|
| A35 | | | | 499 | 500 | 64.0 |
| A36 | | | | 507 | 508 | 37.5 |
| A37 | | | | 521 | 522 | 61.5 |

-continued

| Ex. No. | Product | Starting material A | Starting material B | Molecular mass calculated | [M + H]+ found | Yield (% of theory) |
|---|---|---|---|---|---|---|
| A38 | (structure) | (3-bromo-1,2-propanediol) | (structure) | 371 | 372 | 63.8 |
| A39 | (structure) | (3-bromo-dihydrofuran-2(3H)-one) | (structure) | 381 | 382 | 50.3 |
| A40 | (structure) | (α-bromophenylacetic acid) | (structure) | 431 | 432 | 40.8 |

| Ex. No. | Product | Starting material A | Starting material B | Molecular mass calculated | [M + H]+ found | Yield (% of theory) |
|---|---|---|---|---|---|---|
| A41 | | | | 445 | 446 | 71.9 |
| A42 | | | | 445 | 446 | 32.6 |
| A43 | | | | 312 | 313 | 60.8 |

-continued

| Ex. No. | Product | Starting material A | Starting material B | Molecular mass calculated | [M + H]+ found | Yield (% of theory) |
|---|---|---|---|---|---|---|
| A44 | (3-OH-phenyl pyridine with S-CH2-C(O)NH2, CN, CN, NH2) | BrCH2C(O)NH2 | (3-OH-phenyl pyridine with CN, CN, SH, NH2) | 325 | 326 | 78.4 |
| A45 | (3-OH-phenyl pyridine with S-CH2-COOH, CN, CN, NH2) | BrCH2COOH | (3-OH-phenyl pyridine with CN, CN, SH, NH2) | 326 | 327 | 13.9 |
| A46 | (3-OH-phenyl pyridine with S-CH2-CH(OH)CH3, CN, CN, NH2) | BrCH2CH(OH)CH3 | (3-OH-phenyl pyridine with CN, CN, SH, NH2) | 326 | 327 | 17.8 |

-continued

| Ex. No. | Product | Starting material A | Starting material B | Molecular mass calculated | [M + H]+ found | Yield (% of theory) |
|---|---|---|---|---|---|---|
| A47 | | | | 339 | 340 | 89.6 |
| A48 | | | | 340 | 341 | 77.6 |
| A49 | | | | 354 | 355 | 56.2 |

| Ex. No. | Product | Starting material A | Starting material B | Molecular mass calculated | [M + H]+ found | Yield (% of theory) |
|---|---|---|---|---|---|---|
| A50 | (product structure) | (bromo ketone with t-Bu) | (pyridine SH/NH2 with 3-hydroxyphenyl) | 366 | 367 | 47.5 |
| A51 | (product structure) | 2-bromoacetophenone | (pyridine SH/NH2 with 3-hydroxyphenyl) | 386 | 387 | 36.5 |
| A52 | (product structure) | (bromoacetyl imidazolidinone) | (pyridine SH/NH2 with 3-hydroxyphenyl) | 394 | 395 | 20.5 |

| Ex. No. | Product | Starting material A | Starting material B | Molecular mass calculated | [M + H]+ found | Yield (% of theory) |
|---|---|---|---|---|---|---|
| A53 | | | | 404 | 405 | 58.8 |
| A54 | | | | 415 | 416 | 18.3 |
| A55 | | | | 430 | 431 | 29.8 |

-continued
| Ex. No. | Product | Starting material A | Starting material B | Molecular mass calculated | [M + H]+ found | Yield (% of theory) |
|---|---|---|---|---|---|---|
| A56 | 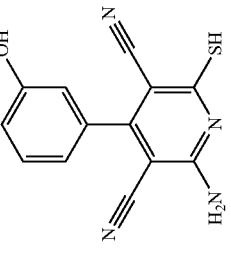 | 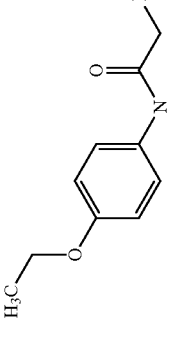 | 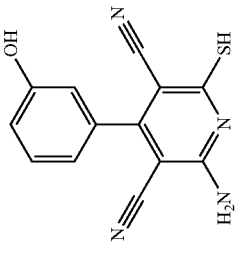 | 446 | 447 | 42.2 |
| A57 | 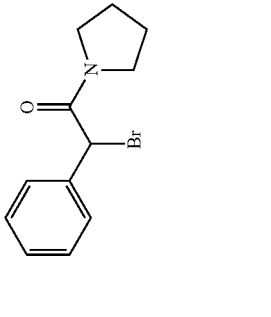 | 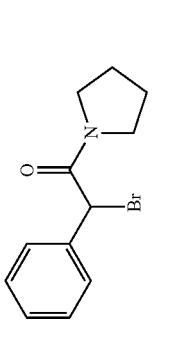 | 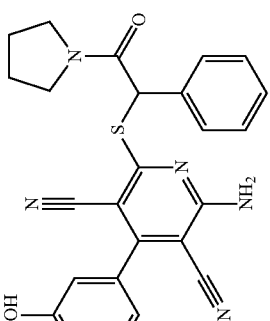 | 456 | 457 | 9.2 |

-continued
| Ex. No. | Product | Starting material A | Starting material B | Molecular mass calculated | [M + H]+ found | Yield (% of theory) |
|---|---|---|---|---|---|---|
| A58 |  | 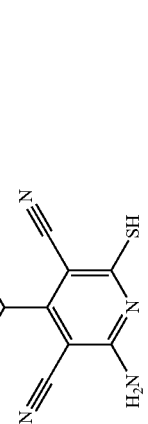 | 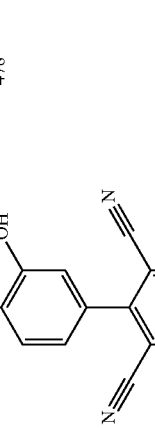 | 478 | 479 | 54.2 |
| A59 |  |  |  | 492 | 493 | 66.3 |
| A60 |  | 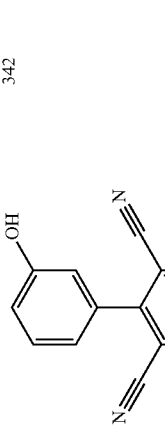 | 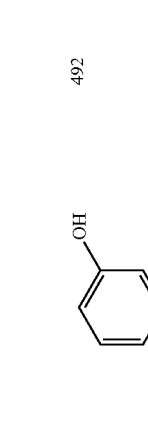 | 342 | 343 | 73.6 |

| Ex. No. | Product | Starting material A | Starting material B | Molecular mass calculated | [M + H]+ found | Yield (% of theory) |
|---|---|---|---|---|---|---|
| A61 | (structure with thiolactone-S-pyridine, OH-phenyl, CN, NH2) | 3-bromo-dihydrofuran-2-one | 6-amino-4-(3-hydroxyphenyl)-2-mercapto-3,5-dicyanopyridine | 352 | 353 | 68.1 |
| A62 | (structure with phenyl-CH(COOH)-S-pyridine, OH-phenyl, CN, NH2) | 2-bromo-2-phenylacetic acid | 6-amino-4-(3-hydroxyphenyl)-2-mercapto-3,5-dicyanopyridine | 402 | 403 | 41.2 |
| A63 | (structure with phenyl-CH(COOCH3)-S-pyridine, OH-phenyl, CN, NH2) | methyl 2-bromo-2-phenylacetate | 6-amino-4-(3-hydroxyphenyl)-2-mercapto-3,5-dicyanopyridine | 416 | 417 | 52.1 |

-continued

| Ex. No. | Product | Starting material A | Starting material B | Molecular mass calculated | [M + H]+ found | Yield (% of theory) |
|---|---|---|---|---|---|---|
| A64 | (3-hydroxyphenyl pyridine product with S-CH2-C(O)-O-CH2-phenyl) | benzyl bromoacetate | 4-(3-hydroxyphenyl)-2-mercapto-6-amino-3,5-dicyanopyridine | 416 | 417 | 52.6 |
| A65 | (4-fluorophenyl pyridine product with S-CH2CH2-OH) | 2-bromoethanol | 4-(4-fluorophenyl)-2-mercapto-6-amino-3,5-dicyanopyridine | 314 | 315 | 62.7 |
| A66 | (4-fluorophenyl pyridine product with S-CH2-C(O)-NH2) | 2-bromoacetamide | 4-(4-fluorophenyl)-2-mercapto-6-amino-3,5-dicyanopyridine | 327 | 328 | 58.0 |

-continued

| Ex. No. | Product | Starting material A | Starting material B | Molecular mass calculated | [M + H]+ found | Yield (% of theory) |
|---|---|---|---|---|---|---|
| A67 | (product structure) | bromoacetic acid | (pyridine-SH starting material) | 328 | 329 | 17.1 |
| A68 | (product structure) | 1-bromo-2-propanol | (pyridine-SH starting material) | 328 | 329 | 53.9 |
| A69 | (product structure) | 2-bromopropanamide | (pyridine-SH starting material) | 341 | 342 | 57.7 |

| Ex. No. | Product | Starting material A | Starting material B | Molecular mass calculated | [M + H]+ found | Yield (% of theory) |
|---|---|---|---|---|---|---|
| A70 | (product structure) | methyl bromoacetate | (pyridine-SH structure) | 342 | 343 | 35.6 |
| A71 | (product structure) | methyl 2-bromopropanoate | (pyridine-SH structure) | 356 | 357 | 49.7 |
| A72 | (product structure) | benzyl bromide | (pyridine-SH structure) | 360 | 361 | 43.3 |

-continued

| Ex. No. | Product | Starting material A | Starting material B | Molecular mass calculated | [M + H]+ found | Yield (% of theory) |
|---|---|---|---|---|---|---|
| A73 | (product structure) | (structure) | (structure) | 368 | 369 | 14.7 |
| A74 | (product structure) | (structure) | (structure) | 388 | 389 | 17.5 |
| A75 | (product structure) | (structure) | (structure) | 417 | 418 | 31.1 |

-continued

| Ex. No. | Product | Starting material A | Starting material B | Molecular mass calculated | [M + H]+ found | Yield (% of theory) |
|---|---|---|---|---|---|---|
| A76 | (pyrrolidine amide, phenyl, thio-pyridine with 4-F-phenyl, two CN, NH2) | 2-bromo-2-phenyl-1-(pyrrolidin-1-yl)ethanone | 6-amino-4-(4-fluorophenyl)-2-mercapto-pyridine-3,5-dicarbonitrile | 458 | 459 | 19.5 |
| A77 | (piperidine amide, phenyl, thio-pyridine with 4-F-phenyl, two CN, NH2) | 2-bromo-2-phenyl-1-(piperidin-1-yl)ethanone | 6-amino-4-(4-fluorophenyl)-2-mercapto-pyridine-3,5-dicarbonitrile | 472 | 473 | 41.8 |
| A78 | (4-Cl-phenyl-CH(CH3)-NH-C(O)-CH(CH3)-S-pyridine derivative) | N-(1-(4-chlorophenyl)ethyl)-2-bromopropanamide | 6-amino-4-(4-fluorophenyl)-2-mercapto-pyridine-3,5-dicarbonitrile | 480 | 481 | 32.9 |

-continued

| Ex. No. | Product | Starting material A | Starting material B | Molecular mass calculated | [M + H]+ found | Yield (% of theory) |
|---|---|---|---|---|---|---|
| A79 | (structure) | (structure) | (structure) | 494 | 495 | 29.0 |
| A80 | (structure) | (structure) | (structure) | 344 | 345 | 45.6 |
| A81 | (structure) | (structure) | (structure) | 354 | 355 | 37.2 |

-continued

| Ex. No. | Product | Starting material A | Starting material B | Molecular mass calculated | [M + H]+ found | Yield (% of theory) |
|---|---|---|---|---|---|---|
| A82 | (product structure) | 2-bromo-2-phenylacetic acid | (pyridine-SH starting material) | 404 | 405 | 37.6 |
| A83 | (product structure) | methyl 2-bromo-2-phenylacetate | (pyridine-SH starting material) | 418 | 419 | 63.3 |
| A84 | (product structure) | benzyl bromoacetate | (pyridine-SH starting material) | 418 | 419 | 21.5 |

-continued

| Ex. No. | Product | Starting material A | Starting material B | Molecular mass calculated | [M + H]+ found | Yield (% of theory) |
|---|---|---|---|---|---|---|
| A85 | *structure* | HO-CH2CH2-Br | *structure* | 331 | 332 | 71.3 |
| A86 | *structure* | H2N-C(O)-CH2-Br | *structure* | 344 | 345 | 66.9 |
| A87 | *structure* | H3C-CH(OH)-CH2-Br | *structure* | 345 | 346 | 76.3 |

-continued

| Ex. No. | Product | Starting material A | Starting material B | Molecular mass calculated | [M + H]+ found | Yield (% of theory) |
|---|---|---|---|---|---|---|
| A88 | | | | 358 | 359 | 83.8 |
| A89 | | | | 359 | 360 | 89.7 |
| A90 | | | | 373 | 374 | 70.5 |

| Ex. No. | Product | Starting material A | Starting material B | Molecular mass calculated | [M + H]+ found | Yield (% of theory) |
|---|---|---|---|---|---|---|
| A91 | (3-chlorophenyl/tert-butyl ketone thioether pyridine structure) | 1-bromo-3,3-dimethylbutan-2-one | 2-amino-4-(3-chlorophenyl)-3,5-dicyano-6-mercaptopyridine | 385 | 386 | 12.2 |
| A92 | (3-chlorophenyl/phenacyl thioether pyridine structure) | 2-bromoacetophenone | 2-amino-4-(3-chlorophenyl)-3,5-dicyano-6-mercaptopyridine | 405 | 406 | 84.0 |
| A93 | (3-chlorophenyl/imidazolidinone thioether pyridine structure) | 1-(bromoacetyl)-2-imidazolidinone | 2-amino-4-(3-chlorophenyl)-3,5-dicyano-6-mercaptopyridine | 413 | 414 | 12.1 |

| Ex. No. | Product | Starting material A | Starting material B | Molecular mass calculated | [M + H]+ found | Yield (% of theory) |
|---|---|---|---|---|---|---|
| A94 | | | | 423 | 424 | 23.6 |
| A95 | | | | 434 | 435 | 67.3 |
| A96 | | | | 488 | 489 | 67.4 |

-continued

| Ex. No. | Product | Starting material A | Starting material B | Molecular mass calculated | [M + H]+ found | Yield (% of theory) |
|---|---|---|---|---|---|---|
| A97 | (structure) | (structure) | (structure) | 496 | 497 | 90.2 |
| A98 | (structure) | (structure) | (structure) | 510 | 511 | 55.7 |
| A99 | (structure) | (structure) | (structure) | 361 | 362 | 103.1 |

-continued

| Ex. No. | Product | Starting material A | Starting material B | Molecular mass calculated | [M + H]+ found | Yield (% of theory) |
|---|---|---|---|---|---|---|
| A100 | | | | 371 | 372 | 48.3 |
| A101 | | | | 421 | 422 | 97.9 |
| A102 | | | | 435 | 436 | 51.7 |

| Ex. No. | Product | Starting material A | Starting material B | Molecular mass calculated | [M + H]+ found | Yield (% of theory) |
|---|---|---|---|---|---|---|
| A103 | | | | 435 | 436 | 63.7 |
| A104 | | | | 296 | 297 | 82.0 |
| A105 | | | | 309 | 310 | 75.6 |

| Ex. No. | Product | Starting material A | Starting material B | Molecular mass calculated | [M + H]+ found | Yield (% of theory) |
|---|---|---|---|---|---|---|
| A106 | | | | 310 | 311 | 72.5 |
| A107 | | | | 323 | 324 | 84.4 |
| A108 | | | | 324 | 325 | 67.8 |
| A109 | | | | 338 | 339 | 71.8 |

-continued

| Ex. No. | Product | Starting material A | Starting material B | Molecular mass calculated | [M + H]+ found | Yield (% of theory) |
|---|---|---|---|---|---|---|
| A110 | | | | 342 | 343 | 44.7 |
| A111 | | | | 350 | 351 | 18.5 |
| A112 | | | | 370 | 371 | 73.2 |

| Ex. No. | Product | Starting material A | Starting material B | Molecular mass calculated | [M + H]+ found | Yield (% of theory) |
|---|---|---|---|---|---|---|
| A113 | | | | 378 | 379 | 46.8 |
| A114 | | | | 388 | 389 | 91.4 |
| A115 | | | | 399 | 400 | 17.5 |

| Ex. No. | Product | Starting material A | Starting material B | Molecular mass calculated | [M + H]+ found | Yield (% of theory) |
|---|---|---|---|---|---|---|
| A116 | | | | 414 | 415 | 16.7 |
| A117 | | | | 430 | 431 | 31.4 |
| A118 | | | | 454 | 455 | 58.4 |

| Ex. No. | Product | Starting material A | Starting material B | Molecular mass calculated | [M + H]+ found | Yield (% of theory) |
|---|---|---|---|---|---|---|
| A119 | | | | 462 | 463 | 77.1 |
| A120 | | | | 476 | 477 | 13.0 |
| A121 | | | | 326 | 327 | 89.8 |

| Ex. No. | Product | Starting material A | Starting material B | Molecular mass calculated | [M + H]+ found | Yield (% of theory) |
|---|---|---|---|---|---|---|
| A122 | | | | 336 | 337 | 69.3 |
| A123 | | | | 386 | 387 | 73.2 |
| A124 | | | | 400 | 401 | 66.9 |

-continued

| Ex. No. | Product | Starting material A | Starting material B | Molecular mass calculated | [M + H]+ found | Yield (% of theory) |
|---|---|---|---|---|---|---|
| A125 | | | | 400 | 401 | 74.2 |
| A126 | | | | 331 | 332 | 72.6 |
| A127 | | | | 344 | 345 | 68.1 |

-continued

| Ex. No. | Product | Starting material A | Starting material B | Molecular mass calculated | [M + H]+ found | Yield (% of theory) |
|---|---|---|---|---|---|---|
| A128 | | | | 345 | 346 | 70.2 |
| A129 | | | | 358 | 359 | 72.4 |
| A130 | | | | 359 | 360 | 44.3 |

| Ex. No. | Product | Starting material A | Starting material B | Molecular mass calculated | [M + H]+ found | Yield (% of theory) |
|---|---|---|---|---|---|---|
| A131 | | | | 373 | 374 | 57.7 |
| A132 | | | | 377 | 378 | 17.2 |
| A133 | | | | 385 | 386 | 14.0 |

-continued

| Ex. No. | Product | Starting material A | Starting material B | Molecular mass calculated | [M + H]+ found | Yield (% of theory) |
|---|---|---|---|---|---|---|
| A134 | | | | 405 | 406 | 8.9 |
| A135 | | | | 413 | 414 | 17.2 |
| A136 | | | | 423 | 424 | 12.8 |

| Ex. No. | Product | Starting material A | Starting material B | Molecular mass calculated | [M + H]+ found | Yield (% of theory) |
|---|---|---|---|---|---|---|
| A137 | (structure) | (structure) | (structure) | 434 | 435 | 10.1 |
| A138 | (structure) | (structure) | (structure) | 448 | 449 | 10.0 |
| A139 | (structure) | (structure) | (structure) | 474 | 475 | 52.1 |

-continued

| Ex. No. | Product | Starting material A | Starting material B | Molecular mass calculated | [M + H]+ found | Yield (% of theory) |
|---|---|---|---|---|---|---|
| A140 | | | | 488 | 489 | 52.3 |
| A141 | | | | 496 | 497 | 50.2 |
| A142 | | | | 510 | 511 | 43.5 |

-continued

| Ex. No. | Product | Starting material A | Starting material B | Molecular mass calculated | [M + H]+ found | Yield (% of theory) |
|---|---|---|---|---|---|---|
| A143 | | | | 361 | 362 | 56.0 |
| A144 | | | | 435 | 436 | 3.7 |
| A145 | | | | 435 | 436 | 67.4 |

-continued

| Ex. No. | Product | Starting material A | Starting material B | Molecular mass calculated | [M + H]+ found | Yield (% of theory) |
|---|---|---|---|---|---|---|
| A146 | | | | 331 | 332 | 64.1 |
| A147 | | | | 344 | 345 | 70.7 |
| A148 | | | | 358 | 359 | 72.7 |
| A149 | | | | 359 | 360 | 58.8 |

-continued

| Ex. No. | Product | Starting material A | Starting material B | Molecular mass calculated | [M + H]+ found | Yield (% of theory) |
|---|---|---|---|---|---|---|
| A150 | | | | 373 | 374 | 56.3 |
| A151 | | | | 377 | 378 | 55.5 |
| A152 | | | | 385 | 386 | 64.2 |
| A153 | | | | 405 | 406 | 32.4 |

-continued

| Ex. No. | Product | Starting material A | Starting material B | Molecular mass calculated | [M + H]+ found | Yield (% of theory) |
|---|---|---|---|---|---|---|
| A154 | | | | 413 | 414 | 55.7 |
| A155 | | | | 423 | 424 | 53.9 |
| A156 | | | | 434 | 435 | 74.9 |

-continued

| Ex. No. | Product | Starting material A | Starting material B | Molecular mass calculated | [M + H]+ found | Yield (% of theory) |
|---|---|---|---|---|---|---|
| A157 | | | | 448 | 449 | 69.0 |
| A158 | | | | 464 | 465 | 72.0 |
| A159 | | | | 474 | 475 | 73.0 |

-continued

| Ex. No. | Product | Starting material A | Starting material B | Molecular mass calculated | [M + H]+ found | Yield (% of theory) |
|---|---|---|---|---|---|---|
| A160 | | | | 488 | 489 | 75.2 |
| A161 | | | | 496 | 497 | 75.5 |
| A162 | | | | 510 | 511 | 67.4 |

-continued

| Ex. No. | Product | Starting material A | Starting material B | Molecular mass calculated | [M + H]+ found | Yield (% of theory) |
|---|---|---|---|---|---|---|
| A163 | | | | 371 | 372 | 75.2 |
| A164 | | | | 421 | 422 | 57.7 |
| A165 | | | | 435 | 436 | 71.3 |

-continued

| Ex. No. | Product | Starting material A | Starting material B | Molecular mass calculated | [M + H]+ found | Yield (% of theory) |
|---|---|---|---|---|---|---|
| A166 | (structure) | (structure) | (structure) | 435 | 436 | 54.0 |
| A167 | (structure) | (structure) | (structure) | 326 | 327 | 50.9 |
| A168 | (structure) | (structure) | (structure) | 339 | 340 | 76.3 |

-continued

| Ex. No. | Product | Starting material A | Starting material B | Molecular mass calculated | [M + H]+ found | Yield (% of theory) |
|---|---|---|---|---|---|---|
| A169 | | | | 353 | 354 | 50.4 |
| A170 | | | | 372 | 373 | 30.6 |
| A171 | | | | 418 | 419 | 13.6 |

| Ex. No. | Product | Starting material A | Starting material B | Molecular mass calculated | [M + H]+ found | Yield (% of theory) |
|---|---|---|---|---|---|---|
| A172 | | | | 430 | 431 | 63.8 |
| A173 | | | | 444 | 445 | 26.2 |

-continued

| Ex. No. | Product | Starting material A | Starting material B | Molecular mass calculated | [M + H]+ found | Yield (% of theory) |
|---|---|---|---|---|---|---|
| A174 | | | | 460 | 461 | 32.2 |
| A175 | | | | 470 | 471 | 96.9 |

-continued

| Ex. No. | Product | Starting material A | Starting material B | Molecular mass calculated | [M + H]+ found | Yield (% of theory) |
|---|---|---|---|---|---|---|
| A176 | | | | 484 | 485 | 18.2 |
| A177 | | | | 492 | 493 | 78.5 |
| A178 | | | | 356 | 357 | 17.1 |

-continued

| Ex. No. | Product | Starting material A | Starting material B | Molecular mass calculated | [M + H]+ found | Yield (% of theory) |
|---|---|---|---|---|---|---|
| A179 | | | | 366 | 367 | 31.1 |
| A180 | | | | 416 | 417 | 80.0 |
| A181 | | | | 430 | 431 | 66.2 |

-continued

| Ex. No. | Product | Starting material A | Starting material B | Molecular mass calculated | [M + H]+ found | Yield (% of theory) |
|---|---|---|---|---|---|---|
| A182 | (4-methoxyphenyl pyridine product with S-CH2-CO-O-CH2-phenyl) | Br-CH2-CO-O-CH2-phenyl | 2-mercapto-6-amino-4-(4-methoxyphenyl)-3,5-dicyanopyridine | 430 | 431 | 73.6 |
| A183 | (4-methylphenyl pyridine product with S-CH2CH2-OH) | Br-CH2CH2-OH | 2-mercapto-6-amino-4-(4-methylphenyl)-3,5-dicyanopyridine | 310 | 311 | 28.4 |
| A184 | (4-methylphenyl pyridine product with S-CH2-CO-NH2) | Br-CH2-CO-NH2 | 2-mercapto-6-amino-4-(4-methylphenyl)-3,5-dicyanopyridine | 323 | 324 | 39.3 |

-continued

| Ex. No. | Product | Starting material A | Starting material B | Molecular mass calculated | [M + H]+ found | Yield (% of theory) |
|---|---|---|---|---|---|---|
| A185 | 2-amino-6-(2-hydroxypropylthio)-4-(4-methylphenyl)pyridine-3,5-dicarbonitrile | 1-bromo-2-hydroxypropane | 2-amino-6-mercapto-4-(4-methylphenyl)pyridine-3,5-dicarbonitrile | 324 | 325 | 41.9 |
| A186 | corresponding product | 2-bromopropanamide | same thiol | 337 | 338 | 40.9 |
| A187 | corresponding product | methyl bromoacetate | same thiol | 338 | 339 | 11.5 |

-continued

| Ex. No. | Product | Starting material A | Starting material B | Molecular mass calculated | [M + H]+ found | Yield (% of theory) |
|---|---|---|---|---|---|---|
| A188 | | | | 352 | 353 | 29.2 |
| A189 | | | | 356 | 357 | 51.9 |
| A190 | | | | 364 | 365 | 77.4 |

-continued

| Ex. No. | Product | Starting material A | Starting material B | Molecular mass calculated | [M + H]+ found | Yield (% of theory) |
|---|---|---|---|---|---|---|
| A191 | | | | 414 | 415 | 51.8 |
| A192 | | | | 428 | 429 | 58.2 |

-continued

| Ex. No. | Product | Starting material A | Starting material B | Molecular mass calculated | [M + H]+ found | Yield (% of theory) |
|---|---|---|---|---|---|---|
| A193 | | | | 444 | 445 | 58.2 |
| A194 | | | | 454 | 455 | 29.5 |

-continued

| Ex. No. | Product | Starting material A | Starting material B | Molecular mass calculated | [M + H]+ found | Yield (% of theory) |
|---|---|---|---|---|---|---|
| A195 | (structure) | (structure) | (structure) | 468 | 469 | 43.8 |
| A196 | (structure) | (structure) | (structure) | 476 | 477 | 51.7 |
| A197 | (structure) | (structure) | (structure) | 490 | 491 | 73.9 |

-continued

| Ex. No. | Product | Starting material A | Starting material B | Molecular mass calculated | [M + H]+ found | Yield (% of theory) |
|---|---|---|---|---|---|---|
| A198 | | | | 340 | 341 | 37.9 |
| A199 | | | | 350 | 351 | 80.8 |
| A200 | | | | 400 | 401 | 48.4 |

-continued

| Ex. No. | Product | Starting material A | Starting material B | Molecular mass calculated | [M + H]+ found | Yield (% of theory) |
|---|---|---|---|---|---|---|
| A201 | | | | 414 | 415 | 20.7 |
| A202 | | | | 414 | 415 | 61.0 |
| A203 | | | | 341 | 342 | 55.4 |

-continued

| Ex. No. | Product | Starting material A | Starting material B | Molecular mass calculated | [M + H]+ found | Yield (% of theory) |
|---|---|---|---|---|---|---|
| A204 | | | | 354 | 355 | 38.4 |
| A205 | | | | 368 | 369 | 70.6 |
| A206 | | | | 369 | 370 | 49.5 |

-continued

| Ex. No. | Product | Starting material A | Starting material B | Molecular mass calculated | [M + H]+ found | Yield (% of theory) |
|---|---|---|---|---|---|---|
| A207 | (structure) | (structure) | (structure) | 383 | 384 | 65.5 |
| A208 | (structure) | (structure) | (structure) | 395 | 396 | 14.2 |
| A209 | (structure) | (structure) | (structure) | 415 | 416 | 22.9 |

| Ex. No. | Product | Starting material A | Starting material B | Molecular mass calculated | [M + H]+ found | Yield (% of theory) |
|---|---|---|---|---|---|---|
| A210 | 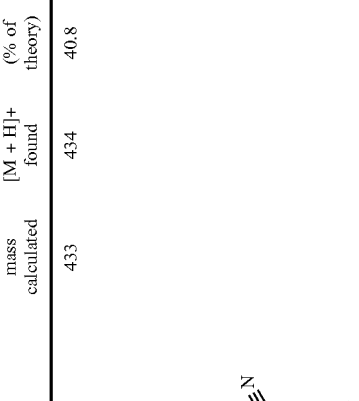 | 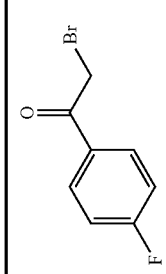 | 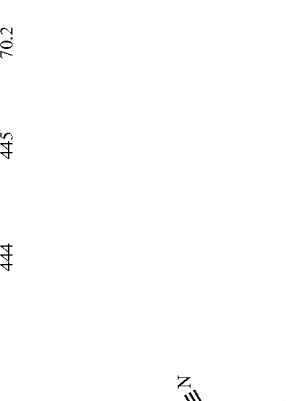 | 433 | 434 | 40.8 |
| A211 | 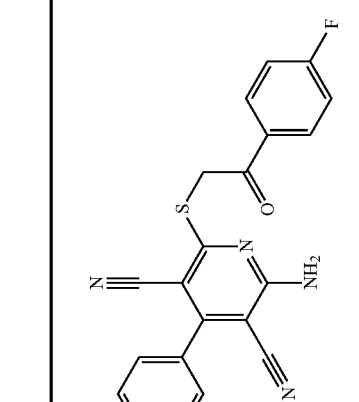 | 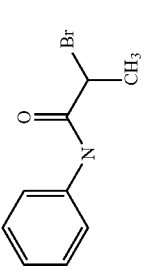 | 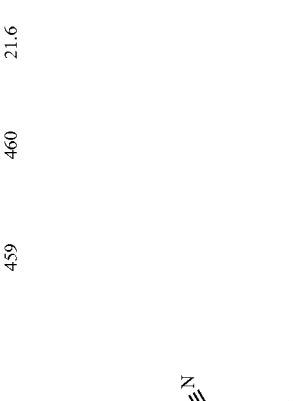 | 444 | 445 | 70.2 |
| A212 | 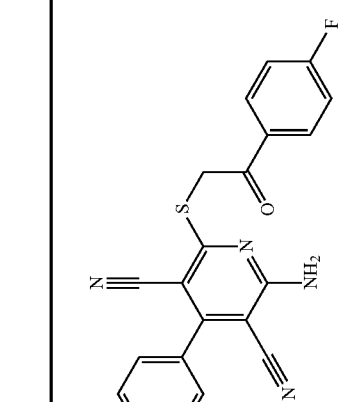 | 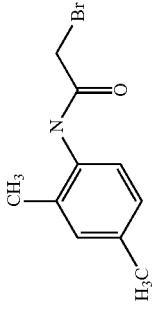 | 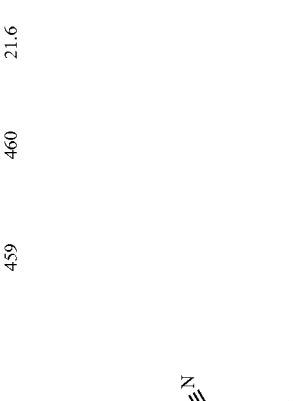 | 459 | 460 | 21.6 |

-continued

| Ex. No. | Product | Starting material A | Starting material B | Molecular mass calculated | [M + H]+ found | Yield (% of theory) |
|---|---|---|---|---|---|---|
| A213 | | | | 475 | 476 | 57.5 |
| A214 | | | | 485 | 486 | 41.5 |

| Ex. No. | Product | Starting material A | Starting material B | Molecular mass calculated | [M + H]+ found | Yield (% of theory) |
|---|---|---|---|---|---|---|
| A215 | 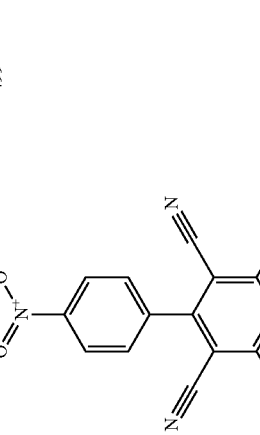 | 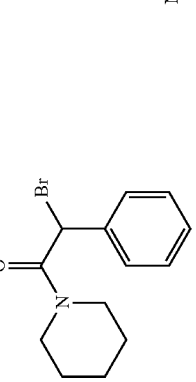 | 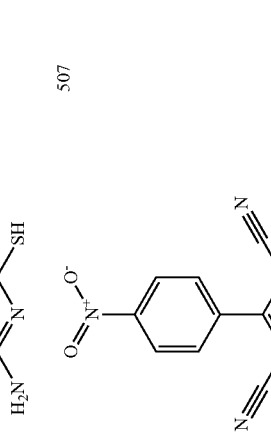 | 499 | 500 | 43.1 |
| A216 | 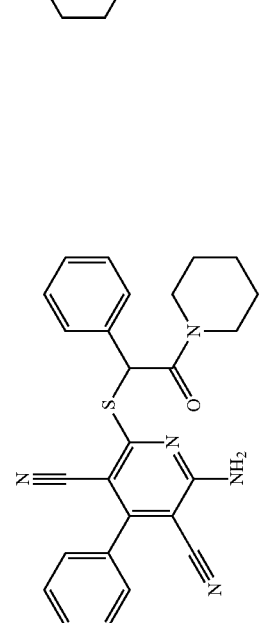 | 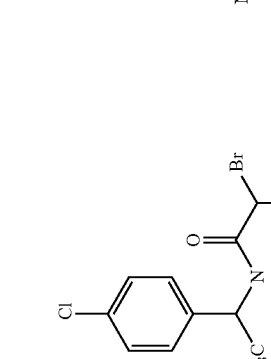 | 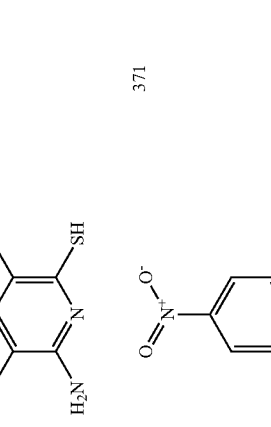 | 507 | 508 | 56.2 |
| A217 | 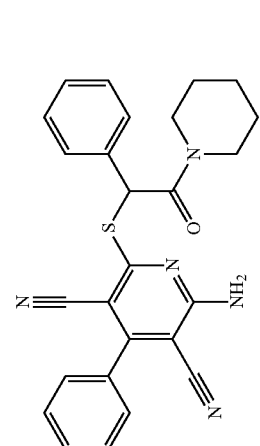 | 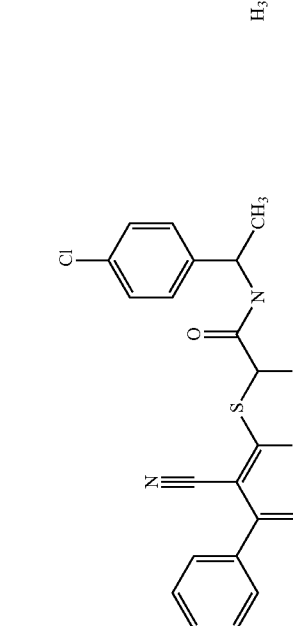 | 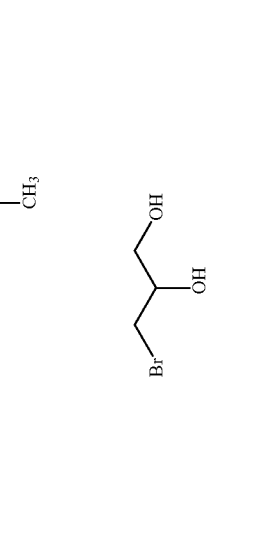 | 371 | 372 | 62.5 |

-continued

| Ex. No. | Product | Starting material A | Starting material B | Molecular mass calculated | [M + H]+ found | Yield (% of theory) |
|---|---|---|---|---|---|---|
| A218 | | | | 381 | 382 | 39.9 |
| A219 | | | | 431 | 432 | 55.6 |
| A220 | | | | 445 | 446 | 32.6 |

| Ex. No. | Product | Starting material A | Starting material B | Molecular mass calculated | [M + H]+ found | Yield (% of theory) |
|---|---|---|---|---|---|---|
| A221 | 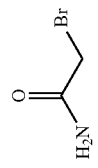 | 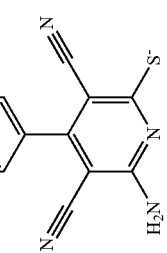 |  | 352 | 353 | 61.3 |
| A222 | 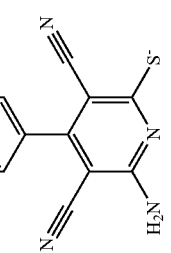 | | | 365 | 366 | 80.2 |

-continued

| Ex. No. | Product | Starting material A | Starting material B | Molecular mass calculated | [M + H]+ found | Yield (% of theory) |
|---|---|---|---|---|---|---|
| A223 | | | | 366 | 367 | 73.1 |
| A224 | | | | 379 | 380 | 81.7 |

| Ex. No. | Product | Starting material A | Starting material B | Molecular mass calculated | [M + H]+ found | Yield (% of theory) |
|---|---|---|---|---|---|---|
| A225 | | | | 380 | 381 | 71.0 |
| A226 | | | | 394 | 395 | 65.9 |

| Ex. No. | Product | Starting material A | Starting material B | Molecular mass calculated | [M + H]+ found | Yield (% of theory) |
|---|---|---|---|---|---|---|
| A227 | 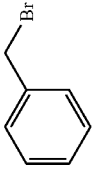 | 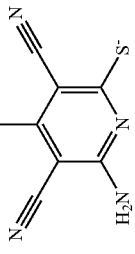 | 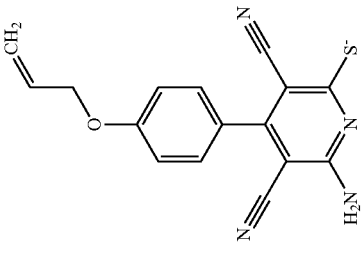 | 398 | 399 | 76.3 |
| A228 | 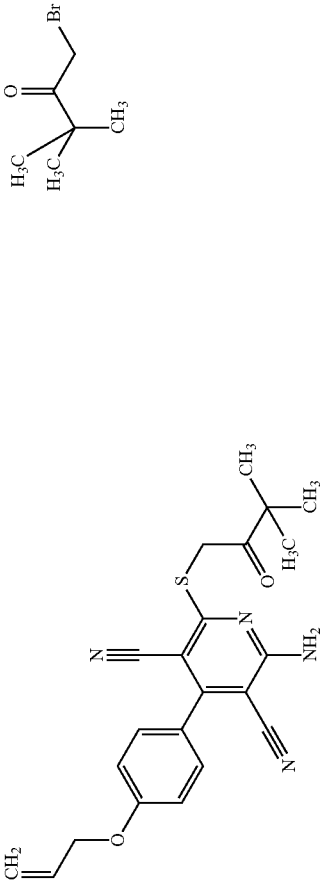 |  |  | 407 | 408 | 79.7 |

| Ex. No. | Product | Starting material A | Starting material B | Molecular mass calculated | [M + H]+ found | Yield (% of theory) |
|---|---|---|---|---|---|---|
| A229 | | | | 427 | 428 | 40.8 |
| A230 | | | | 434 | 435 | 22.1 |

-continued

| Ex. No. | Product | Starting material A | Starting material B | Molecular mass calculated | [M + H]+ found | Yield (% of theory) |
|---|---|---|---|---|---|---|
| A231 | (structure) | (structure) | (structure) | 444 | 445 | 9.7 |
| A232 | (structure) | (structure) | (structure) | 456 | 457 | 15.6 |

| Ex. No. | Product | Starting material A | Starting material B | Molecular mass calculated | [M + H]+ found | Yield (% of theory) |
|---|---|---|---|---|---|---|
| A233 | | | | 470 | 471 | 43.7 |
| A234 | | | | 486 | 487 | 71.1 |

-continued
| Ex. No. | Product | Starting material A | Starting material B | Molecular mass calculated | [M + H]+ found | Yield (% of theory) |
|---|---|---|---|---|---|---|
| A235 |  |  | 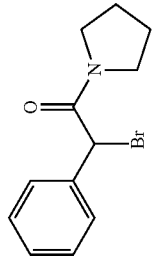 | 496 | 497 | 96.4 |
| A236 | 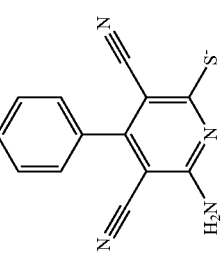 | 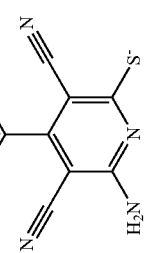 | 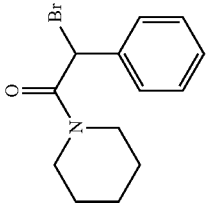 | 510 | 511 | 84.6 |

| Ex. No. | Product | Starting material A | Starting material B | Molecular mass calculated | [M + H]+ found | Yield (% of theory) |
|---|---|---|---|---|---|---|
| A237 |  | 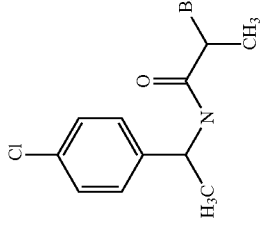 |  | 518 | 519 | 41.7 |
| A238 | 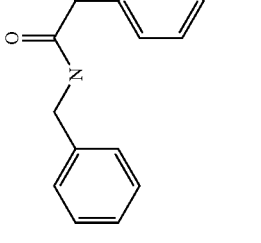 | 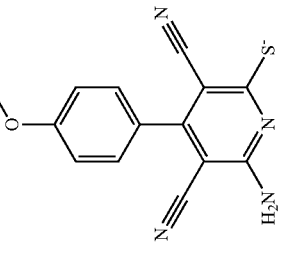 | 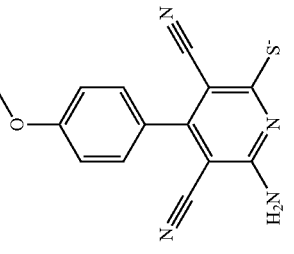 | 532 | 533 | 28.8 |

| Ex. No. | Product | Starting material A | Starting material B | Molecular mass calculated | [M + H]+ found | Yield (% of theory) |
|---|---|---|---|---|---|---|
| A239 | (structure) | 3-bromo-1,2-propanediol | (structure) | 382 | 383 | 83.7 |
| A240 | (structure) | 3-bromodihydrofuran-2(3H)-one | (structure) | 392 | 393 | 54.8 |

| Ex. No. | Product | Starting material A | Starting material B | Molecular mass calculated | [M + H]+ found | Yield (% of theory) |
|---|---|---|---|---|---|---|
| A241 | (structure) | (structure) | (structure) | 443 | 444 | 75.0 |
| A242 | (structure) | (structure) | (structure) | 457 | 458 | 50.2 |

| Ex. No. | Product | Starting material A | Starting material B | Molecular mass calculated | [M + H]+ found | Yield (% of theory) |
|---|---|---|---|---|---|---|
| A243 | (structure) | (structure) | (structure) | 457 | 458 | 44.9 |
| A244 | (structure) | (structure) | (structure) | 352 | 353 | 54.5 |

-continued

| Ex. No. | Product | Starting material A | Starting material B | Molecular mass calculated | [M + H]+ found | Yield (% of theory) |
|---|---|---|---|---|---|---|
| A245 | (structure) | bromoacetamide | (thiol pyridine structure) | 369 | 370 | 85.5 |
| A246 | (structure) | 1-bromo-2-propanol | (thiol pyridine structure) | 370 | 371 | 60.7 |
| A247 | (structure) | methyl bromoacetate | (thiol pyridine structure) | 384 | 385 | 59.1 |

| Ex. No. | Product | Starting material A | Starting material B | Molecular mass calculated | [M + H]+ found | Yield (% of theory) |
|---|---|---|---|---|---|---|
| A248 | (product with S-CH2-CH(OH)-CH2OH side chain, 3,4-dimethoxyphenyl, two CN, NH2) | 3-bromo-1,2-propanediol | 4-(3,4-dimethoxyphenyl)-3,5-dicyano-6-amino-2-mercaptopyridine | 386 | 387 | 79.7 |
| A249 | (product with S-(CH2)3-OH side chain) | 3-bromo-1-propanol | 4-(3,4-dimethoxyphenyl)-3,5-dicyano-6-amino-2-mercaptopyridine | 370 | 371 | 51.6 |
| A250 | (product with S-CH2CH2-O-CH3 side chain) | 2-bromoethyl methyl ether | 4-(3,4-dimethoxyphenyl)-3,5-dicyano-6-amino-2-mercaptopyridine | 370 | 371 | 49.4 |

-continued

| Ex. No. | Product | Starting material A | Starting material B | Molecular mass calculated | [M + H]+ found | Yield (% of theory) |
|---|---|---|---|---|---|---|
| A251 | | | | 448 | 449 | 70.4 |
| A252 | | | | 426 | 427 | 39.0 |
| A253 | | | | 324 | 325 | 66.9 |

| Ex. No. | Product | Starting material A | Starting material B | Molecular mass calculated | [M + H]+ found | Yield (% of theory) |
|---|---|---|---|---|---|---|
| A254 | (structure) | Br-CH2CH2-OH | (pyridine structure) | 328 | 329 | 90.1 |
| A255 | (structure) | Br-CH2-C(=O)-NH2 | (pyridine structure) | 341 | 342 | 114.5 |
| A256 | (structure) | H3C-CH(O)-CH2-Br | (pyridine structure) | 342 | 343 | 70.7 |

| Ex. No. | Product | Starting material A | Starting material B | Molecular mass calculated | [M + H]+ found | Yield (% of theory) |
|---|---|---|---|---|---|---|
| A257 | (product with S-CH2-C(=O)-O-CH3 chain) | methyl bromoacetate | (pyridine-SH starting material) | 356 | 357 | 77.7 |
| A258 | (product with S-CH2-phenyl chain) | benzyl bromide | (pyridine-SH starting material) | 374 | 375 | 87.1 |
| A259 | (product with S-(CH2)3-OH chain) | 3-bromo-1-propanol | (pyridine-SH starting material) | 342 | 343 | 85.3 |

| Ex. No. | Product | Starting material A | Starting material B | Molecular mass calculated | [M + H]+ found | Yield (% of theory) |
|---|---|---|---|---|---|---|
| A260 | (product structure) | Br-CH2CH2-O-CH3 | (pyridine-thiol starting material) | 342 | 343 | 73.3 |
| A261 | (product structure) | Br-(CH2)4-SO2NH2 | (pyridine-thiol starting material) | 419 | 420 | 91.3 |
| A262 | (product structure) | Br-CH2-C(O)-N(CH2CH3)2 | (pyridine-thiol starting material) | 397 | 398 | 66.2 |

-continued

| Ex. No. | Product | Starting material A | Starting material B | Molecular mass calculated | [M + H]+ found | Yield (% of theory) |
|---|---|---|---|---|---|---|
| A263 | methyl 4-[2-amino-6-(allylthio)-3,5-dicyanopyridin-4-yl]benzoate | allyl bromide | methyl 4-(2-amino-3,5-dicyano-6-mercaptopyridin-4-yl)benzoate | 350 | 351 | 50.5 |
| A264 | methyl 4-[2-amino-3,5-dicyano-6-(2-hydroxypropylthio)pyridin-4-yl]benzoate | 1-bromo-2-propanol | methyl 4-(2-amino-3,5-dicyano-6-mercaptopyridin-4-yl)benzoate | 368 | 369 | 49.1 |

| Ex. No. | Product | Starting material A | Starting material B | Molecular mass calculated | [M + H]+ found | Yield (% of theory) |
|---|---|---|---|---|---|---|
| A265 | | | | 382 | 383 | 58.6 |
| A266 | | | | 400 | 401 | 53.4 |

| Ex. No. | Product | Starting material A | Starting material B | Molecular mass calculated | [M + H]+ found | Yield (% of theory) |
|---|---|---|---|---|---|---|
| A267 | | | | 368 | 369 | 48.9 |
| A268 | | | | 368 | 369 | 31.8 |

| Ex. No. | Product | Starting material A | Starting material B | Molecular mass calculated | [M + H]+ found | Yield (% of theory) |
|---|---|---|---|---|---|---|
| A269 | (structure) | (structure) | (structure) | 381 | 382 | 30.2 |
| A270 | (structure) | (structure) | (structure) | 423 | 424 | 17.0 |

-continued

| Ex. No. | Product | Starting material A | Starting material B | Molecular mass calculated | [M + H]+ found | Yield (% of theory) |
|---|---|---|---|---|---|---|
| A271 | (structure) | (allyl bromide) | (structure) | 338 | 339 | 71.2 |
| A272 | (structure) | (2-bromoethanol) | (structure) | 342 | 343 | 50.8 |
| A273 | (structure) | (2-bromoacetamide) | (structure) | 355 | 356 | 96.0 |

-continued

| Ex. No. | Product | Starting material A | Starting material B | Molecular mass calculated | [M + H]+ found | Yield (% of theory) |
|---|---|---|---|---|---|---|
| A274 | | | | 356 | 357 | 69.0 |
| A275 | | | | 370 | 371 | 80.5 |
| A276 | | | | 372 | 373 | 85.4 |

-continued

| Ex. No. | Product | Starting material A | Starting material B | Molecular mass calculated | [M + H]+ found | Yield (% of theory) |
|---|---|---|---|---|---|---|
| A277 | | | | 356 | 357 | 69.3 |
| A278 | | | | 356 | 357 | 58.9 |
| A279 | | | | 434 | 435 | 84.4 |

-continued

| Ex. No. | Product | Starting material A | Starting material B | Molecular mass calculated | [M + H]+ found | Yield (% of theory) |
|---|---|---|---|---|---|---|
| A280 | (structure) | (bromoacetyl diethylamide) | (structure) | 411 | 412 | 80.2 |
| A281 | (structure) | allyl bromide | (structure) | 338 | 339 | 60.6 |
| A282 | (structure) | 2-bromoethanol | (structure) | 342 | 343 | 59.3 |

| Ex. No. | Product | Starting material A | Starting material B | Molecular mass calculated | [M + H]+ found | Yield (% of theory) |
|---|---|---|---|---|---|---|
| A283 | (pyridine with CN, NH₂, CN, S-CH₂-CH(OH)-CH₃ substituents and 4-hydroxy-3-methoxyphenyl group) | 1-bromo-2-hydroxypropane (HOCH(CH₃)CH₂Br) | (4-aryl-pyridine with CN, SH, CN, NH₂, and 4-hydroxy-3-methoxyphenyl) | 356 | 357 | 62.0 |
| A284 | (pyridine with CN, NH₂, CN, S-CH₂-C(O)OCH₃ substituents and 4-hydroxy-3-methoxyphenyl group) | methyl bromoacetate (BrCH₂C(O)OCH₃) | (4-aryl-pyridine with CN, SH, CN, NH₂, and 4-hydroxy-3-methoxyphenyl) | 370 | 371 | 55.3 |
| A285 | (pyridine with CN, NH₂, CN, S-CH₂-C₆H₅ substituents and 4-hydroxy-3-methoxyphenyl group) | benzyl bromide (C₆H₅CH₂Br) | (4-aryl-pyridine with CN, SH, CN, NH₂, and 4-hydroxy-3-methoxyphenyl) | 388 | 389 | 59.0 |

| Ex. No. | Product | Starting material A | Starting material B | Molecular mass calculated | [M + H]+ found | Yield (% of theory) |
| --- | --- | --- | --- | --- | --- | --- |
| A286 | | | | 356 | 357 | 43.2 |
| A287 | | | | 356 | 357 | 46.6 |
| A288 | | | | 434 | 435 | 62.5 |

-continued

| Ex. No. | Product | Starting material A | Starting material B | Molecular mass calculated | [M + H]+ found | Yield (% of theory) |
|---|---|---|---|---|---|---|
| A289 | | | | 411 | 412 | 24.5 |
| A290 | | | | 421 | 422 | 100.6 |
| A291 | | | | 438 | 439 | 75.4 |

-continued

| Ex. No. | Product | Starting material A | Starting material B | Molecular mass calculated | [M + H]+ found | Yield (% of theory) |
|---|---|---|---|---|---|---|
| A292 | (structure) | (structure) | (structure) | 453 | 454 | 58.8 |
| A293 | (structure) | (structure) | (structure) | 439 | 440 | 50.2 |
| A294 | (structure) | (structure) | (structure) | 352 | 353 | 68.7 |

-continued

| Ex. No. | Product | Starting material A | Starting material B | Molecular mass calculated | [M + H]+ found | Yield (% of theory) |
|---|---|---|---|---|---|---|
| A295 | (pyridine with S-CH2CH2-OH, CN, NH2, aryl with CH3CH2-O and OH) | Br-CH2CH2-OH | (pyridine with SH, CN, NH2, aryl with OCH2CH3 and OH) | 356 | 357 | 73.5 |
| A296 | (pyridine with S-CH2-C(O)NH2, CN, NH2, aryl with CH3CH2-O and OH) | Br-CH2-C(O)NH2 | (pyridine with SH, CN, NH2, aryl with OCH2CH3 and OH) | 369 | 370 | 92.9 |
| A297 | (pyridine with S-CH2-CH(OH)-CH3, CN, NH2, aryl with CH3CH2-O and OH) | H3C-CH(OH)-CH2-Br | (pyridine with SH, CN, NH2, aryl with OCH2CH3 and OH) | 370 | 371 | 78.6 |

| Ex. No. | Product | Starting material A | Starting material B | Molecular mass calculated | [M + H]+ found | Yield (% of theory) |
|---|---|---|---|---|---|---|
| A298 | (methyl ester product with pyridine core, OH, OCH₃, CN, NH₂, S-CH₂COOCH₃) | methyl bromoacetate | (pyridine with SH, CN, NH₂, OH, OCH₃) | 384 | 385 | 71.0 |
| A299 | (benzyl thioether product with pyridine core, OH, OCH₃, CN, NH₂, S-CH₂Ph) | benzyl bromide | (pyridine with SH, CN, NH₂, OH, OCH₃) | 402 | 403 | 84.2 |

-continued

| Ex. No. | Product | Starting material A | Starting material B | Molecular mass calculated | [M + H]+ found | Yield (% of theory) |
|---|---|---|---|---|---|---|
| A300 | | | | 386 | 387 | 100.9 |
| A301 | | | | 370 | 371 | 100.4 |
| A302 | | | | 370 | 371 | 82.3 |

-continued

| Ex. No. | Product | Starting material A | Starting material B | Molecular mass calculated | [M + H]+ found | Yield (% of theory) |
|---|---|---|---|---|---|---|
| A303 | (product structure) | 4-bromobutanesulfonamide | (pyridine starting material with 3-methoxy-4-hydroxyphenyl) | 448 | 449 | 82.0 |
| A304 | (product structure) | 2-bromo-N,N-diethylacetamide | (pyridine starting material with 3-methoxy-4-hydroxyphenyl) | 426 | 427 | 60.2 |
| A305 | (product structure) | allyl bromide | (pyridine starting material with 3,5-dihydroxyphenyl) | 324 | 325 | 26.8 |

| Ex. No. | Product | Starting material A | Starting material B | Molecular mass calculated | [M + H]+ found | Yield (% of theory) |
|---|---|---|---|---|---|---|
| A306 | 4-(3,5-dihydroxyphenyl)-2-amino-6-(2-hydroxyethylthio)-3,5-dicyanopyridine structure | Br-CH2CH2-OH | 4-(3,5-dihydroxyphenyl)-2-mercapto-6-amino-3,5-dicyanopyridine | 328 | 329 | 33.8 |
| A307 | corresponding acetamide-S product | Br-CH2-C(O)-NH2 | same pyridine-thiol | 341 | 342 | 43.1 |
| A308 | 2-hydroxypropylthio product | Br-CH2-CH(OH)-CH3 | same pyridine-thiol | 342 | 343 | 34.2 |

-continued

| Ex. No. | Product | Starting material A | Starting material B | Molecular mass calculated | [M + H]+ found | Yield (% of theory) |
|---|---|---|---|---|---|---|
| A309 | | | | 356 | 357 | 30.9 |
| A310 | | | | 374 | 375 | 34.7 |
| A311 | | | | 358 | 359 | 41.0 |

-continued

| Ex. No. | Product | Starting material A | Starting material B | Molecular mass calculated | [M + H]+ found | Yield (% of theory) |
|---|---|---|---|---|---|---|
| A312 | 4-(3,5-dihydroxyphenyl)-6-[(3-hydroxypropyl)thio]-2-amino pyridine-3,5-dicarbonitrile structure | Br-(CH2)3-OH | 4-(3,5-dihydroxyphenyl)-6-mercapto-2-amino pyridine-3,5-dicarbonitrile | 342 | 343 | 33.3 |
| A313 | 4-(3,5-dihydroxyphenyl)-6-[(2-methoxyethyl)thio]-2-amino pyridine-3,5-dicarbonitrile structure | Br-CH2CH2-O-CH3 | 4-(3,5-dihydroxyphenyl)-6-mercapto-2-amino pyridine-3,5-dicarbonitrile | 342 | 343 | 25.1 |
| A314 | 4-(3,5-dihydroxyphenyl)-6-[(4-sulfamoylbutyl)thio]-2-amino pyridine-3,5-dicarbonitrile structure | Br-(CH2)4-SO2NH2 | 4-(3,5-dihydroxyphenyl)-6-mercapto-2-amino pyridine-3,5-dicarbonitrile | 419 | 420 | 30.3 |

-continued

| Ex. No. | Product | Starting material A | Starting material B | Molecular mass calculated | [M + H]+ found | Yield (% of theory) |
|---|---|---|---|---|---|---|
| A315 | (product structure) | BrCH2C(O)NHCH3 | (pyridine starting material with OH, OH) | 355 | 356 | 36.3 |
| A316 | (product structure) | BrCH2C(O)N(CH2CH3)2 | (pyridine starting material with OH, OH) | 397 | 398 | 30.7 |
| A317 | (product structure) | allyl bromide (H2C=CHCH2Br) | (pyridine starting material with OH, OCH3, OCH3) | 368 | 369 | 68.9 |

| Ex. No. | Product | Starting material A | Starting material B | Molecular mass calculated | [M + H]+ found | Yield (% of theory) |
|---|---|---|---|---|---|---|
| A318 | (structure) | 2-bromoethanol | (structure) | 372 | 373 | 77.6 |
| A319 | (structure) | 2-bromoacetamide | (structure) | 385 | 386 | 107.4 |
| A320 | (structure) | 1-bromo-2-propanol | (structure) | 386 | 387 | 64.2 |

| Ex. No. | Product | Starting material A | Starting material B | Molecular mass calculated | [M + H]+ found | Yield (% of theory) |
|---|---|---|---|---|---|---|
| A321 | 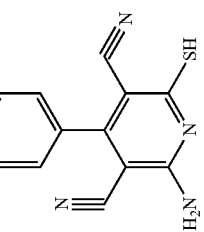 | 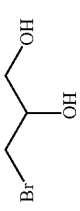 | 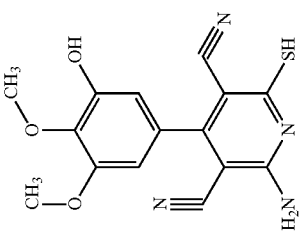 | 402 | 403 | 88.7 |
| A322 | 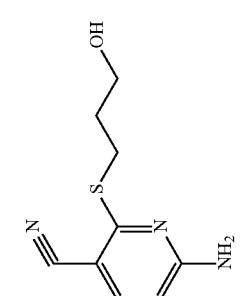 |  | 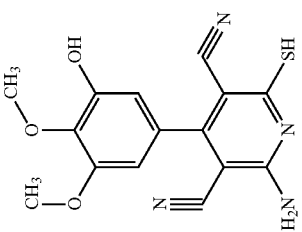 | 386 | 387 | 73.8 |
| A323 | 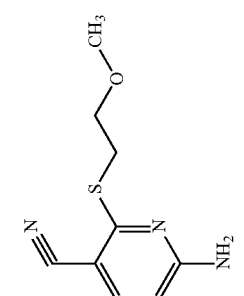 |  |  | 386 | 387 | 74.5 |

| Ex. No. | Product | Starting material A | Starting material B | Molecular mass calculated | [M + H]+ found | Yield (% of theory) |
|---|---|---|---|---|---|---|
| A324 | | | | 464 | 465 | 83.3 |
| A325 | | | | 442 | 443 | 85.6 |
| A326 | | | | 322 | 323 | 53.0 |

| Ex. No. | Product | Starting material A | Starting material B | Molecular mass calculated | [M + H]+ found | Yield (% of theory) |
|---|---|---|---|---|---|---|
| A327 | (product structure) | HO-CH2-CH2-Br | (starting material B structure) | 326 | 327 | 19.3 |
| A328 | (product structure) | BrCH2-C(=O)-NH2 | (starting material B structure) | 339 | 340 | 88.1 |
| A329 | (product structure) | H3C-CH(OH)-CH2-Br | (starting material B structure) | 340 | 341 | 77.3 |

| Ex. No. | Product | Starting material A | Starting material B | Molecular mass calculated | [M + H]+ found | Yield (% of theory) |
|---|---|---|---|---|---|---|
| A330 | (structure) | BrCH2C(O)OCH3 | (structure) | 354 | 355 | 68.3 |
| A331 | (structure) | benzyl bromide | (structure) | 372 | 373 | 59.3 |
| A332 | (structure) | 3-bromo-1,2-propanediol | (structure) | 356 | 357 | 75.2 |

| Ex. No. | Product | Starting material A | Starting material B | Molecular mass calculated | [M + H]+ found | Yield (% of theory) |
|---|---|---|---|---|---|---|
| A333 | (product structure: pyridine with CN, NH2, S-(CH2)4-OH, and 4-hydroxy-3-methylphenyl) | Br-(CH2)4-OH | (pyridine-SH starting material with 4-hydroxy-3-methylphenyl, 2×CN, NH2) | 340 | 341 | 47.0 |
| A334 | (product structure: pyridine with CN, NH2, S-CH2CH2-O-CH3, and 4-hydroxy-3-methylphenyl) | Br-CH2CH2-O-CH3 | (same pyridine-SH starting material) | 340 | 341 | 60.5 |
| A335 | (product structure: pyridine with CN, NH2, S-(CH2)4-SO2NH2, and 4-hydroxy-3-methylphenyl) | Br-(CH2)4-SO2NH2 | (same pyridine-SH starting material) | 418 | 419 | 80.5 |

-continued

| Ex. No. | Product | Starting material A | Starting material B | Molecular mass calculated | [M + H]+ found | Yield (% of theory) |
|---|---|---|---|---|---|---|
| A336 | (structure) | (structure) | (structure) | 395 | 396 | 74.6 |
| A337 | (structure) | (structure) | (structure) | 354 | 355 | 56.4 |
| A338 | (structure) | (structure) | (structure) | 371 | 372 | 47.4 |

-continued

| Ex. No. | Product | Starting material A | Starting material B | Molecular mass calculated | [M + H]+ found | Yield (% of theory) |
|---|---|---|---|---|---|---|
| A339 | (structure) | (structure) | (structure) | 372 | 373 | 68.5 |
| A340 | (structure) | (structure) | (structure) | 386 | 387 | 81.0 |
| A341 | (structure) | (structure) | (structure) | 404 | 405 | 77.1 |

| Ex. No. | Product | Starting material A | Starting material B | Molecular mass calculated | [M + H]+ found | Yield (% of theory) |
|---|---|---|---|---|---|---|
| A342 | (product structure) | 3-bromo-1,2-propanediol | (pyridine starting material) | 388 | 389 | 64.1 |
| A343 | (product structure) | 3-bromo-1-propanol | (pyridine starting material) | 372 | 373 | 65.5 |
| A344 | (product structure) | 1-bromo-2-methoxyethane | (pyridine starting material) | 372 | 373 | 67.9 |

-continued

| Ex. No. | Product | Starting material A | Starting material B | Molecular mass calculated | [M + H]+ found | Yield (% of theory) |
|---|---|---|---|---|---|---|
| A345 | | | | 450 | 451 | 77.0 |
| A346 | | | | 427 | 428 | 77.2 |
| A347 | | | | 368 | 369 | 69.5 |

| Ex. No. | Product | Starting material A | Starting material B | Molecular mass calculated | [M + H]+ found | Yield (% of theory) |
|---|---|---|---|---|---|---|
| A348 | (product structure with S-CH2CH2-OH) | Br-CH2CH2-OH | (pyridine-SH starting material) | 372 | 373 | 10.7 |
| A349 | (product structure with S-CH2-C(O)NH2) | Br-CH2-C(O)NH2 | (pyridine-SH starting material) | 385 | 386 | 46.2 |
| A350 | (product structure with S-CH2-CH(OH)-CH3) | Br-CH2-CH(OH)-CH3 | (pyridine-SH starting material) | 386 | 387 | 75.6 |

-continued

| Ex. No. | Product | Starting material A | Starting material B | Molecular mass calculated | [M + H]+ found | Yield (% of theory) |
|---|---|---|---|---|---|---|
| A351 | | methyl bromoacetate | | 400 | 401 | 31.7 |
| A352 | | benzyl bromide | | 418 | 419 | 90.8 |
| A353 | | 3-bromo-1,2-propanediol | | 402 | 403 | 92.4 |

| Ex. No. | Product | Starting material A | Starting material B | Molecular mass calculated | [M + H]+ found | Yield (% of theory) |
|---|---|---|---|---|---|---|
| A354 | (structure) | Br-propyl-OH | (pyridine-thiol structure) | 386 | 387 | 73.2 |
| A355 | (structure) | Br-ethyl-OCH₃ | (pyridine-thiol structure) | 386 | 387 | 55.6 |
| A356 | (structure) | Br-butyl-SO₂NH₂ | (pyridine-thiol structure) | 464 | 465 | 85.4 |

-continued

| Ex. No. | Product | Starting material A | Starting material B | Molecular mass calculated | [M + H]+ found | Yield (% of theory) |
|---|---|---|---|---|---|---|
| A357 | | | | 339 | 340 | 58.9 |
| A358 | | | | 353 | 354 | 89.1 |
| A359 | | | | 367 | 368 | 61.5 |

| Ex. No. | Product | Starting material A | Starting material B | Molecular mass calculated | [M + H]+ found | Yield (% of theory) |
|---|---|---|---|---|---|---|
| A360 | | | | 369 | 370 | 65.2 |
| A361 | | | | 353 | 354 | 61.7 |
| A362 | | | | 431 | 432 | 53.9 |

-continued

| Ex. No. | Product | Starting material A | Starting material B | Molecular mass calculated | [M + H]+ found | Yield (% of theory) |
|---|---|---|---|---|---|---|
| A363 | | | | 408 | 409 | 61.7 |
| A364 | | | | 317 | 318 | 35.9 |
| A365 | | | | 334 | 335 | 24.5 |

-continued

| Ex. No. | Product | Starting material A | Starting material B | Molecular mass calculated | [M + H]+ found | Yield (% of theory) |
|---|---|---|---|---|---|---|
| A366 | (pyridine product with S-CH2-C(O)-O-CH3) | Br-CH2-C(O)-O-CH3 | (pyridine with SH) | 349 | 350 | 41.2 |
| A367 | (pyridine product with S-CH2-phenyl) | Br-CH2-phenyl | (pyridine with SH) | 367 | 368 | 45.2 |
| A368 | (pyridine product with S-(CH2)3-OH) | Br-(CH2)3-OH | (pyridine with SH) | 335 | 336 | 50.1 |

| Ex. No. | Product | Starting material A | Starting material B | Molecular mass calculated | [M + H]+ found | Yield (% of theory) |
|---|---|---|---|---|---|---|
| A369 | | | | 343 | 344 | 75.6 |
| A370 | | | | 347 | 348 | 89.4 |
| A371 | | | | 360 | 361 | 81.7 |

| Ex. No. | Product | Starting material A | Starting material B | Molecular mass calculated | [M + H]+ found | Yield (% of theory) |
|---|---|---|---|---|---|---|
| A372 | (product structure) | 1-bromo-2-hydroxypropane | (pyridine starting material) | 361 | 362 | 89.0 |
| A373 | (product structure) | methyl bromoacetate | (pyridine starting material) | 375 | 376 | 60.8 |
| A374 | (product structure) | benzyl bromide | (pyridine starting material) | 393 | 394 | 69.5 |

-continued

| Ex. No. | Product | Starting material A | Starting material B | Molecular mass calculated | [M + H]+ found | Yield (% of theory) |
|---|---|---|---|---|---|---|
| A375 | (structure) | Br-(CH2)3-OH | (structure) | 361 | 362 | 21.9 |
| A376 | (structure) | Br-CH2CH2-O-CH3 | (structure) | 361 | 362 | 56.5 |
| A377 | (structure) | Br-(CH2)4-SO2NH2 | (structure) | 438 | 439 | 90.7 |

| Ex. No. | Product | | Starting material A | | Starting material B | Molecular mass calculated | [M + H]+ found | Yield (% of theory) |
|---|---|---|---|---|---|---|---|---|
| A378 | (structure) | | (structure) | (TFA) | (chloromethyl-1-methylimidazole·HCl) | 476 | 477 | 40.3 |
| A379 | (structure) | | (structure) | (TFA) | (bromomethylimidazole·HBr) | 462 | 463 | 16.4 |
| A380 | (structure) | | (structure with morpholinium) | (TFA) | (bromomethylimidazole·HBr) | 446 | 447 | 71.7 |

-continued

| Ex. No. | Product | Starting material A | Starting material B | Molecular mass calculated | [M + H]+ found | Yield (% of theory) |
|---|---|---|---|---|---|---|
| A381 | (3-bromophenyl pyridine with S-CH2-C(O)NH2) | 4-(3-bromophenyl)-pyridine with SH, CN, NH2 | BrCH2C(O)NH2 | 388 | 389 | 74.2 |
| A382 | (4-hydroxyphenyl pyridine with S-CH2-CH=C(CH3)2) | 4-(4-hydroxyphenyl)-pyridine with SH, CN, NH2; N-methylmorpholine | prenyl bromide | 336 | 337 | 76.4 |
| A383 | (4-hydroxyphenyl pyridine with S-CH2-(4-fluorophenyl)) | 4-(4-hydroxyphenyl)-pyridine with SH, CN, NH2; N-methylmorpholine | 4-fluorobenzyl bromide | 376 | 377 | 68.3 |

| Ex. No. | Product | Starting material A | | Starting material B | Molecular mass calculated | [M + H]+ found | Yield (% of theory) |
|---|---|---|---|---|---|---|---|
| A384 | (3-fluorobenzyl thioether pyridine product) | (pyridine-SH starting material) | N-methylmorpholine | 3-fluorobenzyl bromide | 376 | 377 | 66.4 |
| A385 | (3-methoxybenzyl thioether pyridine product) | (pyridine-SH starting material) | N-methylmorpholine | 3-methoxybenzyl bromide | 388 | 389 | 64.9 |
| A386 | (5-nitrofurfuryl thioether pyridine product) | (pyridine-SH starting material) | N-methylmorpholine | 5-nitrofurfuryl bromide | 393 | 394 | 57.7 |

| Ex. No. | Product | Starting material A | | Starting material B | Molecular mass calculated | [M + H]+ found | Yield (% of theory) |
|---|---|---|---|---|---|---|---|
| A387 | (structure) | (structure) | (N-methylmorpholine) | (structure) | 431 | 432 | 23.4 |
| A388 | (structure) | (structure) | (N-methylmorpholine) | (structure) | 400 | 401 | 46.5 |
| A389 | (structure) | (structure) | (N-methylmorpholine) | (structure) | 456 | 457 | 5.5 |

-continued

| Ex. No. | Product | Starting material A | | Starting material B | Molecular mass calculated | [M + H]+ found | Yield (% of theory) |
|---|---|---|---|---|---|---|---|
| A390 | | | (N-methylmorpholine) | | 386 | 387 | 62.9 |
| A391 | | | (N-methylmorpholine) | | 403 | 404 | 60.2 |
| A392 | | | (N-methylmorpholine) | | 416 | 417 | 18.0 |

-continued

| Ex. No. | Product | Starting material A | | Starting material B | Molecular mass calculated | [M + H]+ found | Yield (% of theory) |
|---|---|---|---|---|---|---|---|
| A393 | (product structure) | (pyridine structure) | N-methylmorpholine | 3-(bromomethyl)benzonitrile | 383 | 384 | 55.6 |
| A394 | (product structure) | (pyridine structure) | N-methylmorpholine | 2-(bromomethyl)-1-(difluoromethoxy)benzene | 424 | 425 | 56.5 |
| A395 | (product structure) | (pyridine structure) | N-methylmorpholine | 3-{[(4-methylphenyl)sulfonyl]methyl}benzyl bromide | 527 | 528 | 67.8 |

-continued

| Ex. No. | Product | Starting material A | Starting material B | Molecular mass calculated | [M + H]+ found | Yield (% of theory) |
|---|---|---|---|---|---|---|
| A396 | (product structure) | (structure) | 4-(bromomethyl)benzonitrile | 367 | 368 | 13.6 |
| A397 | (product structure) | (structure) | 3-(bromomethyl)pyridine·HBr | 343 | 344 | 23.6 |
| A398 | (product structure) | (structure) | 2-chloro-4-(chloromethyl)thiazole | 384 | 385 | 15.6 |

-continued

| Ex. No. | Product | Starting material A | Starting material B | Molecular mass calculated | [M + H]+ found | Yield (% of theory) |
|---|---|---|---|---|---|---|
| A399 | | | | 367 | 368 | 72.4 |
| A400 | | | | 367 | 368 | 7.1 |
| A401 | | | | 408 | 409 | 78.1 |

-continued

| Ex. No. | Product | Starting material A | Starting material B | Molecular mass calculated | [M + H]+ found | Yield (% of theory) |
|---|---|---|---|---|---|---|
| A402 | | | | 511 | 512 | 45.0 |
| A403 | | | | 380 | 381 | 21.8 |
| A404 | | | | 399 | 400 | 47.3 |

| Ex. No. | Product | Starting material A | Starting material B | Molecular mass calculated | [M + H]+ found | Yield (% of theory) |
|---|---|---|---|---|---|---|
| A405 | (structure with S-CH2CH2-OH, pyridine with CN, NH2, CN, phenyl-NHC(O)CH3) | (acetamidophenyl pyridine with CN, SH, CN, NH2) | 2-bromoethanol | 353 | 354 | 56.6 |
| A406 | (structure with S-CH2CH2-OCH3, pyridine with CN, NH2, CN, phenyl-NHC(O)CH3) | (acetamidophenyl pyridine with CN, SH, CN, NH2) | 2-bromoethanol | 367 | 368 | 43.3 |

-continued

| Ex. No. | Product | Starting material A | Starting material B | Molecular mass calculated | [M + H]+ found | Yield (% of theory) |
|---|---|---|---|---|---|---|
| A407 | | | | 367 | 368 | 49.8 |
| A408 | | | | 364 | 365 | 68.6 |
| A409 | | | | 446 | 447 | 57.3 |

| Ex. No. | Product | Starting material A | Starting material B | Molecular mass calculated | [M + H]+ found | Yield (% of theory) |
|---|---|---|---|---|---|---|
| A410 | | | | 377 | 378 | 15.5 |
| A411 | | | | 332 | 333 | 35.4 |

| Ex. No. | Product | Starting material A | Starting material B | Molecular mass calculated | [M + H]+ found | Yield (% of theory) |
|---|---|---|---|---|---|---|
| A412 | 2-amino-6-[(2-methoxyethyl)thio]-4-phenylpyridine-3,5-dicarbonitrile | 2-amino-6-mercapto-4-phenylpyridine-3,5-dicarbonitrile | MeO-CH2CH2-Br | 310 | 311 | 86.4 |
| A413 | 2-amino-4-(3-hydroxyphenyl)-6-[(2-methoxyethyl)thio]pyridine-3,5-dicarbonitrile | 2-amino-4-(3-hydroxyphenyl)-6-mercaptopyridine-3,5-dicarbonitrile | MeO-CH2CH2-Br | 326 | 327 | 46.4 |

| Ex. No. | Product | Molecular weight |
|---|---|---|
| B1 | | 419 |
| B2 | | 465 |
| B3 | | 439 |
| B4 | | 465 |

-continued
| Ex. No. | Product | Molecular weight |
|---|---|---|
| B5 | 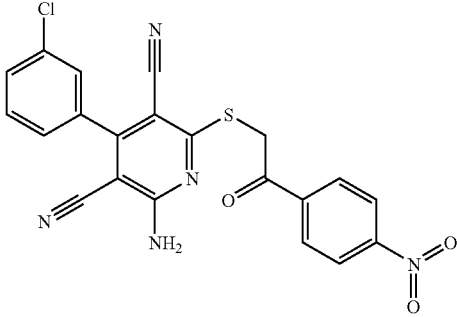 | 450 |
| B6 | 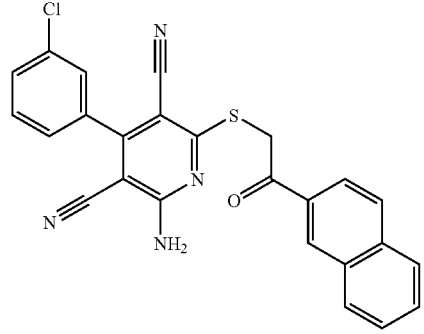 | 455 |
| B7 | 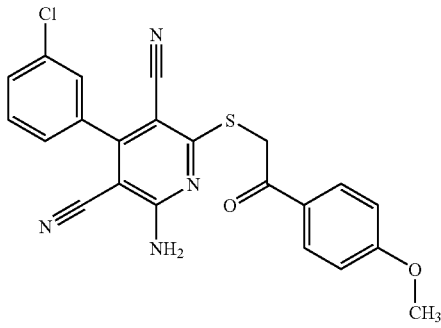 | 435 |
| B8 | 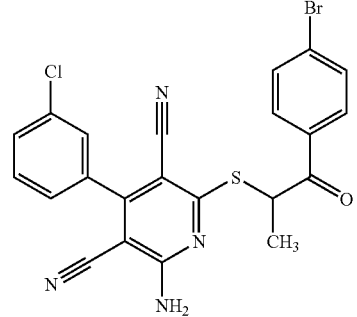 | 498 |

-continued

| Ex. No. | Product | Molecular weight |
|---|---|---|
| B9 | 4-(3-chlorophenyl)-2-amino-6-[(1-methyl-2-oxo-2-phenylethyl)thio]-3,5-pyridinedicarbonitrile | 419 |
| B10 | 4-(3-chlorophenyl)-2-amino-6-{[2-(4-bromophenyl)-2-oxoethyl]thio}-3,5-pyridinedicarbonitrile | 484 |
| B11 | 4-(3-chlorophenyl)-2-amino-6-{[2-oxo-2-(pyridin-4-yl)ethyl]thio}-3,5-pyridinedicarbonitrile | 406 |
| B12 | 4-(3-chlorophenyl)-2-amino-6-{[2-oxo-2-(pyridin-2-yl)ethyl]thio}-3,5-pyridinedicarbonitrile | 406 |
| B13 | 4-(3-chlorophenyl)-2-amino-6-{[1-(4-methoxyphenyl)-2-(4-methoxyphenyl)-2-oxoethyl]thio}-3,5-pyridinedicarbonitrile | 541 |

-continued

| Ex. No. | Product | Molecular weight |
|---|---|---|
| B14 | | 481 |
| B15 | | 423 |
| B16 | | 473 |
| B17 | | 474 |
| B18 | | 450 |

-continued

| Ex. No. | Product | Molecular weight |
|---|---|---|
| B19 | | 515 |
| B20 | | 439 |
| B21 | | 474 |
| B22 | | 430 |
| B23 | | 434 |

| Ex. No. | Product | Molecular weight |
|---|---|---|
| B24 | | 443 |
| B25 | | 507 |
| B26 | | 406 |
| B27 | | 469 |
| B28 | | 515 |

-continued

| Ex. No. | Product | Molecular weight |
|---|---|---|
| B29 | | 540 |
| B30 | | 476 |
| B31 | | 463 |
| B32 | | 497 |
| B33 | | 461 |

-continued
| Ex. No. | Product | Molecular weight |
|---|---|---|
| B34 | 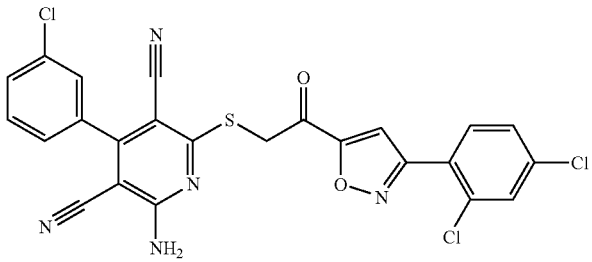 | 541 |
| B35 | 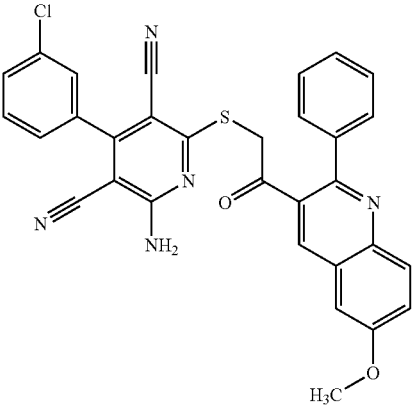 | 562 |
| B36 | 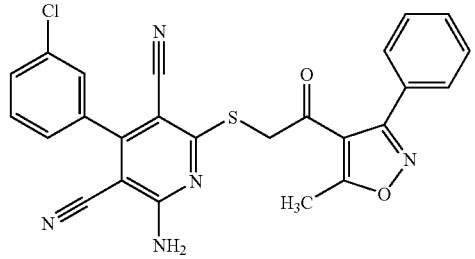 | 486 |
| B37 | 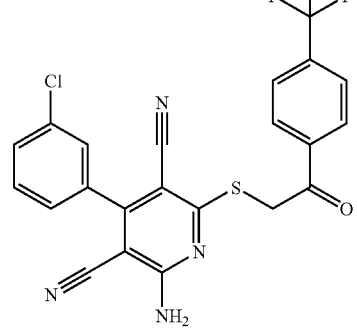 | 473 |

-continued

| Ex. No. | Product | Molecular weight |
|---|---|---|
| B38 | | 373 |
| B39 | | 434 |
| B40 | | 560 |
| B41 | | 433 |

-continued

| Ex. No. | Product | Molecular weight |
|---|---|---|
| B42 | | 474 |
| B43 | | 451 |
| B44 | | 515 |
| B45 | | 419 |

-continued

| Ex. No. | Product | Molecular weight |
|---|---|---|
| B46 | (structure) | 556 |
| B47 | (structure) | 369 |
| B48 | (structure) | 631 |
| B49 | (structure) | 550 |

-continued

| Ex. No. | Product | Molecular weight |
|---|---|---|
| B50 | | 492 |
| B51 | | 545 |
| B52 | | 515 |
| B53 | | 479 |

-continued

| Ex. No. | Product | Molecular weight |
|---|---|---|
| B54 | | 484 |
| B55 | | 381 |
| B56 | | 527 |
| B57 | | 417 |
| B58 | | 396 |

| Ex. No. | Product | Molecular weight |
|---|---|---|
| B59 | 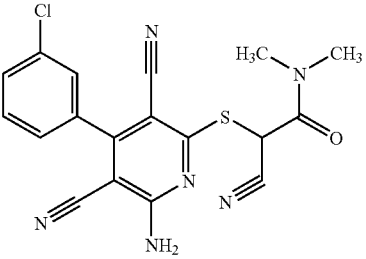 | 397 |
| B60 | 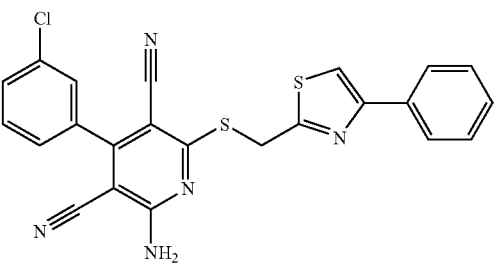 | 460 |
| B61 | 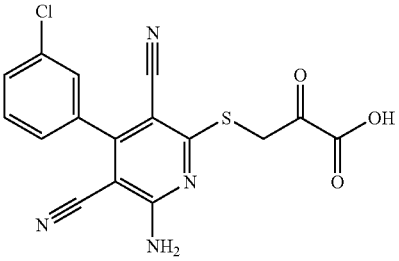 | 373 |
| B62 | 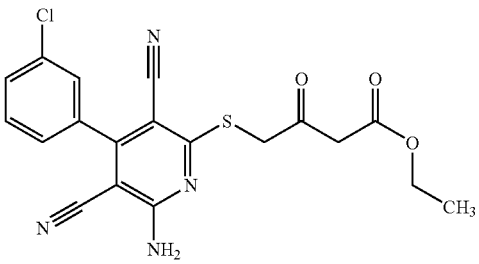 | 415 |
| B63 | 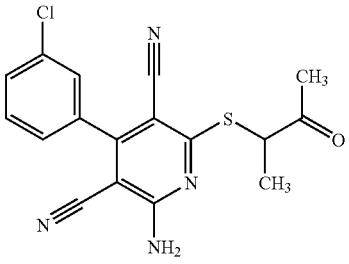 | 357 |

| Ex. No. | Product | Molecular weight |
|---|---|---|
| B64 | | 400 |
| B65 | | 384 |
| B66 | | 430 |
| B67 | | 430 |
| B68 | | 400 |

| Ex. No. | Product | Molecular weight |
|---|---|---|
| B69 | 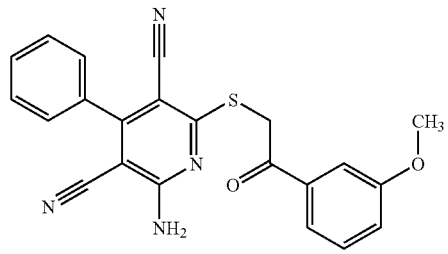 | 400 |
| B70 | 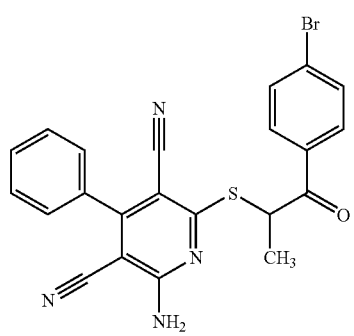 | 463 |
| B71 | 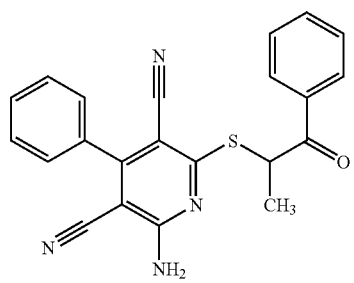 | 384 |
| B72 | 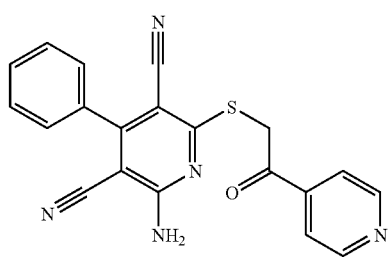 | 371 |
| B73 | 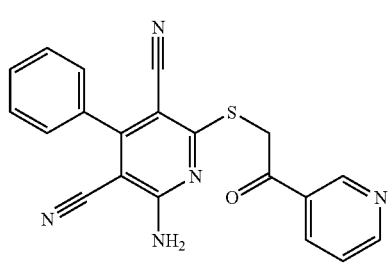 | 371 |

-continued

| Ex. No. | Product | Molecular weight |
|---|---|---|
| B74 | | 371 |
| B75 | | 447 |
| B76 | | 388 |
| B77 | | 438 |
| B78 | | 415 |

-continued

| Ex. No. | Product | Molecular weight |
|---|---|---|
| B79 | | 408 |
| B80 | | 473 |
| B81 | | 371 |
| B82 | | 434 |
| B83 | | 481 |

-continued

| Ex. No. | Product | Molecular weight |
|---|---|---|
| B84 | | 442 |
| B85 | | 428 |
| B86 | | 463 |
| B87 | | 528 |

-continued

| Ex. No. | Product | Molecular weight |
|---|---|---|
| B88 | (structure) | 452 |
| B89 | (structure) | 438 |
| B90 | (structure) | 338 |
| B91 | (structure) | 399 |
| B92 | (structure) | 398 |

-continued

| Ex. No. | Product | Molecular weight |
|---------|---------|------------------|
| B93 | | 417 |
| B94 | | 481 |
| B95 | | 384 |
| B96 | | 334 |
| B97 | | 516 |

-continued
| Ex. No. | Product | Molecular weight |
|---|---|---|
| B98 | 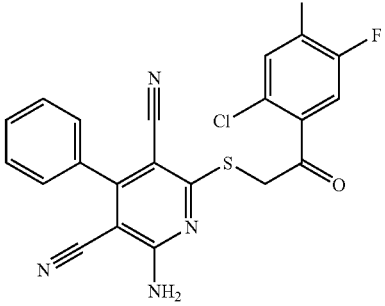 | 457 |
| B99 | 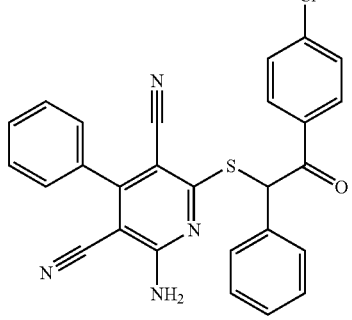 | 481 |
| B100 | 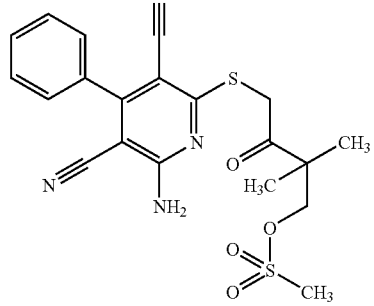 | 445 |
| B101 | 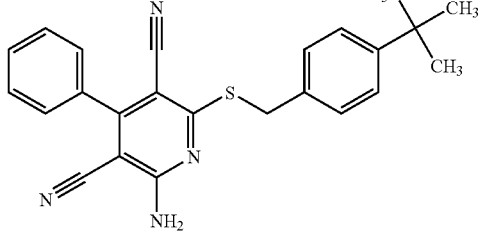 | 399 |
| B102 | 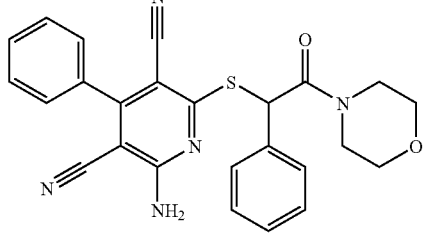 | 456 |

-continued
| Ex. No. | Product | Molecular weight |
|---|---|---|
| B103 | 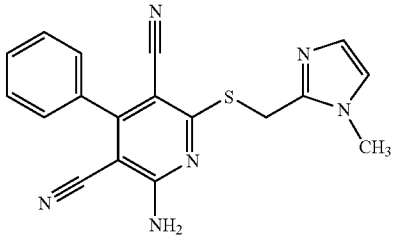 | 346 |
| B104 | 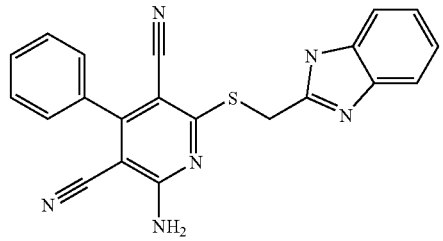 | 382 |
| B105 | 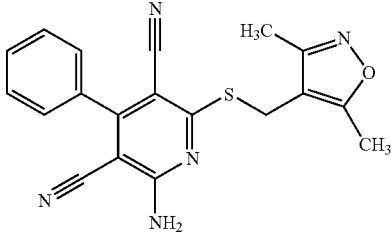 | 361 |
| B106 | 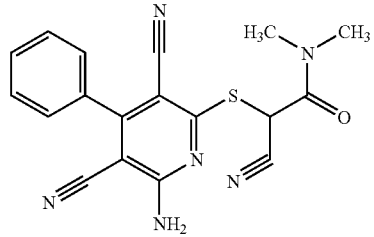 | 362 |
| B107 | 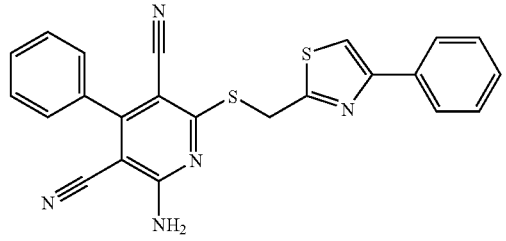 | 426 |
| B108 | 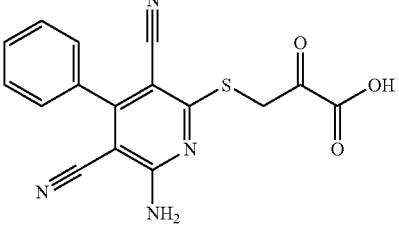 | 338 |

-continued

| Ex. No. | Product | Molecular weight |
|---|---|---|
| B109 | | 380 |
| B110 | | 322 |
| B111 | | 379 |
| B112 | | 435 |
| B113 | | 419 |

-continued

| Ex. No. | Product | Molecular weight |
|---|---|---|
| B114 | | 465 |
| B115 | | 465 |
| B116 | | 498 |
| B117 | | 419 |
| B118 | | 406 |

-continued
| Ex. No. | Product | Molecular weight |
|---|---|---|
| B119 | 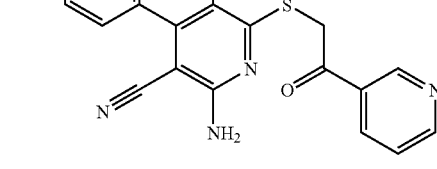 | 406 |
| B120 | 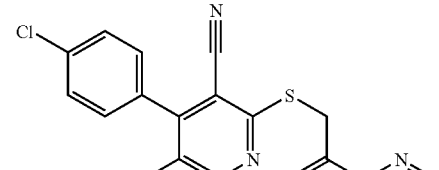 | 406 |
| B121 | 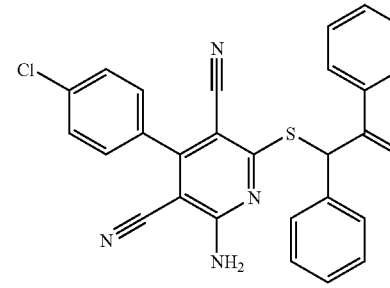 | 481 |
| B122 | 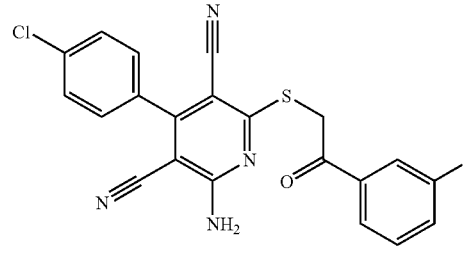 | 423 |
| B123 | 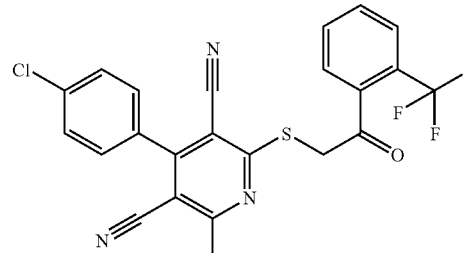 | 473 |

-continued
| Ex. No. | Product | Molecular weight |
|---|---|---|
| B124 | 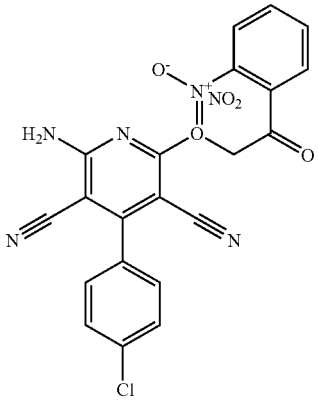 | 450 |
| B125 | 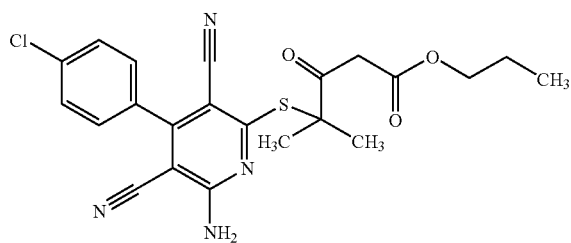 | 443 |
| B126 | 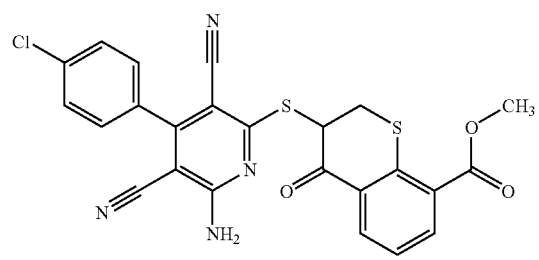 | 507 |
| B127 | 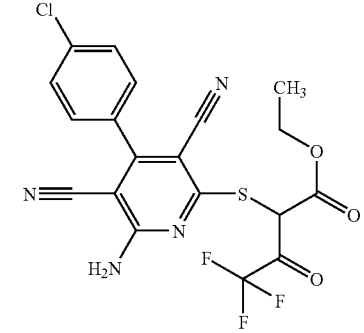 | 469 |

| Ex. No. | Product | Molecular weight |
|---|---|---|
| B128 | 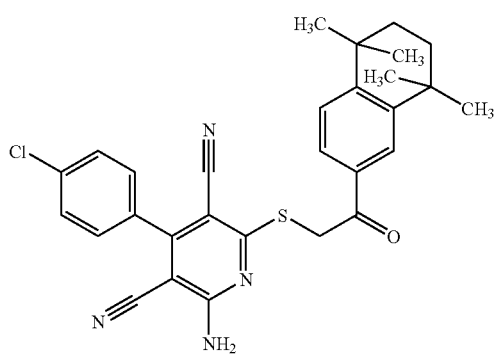 | 515 |
| B129 | 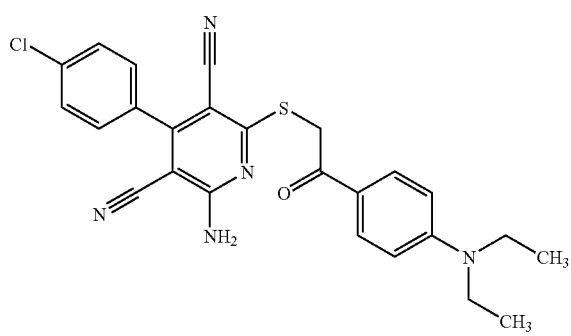 | 476 |
| B130 | 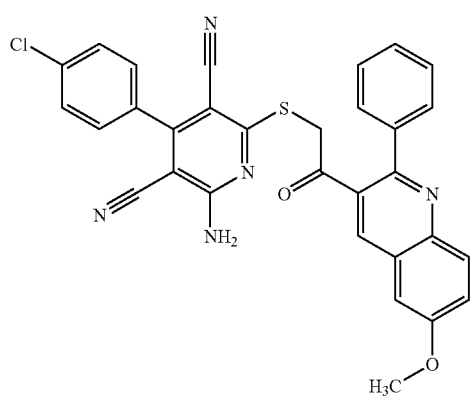 | 562 |
| B131 | 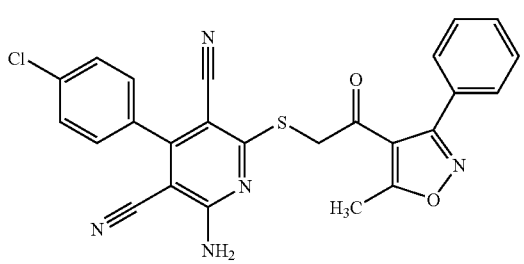 | 486 |

-continued

| Ex. No. | Product | Molecular weight |
|---|---|---|
| B132 | | 473 |
| B133 | | 373 |
| B134 | | 434 |
| B135 | | 451 |

| Ex. No. | Product | Molecular weight |
|---|---|---|
| B136 | | 515 |
| B137 | | 415 |
| B138 | | 419 |
| B139 | | 369 |

-continued

| Ex. No. | Product | Molecular weight |
|---|---|---|
| B140 | | 492 |
| B141 | | 484 |
| B142 | | 427 |
| B143 | | 381 |
| B144 | | 417 |

-continued

| Ex. No. | Product | Molecular weight |
|---|---|---|
| B145 | | 396 |
| B146 | | 397 |
| B147 | | 460 |
| B148 | | 373 |
| B149 | | 357 |
| B150 | | 414 |

| Ex. No. | Product | Molecular weight |
|---|---|---|
| B151 | | 416 |
| B152 | | 416 |
| B153 | | 416 |
| B154 | | 444 |
| B155 | | 453 |

-continued

| Ex. No. | Product | Molecular weight |
|---|---|---|
| B156 | | 550 |
| B157 | | 573 |
| B158 | | 444 |
| B159 | | 462 |

-continued

| Ex. No. | Product | Molecular weight |
|---|---|---|
| B160 | | 425 |
| B161 | | 494 |
| B162 | | 602 |
| B163 | | 391 |
| B164 | | 427 |

-continued

| Ex. No. | Product | Molecular weight |
|---|---|---|
| B165 | | 407 |
| B166 | | 471 |
| B167 | | 424 |
| B168 | | 430 |
| B169 | | 461 |

-continued

| Ex. No. | Product | Molecular weight |
|---|---|---|
| B170 | | 435 |
| B171 | | 461 |
| B172 | | 445 |
| B173 | | 451 |

-continued

| Ex. No. | Product | Molecular weight |
|---|---|---|
| B174 | (structure) | 430 |
| B175 | (structure) | 430 |
| B176 | (structure) | 493 |
| B177 | (structure) | 414 |
| B178 | (structure) | 401 |

-continued

| Ex. No. | Product | Molecular weight |
|---|---|---|
| B179 | (structure) | 401 |
| B180 | (structure) | 401 |
| B181 | (structure) | 477 |
| B182 | (structure) | 418 |
| B183 | (structure) | 468 |

-continued
| Ex. No. | Product | Molecular weight |
|---|---|---|
| B184 | 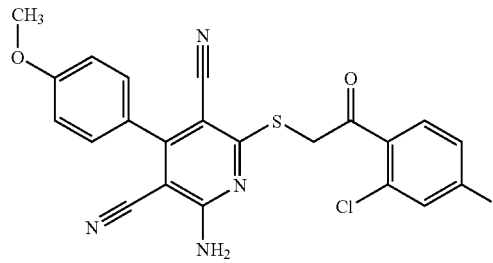 | 469 |
| B185 | 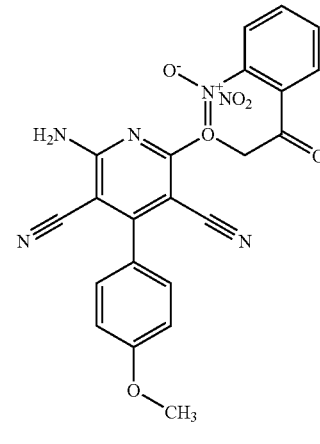 | 445 |
| B186 | 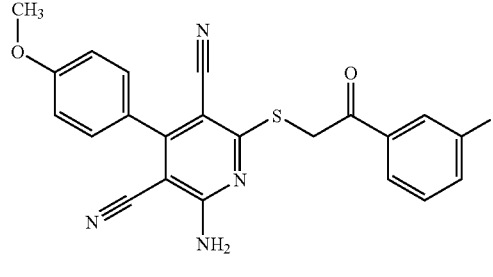 | 435 |
| B187 | 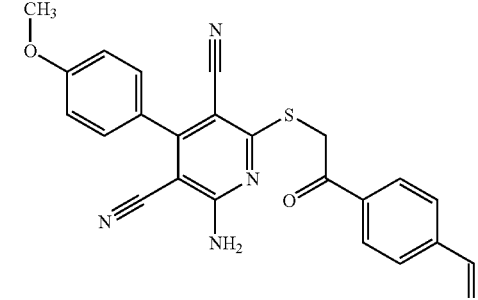 | 425 |

-continued

| Ex. No. | Product | Molecular weight |
|---------|---------|------------------|
| B188 | | 430 |
| B189 | | 439 |
| B190 | | 503 |
| B191 | | 401 |
| B192 | | 425 |

-continued

| Ex. No. | Product | Molecular weight |
|---|---|---|
| B193 | | 464 |
| B194 | | 511 |
| B195 | | 472 |
| B196 | | 458 |

-continued

| Ex. No. | Product | Molecular weight |
|---|---|---|
| B197 | | 493 |
| B198 | | 457 |
| B199 | | 558 |
| B200 | | 482 |

-continued
| Ex. No. | Product | Molecular weight |
|---|---|---|
| B201 | 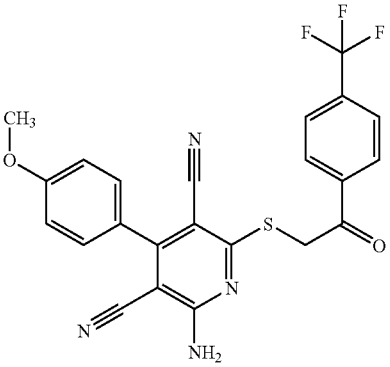 | 468 |
| B202 | 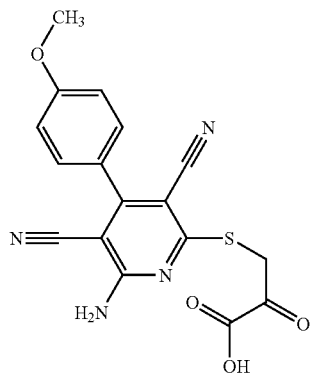 | 368 |
| B203 | 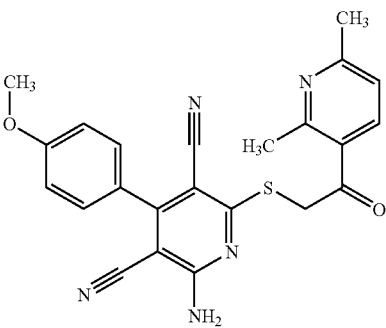 | 430 |
| B204 | 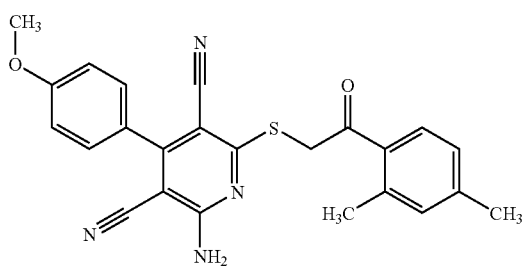 | 429 |

-continued

| Ex. No. | Product | Molecular weight |
|---|---|---|
| B205 | | 469 |
| B206 | | 447 |
| B207 | | 511 |
| B208 | | 364 |

| Ex. No. | Product | Molecular weight |
|---|---|---|
| B209 | | 546 |
| B210 | | 487 |
| B211 | | 475 |
| B212 | | 480 |

-continued

| Ex. No. | Product | Molecular weight |
|---|---|---|
| B213 | (structure) | 493 |
| B214 | (structure) | 479 |
| B215 | (structure) | 423 |
| B216 | (structure) | 429 |
| B217 | (structure) | 486 |

-continued

| Ex. No. | Product | Molecular weight |
|---|---|---|
| B218 | | 605 |
| B219 | | 376 |
| B220 | | 412 |
| B221 | | 391 |
| B222 | | 392 |

-continued
| Ex. No. | Product | Molecular weight |
|---|---|---|
| B223 | 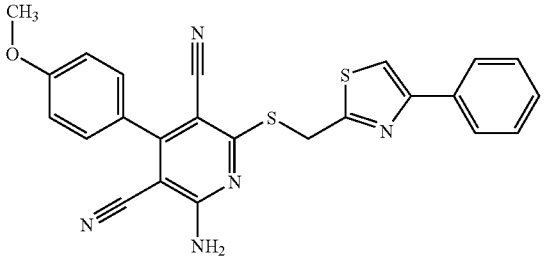 | 456 |
| B224 | 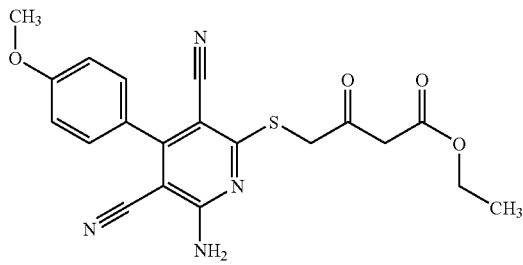 | 410 |
| B225 | 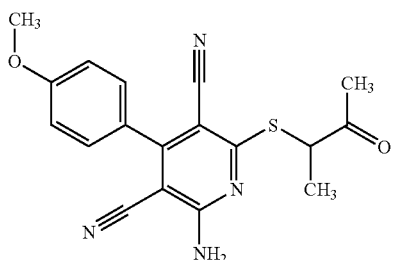 | 352 |
| B226 | 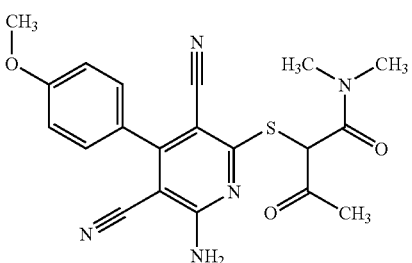 | 409 |
| B227 | 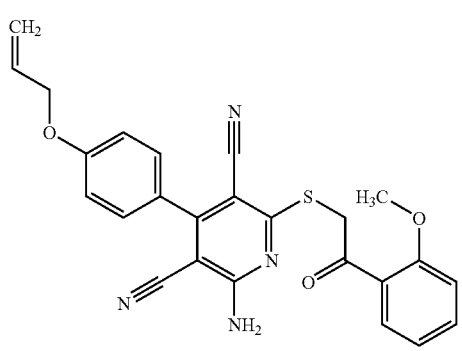 | 457 |

-continued

| Ex. No. | Product | Molecular weight |
|---|---|---|
| B228 | | 441 |
| B229 | | 487 |
| B230 | | 487 |
| B231 | | 457 |

| Ex. No. | Product | Molecular weight |
|---|---|---|
| B232 | | 457 |
| B233 | | 441 |
| B234 | | 427 |
| B235 | | 427 |

| Ex. No. | Product | Molecular weight |
|---|---|---|
| B236 | 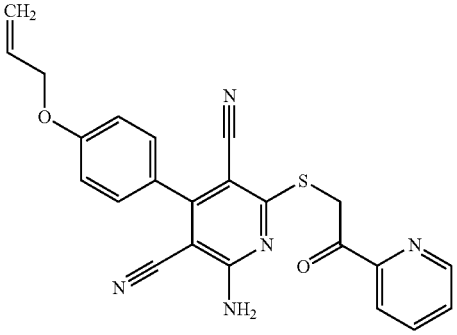 | 427 |
| B237 | 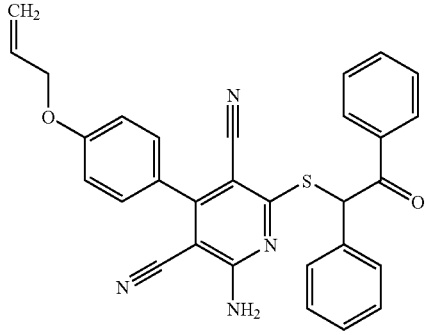 | 503 |
| B238 | 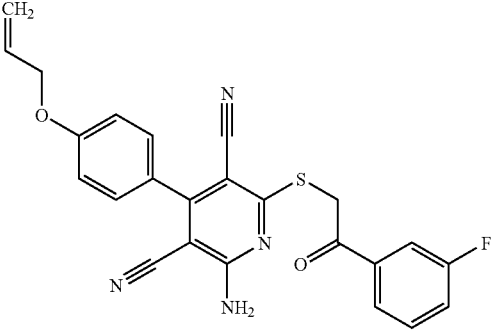 | 444 |
| B239 | 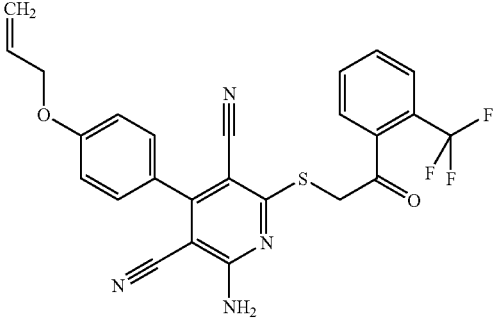 | 494 |

-continued
| Ex. No. | Product | Molecular weight |
|---|---|---|
| B240 | 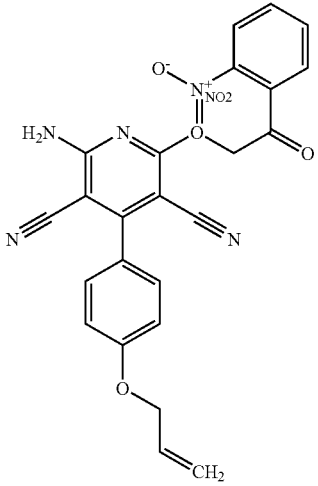 | 471 |
| B241 | 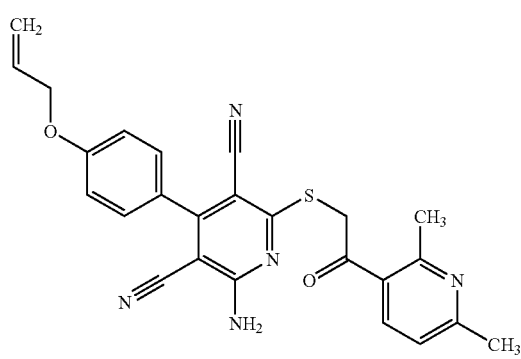 | 456 |
| B242 | 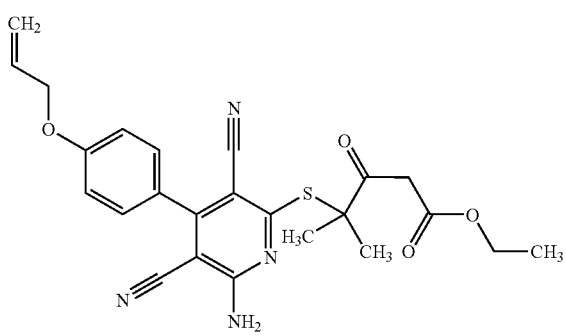 | 465 |
| B243 | 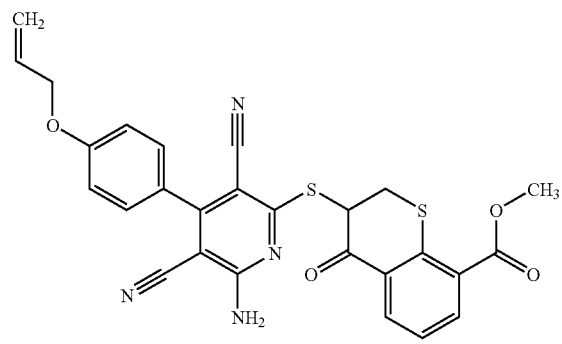 | 529 |

-continued

| Ex. No. | Product | Molecular weight |
|---|---|---|
| B244 | | 427 |
| B245 | | 490 |
| B246 | | 498 |
| B247 | | 485 |

-continued

| Ex. No. | Product | Molecular weight |
|---|---|---|
| B248 | (structure) | 519 |
| B249 | (structure) | 584 |
| B250 | (structure) | 456 |
| B251 | (structure) | 455 |

| Ex. No. | Product | Molecular weight |
|---|---|---|
| B252 | (structure) | 473 |
| B253 | (structure) | 537 |
| B254 | (structure) | 441 |
| B255 | (structure) | 390 |

-continued
| Ex. No. | Product | Molecular weight |
|---|---|---|
| B256 | 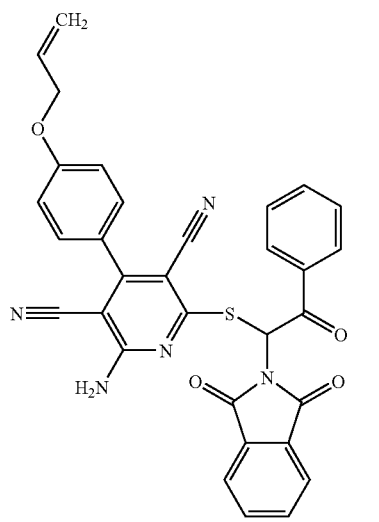 | 572 |
| B257 | 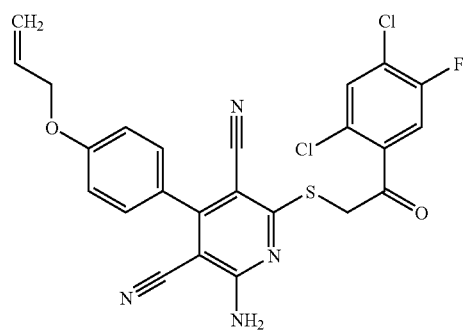 | 513 |
| B258 | 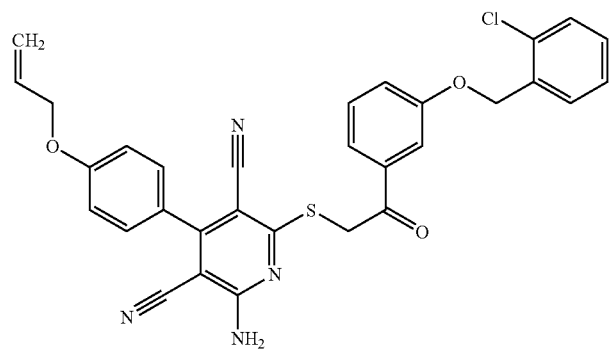 | 567 |

-continued

| Ex. No. | Product | Molecular weight |
|---|---|---|
| B259 | | 501 |
| B260 | | 443 |
| B261 | | 455 |
| B262 | | 512 |

| Ex. No. | Product | Molecular weight |
|---|---|---|
| B263 | 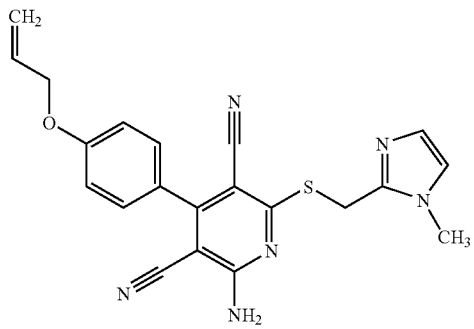 | 402 |
| B264 | 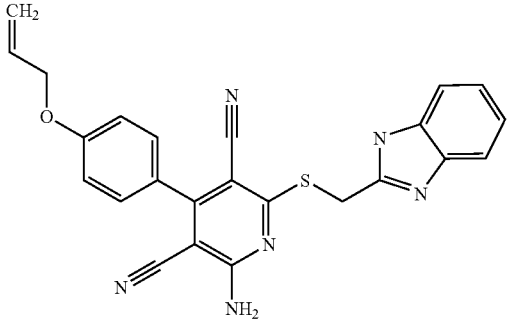 | 439 |
| B265 | 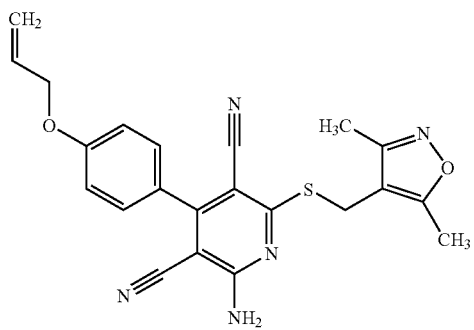 | 417 |
| B266 | 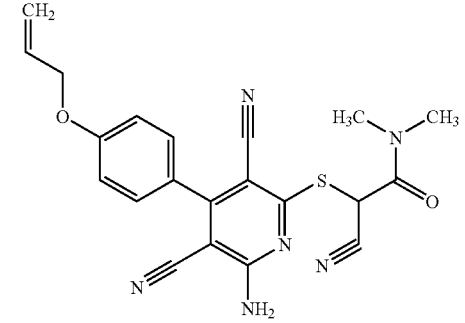 | 418 |

-continued

| Ex. No. | Product | Molecular weight |
|---|---|---|
| B267 | | 482 |
| B268 | | 394 |
| B269 | | 436 |
| B270 | | 414 |
| B271 | | 461 |

-continued
| Ex. No. | Product | Molecular weight |
|---|---|---|
| B272 | 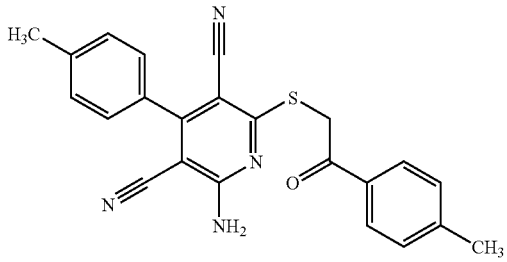 | 398 |
| B273 | 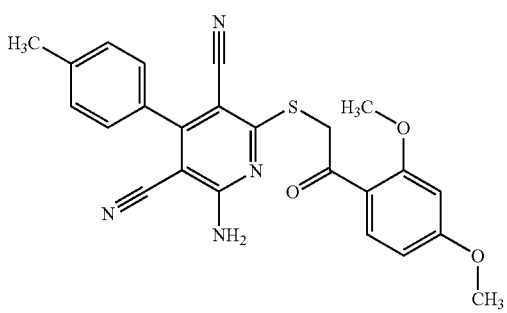 | 445 |
| B274 | 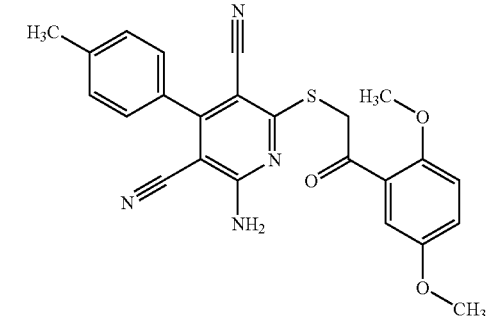 | 445 |
| B275 | 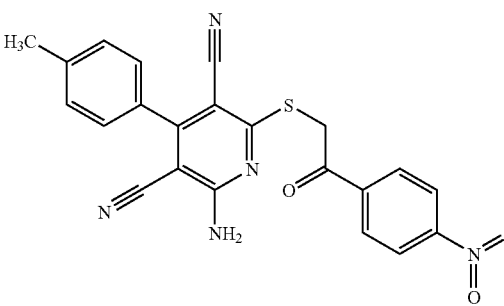 | 429 |
| B276 | 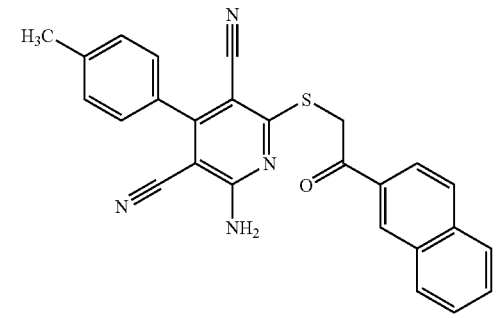 | 435 |

| Ex. No. | Product | Molecular weight |
|---|---|---|
| B277 | 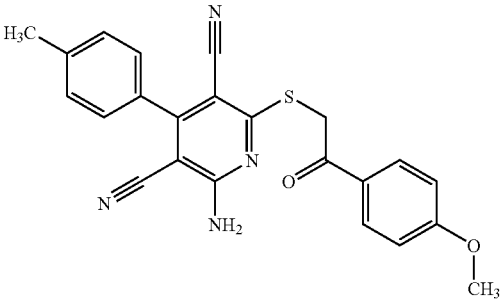 | 414 |
| B278 | 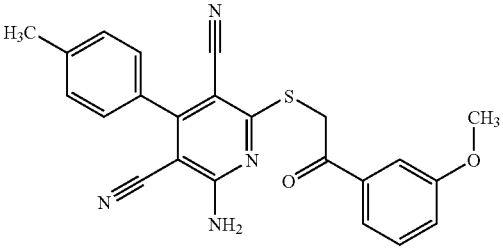 | 414 |
| B279 | 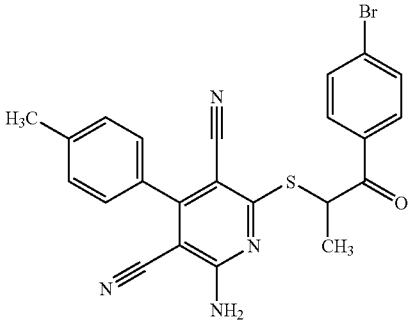 | 477 |
| B280 | 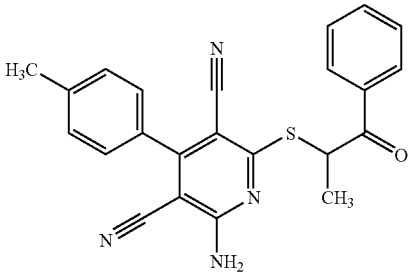 | 398 |
| B281 | 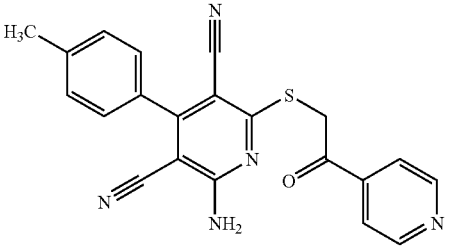 | 385 |

-continued

| Ex. No. | Product | Molecular weight |
|---|---|---|
| B282 | | 385 |
| B283 | | 385 |
| B284 | | 461 |
| B285 | | 402 |
| B286 | | 452 |

-continued

| Ex. No. | Product | Molecular weight |
|---|---|---|
| B287 | | 453 |
| B288 | | 429 |
| B289 | | 419 |
| B290 | | 409 |
| B291 | | 414 |

-continued

| Ex. No. | Product | Molecular weight |
|---|---|---|
| B292 | | 423 |
| B293 | | 487 |
| B294 | | 385 |
| B295 | | 409 |
| B296 | | 448 |

-continued
| Ex. No. | Product | Molecular weight |
|---|---|---|
| B297 | 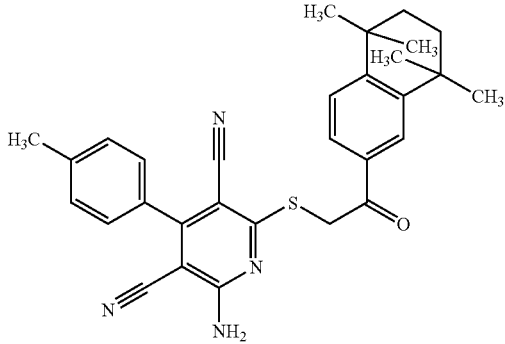 | 495 |
| B298 | 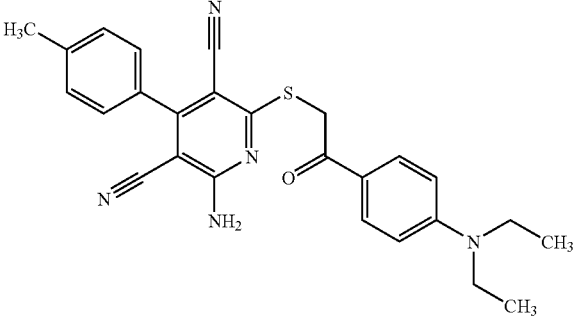 | 456 |
| B299 | 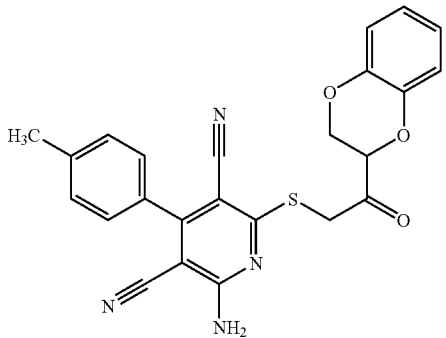 | 443 |
| B300 | 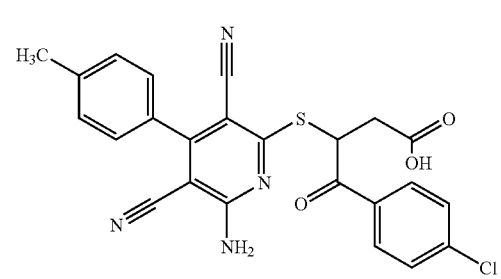 | 477 |

-continued

| Ex. No. | Product | Molecular weight |
|---|---|---|
| B301 | (structure) | 542 |
| B302 | (structure) | 466 |
| B303 | (structure) | 452 |
| B304 | (structure) | 352 |

-continued

| Ex. No. | Product | Molecular weight |
|---|---|---|
| B305 | | 414 |
| B306 | | 413 |
| B307 | | 453 |
| B308 | | 431 |
| B309 | | 495 |

-continued

| Ex. No. | Product | Molecular weight |
|---|---|---|
| B310 | | 398 |
| B311 | | 348 |
| B312 | | 611 |
| B313 | | 530 |

-continued
| Ex. No. | Product | Molecular weight |
|---|---|---|
| B314 | 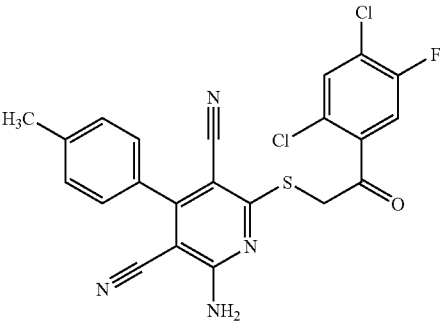 | 471 |
| B315 | 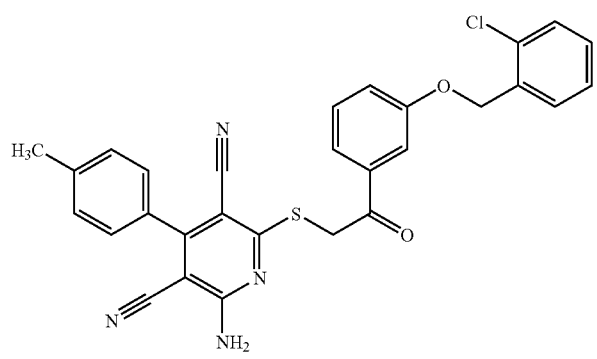 | 525 |
| B316 | 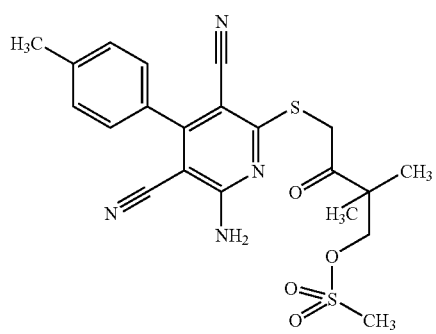 | 459 |
| B317 | 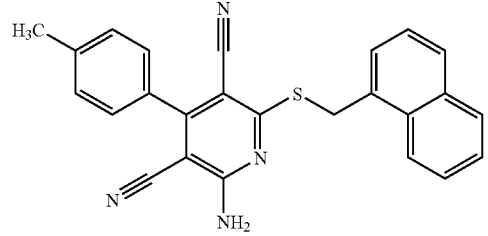 | 407 |

| Ex. No. | Product | Molecular weight |
|---|---|---|
| B318 | 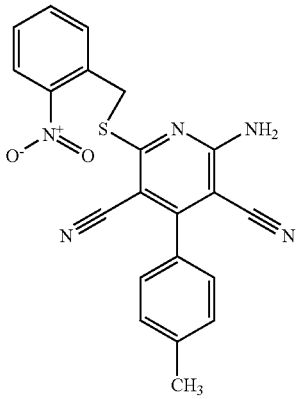 | 401 |
| B319 | 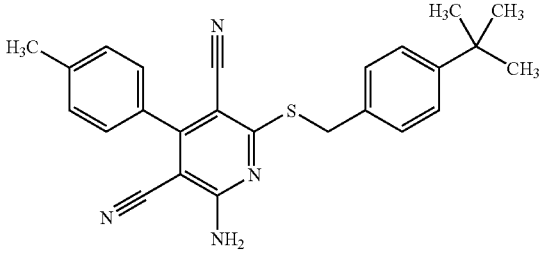 | 413 |
| B320 | 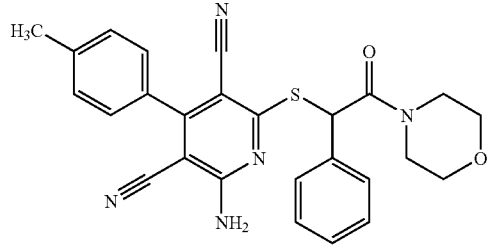 | 470 |
| B321 | 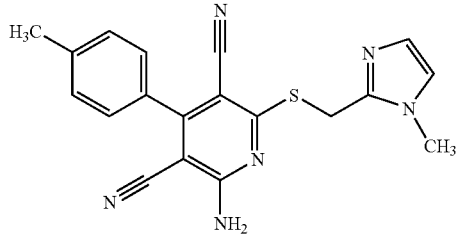 | 360 |
| B322 | 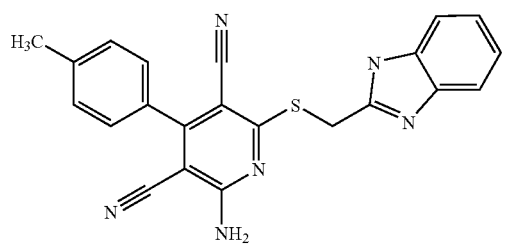 | 396 |

-continued

| Ex. No. | Product | Molecular weight |
|---|---|---|
| B323 | | 375 |
| B324 | | 376 |
| B325 | | 440 |
| B326 | | 414 |
| B327 | | 352 |
| B328 | | 394 |

-continued

| Ex. No. | Product | Molecular weight |
|---|---|---|
| B329 | | 336 |
| B330 | | 393 |
| B331 | | 435 |
| B332 | | 419 |
| B333 | | 465 |

-continued
| Ex. No. | Product | Molecular weight |
|---|---|---|
| B334 | 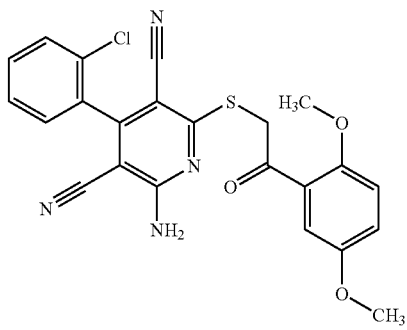 | 465 |
| B335 | 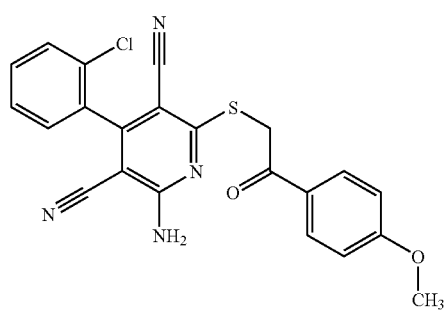 | 435 |
| B336 | 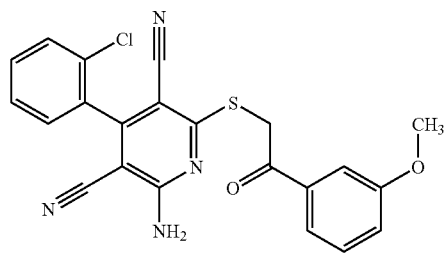 | 435 |
| B337 | 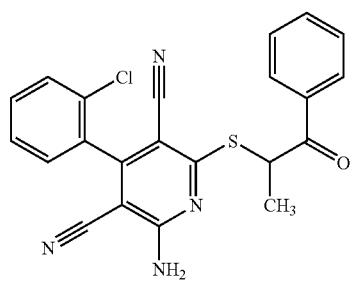 | 419 |
| B338 | 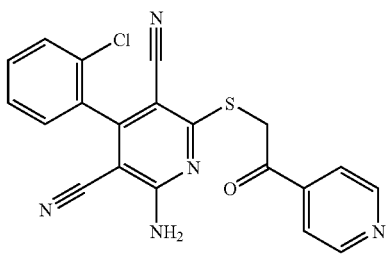 | 406 |

-continued

| Ex. No. | Product | Molecular weight |
|---|---|---|
| B339 | | 406 |
| B340 | | 406 |
| B341 | | 481 |
| B342 | | 423 |
| B343 | | 473 |

-continued

| Ex. No. | Product | Molecular weight |
|---|---|---|
| B344 | | 434 |
| B345 | | 443 |
| B346 | | 406 |
| B347 | | 469 |
| B348 | | 515 |

| Ex. No. | Product | Molecular weight |
|---|---|---|
| B349 | | 476 |
| B350 | | 562 |
| B351 | | 486 |
| B352 | | 473 |

-continued

| Ex. No. | Product | Molecular weight |
|---|---|---|
| B353 | | 373 |
| B354 | | 434 |
| B355 | | 433 |
| B356 | | 451 |
| B357 | | 515 |

-continued
| Ex. No. | Product | Molecular weight |
|---|---|---|
| B358 | 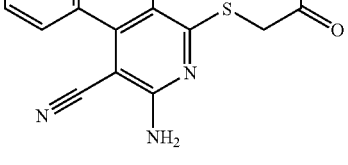 | 419 |
| B359 | 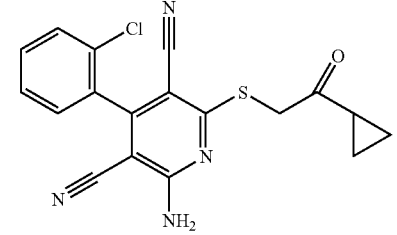 | 369 |
| B360 | 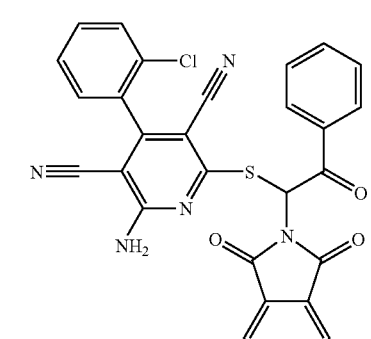 | 550 |
| B361 | 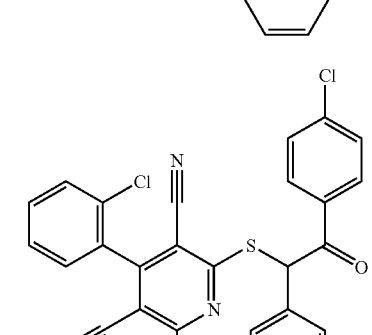 | 515 |
| B362 | 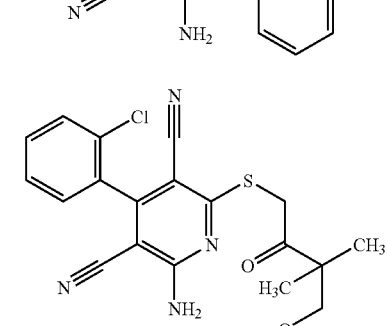 | 479 |

| Ex. No. | Product | Molecular weight |
|---|---|---|
| B363 | 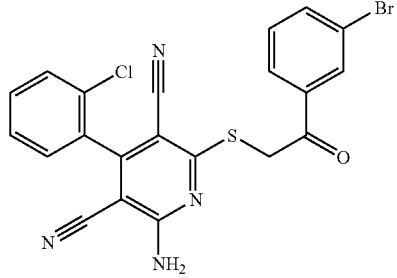 | 484 |
| B364 | 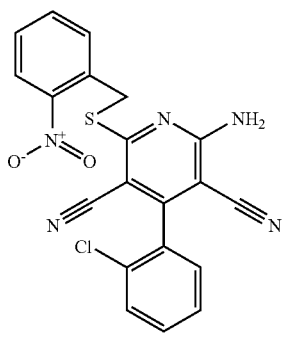 | 422 |
| B365 | 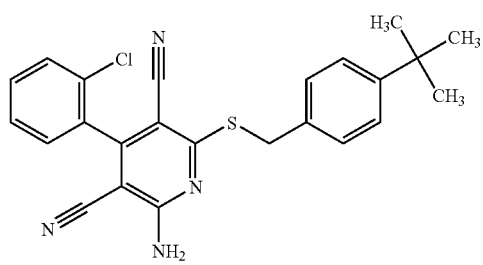 | 433 |
| B366 | 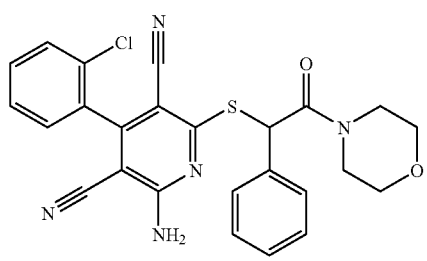 | 490 |
| B367 | 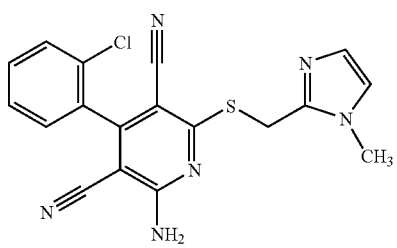 | 381 |

-continued

| Ex. No. | Product | Molecular weight |
|---|---|---|
| B368 | | 417 |
| B369 | | 396 |
| B370 | | 397 |
| B371 | | 460 |
| B372 | | 373 |
| B373 | | 415 |

| Ex. No. | Product | Molecular weight |
|---|---|---|
| | -continued | |
| B374 | 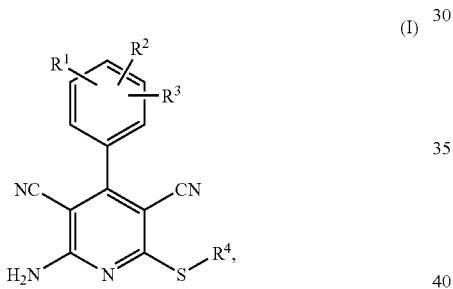 | 357 |
| B375 | | 414 |

The invention claimed is:

1. A compound of the formula (I)

$R^1$, $R^2$, $R^3$ are identical or different and independently of one another are selected from the group consisting of the following substituents:
hydrogen;
hydroxyl;
optionally substituted ($C_1$–$C_8$)-alkyl;
optionally substituted ($C_6$–$C_{10}$)-aryl;
optionally substituted ($C_1$–$C_8$)-alkoxy;
—O($CH_2$)$_n$—CH=$CH_2$ where n=0, 1 or 2;
halogen;
nitro;
cyano;
—C(O)—$R^5$;
—C(O)—$NR^6R^7$;
—$NR^6R^7$;
—$NR^6$—C(O)—$R^8$;
—O—C(O)—$R^8$;
—$SO_2$—$NR^6R^7$; and
—$NR^6$—$SO_2R^8$,
where:
$R^5$ denotes:
hydrogen;
hydroxyl;
optionally substituted ($C_1$–$C_8$)-alkyl;
optionally substituted ($C_3$–$C_7$)-cycloalkyl;
optionally substituted ($C_1$–$C_8$)-alkoxy;
optionally substituted ($C_6$–$C_{10}$)-aryl;
optionally substituted ($C_6$–$C_{10}$)-aryloxy; or
—O—($CH_2$)$_n$—[($C_6$–$C_{10}$)-aryl] where n=1, 2 or 3,
where the ($C_6$–$C_{10}$)-aryl group may be fused via two adjacent ring atoms to optionally substituted ($C_4$–$C_7$)-cycloalkyl,
or
$R^5$ represents a 5- to 7-membered saturated or unsaturated heterocycle which may be mono- or polysubstituted by
an oxo group (=O);
halogen;
optionally substituted ($C_1$–$C_8$)-alkyl;
nitro;
cyano;
hydroxyl;
optionally substituted ($C_6$–$C_{10}$)-aryl; or
by ($C_1$–$C_8$-alkoxy,
or
$R^5$ represents optionally substituted 5- to 6-membered heteroaryl having up to 3 heteroatoms from the group consisting of N, O and S,
where the heterocycle and the heteroaryl ring may each optionally be fused via two adjacent ring atoms to optionally substituted ($C_6$–$C_{10}$)-aryl or optionally substituted ($C_4$–$C_7$)-cycloalkyl,
and
$R^6$ and $R^7$ are identical or different and represent
hydrogen;
optionally substituted ($C_1$–$C_8$)-alkyl;
optionally substituted ($C_6$–$C_{10}$)-aryl; or
represent optionally substituted 5- to 6-membered heteroaryl having up to 3 heteroatoms from the group consisting of N, O and S
or
$R^6$ and $R^7$ together with the nitrogen atom to which they are optionally attached form a 5- to 7-membered saturated or unsaturated heterocycle having up to 3 heteroatoms from the group consisting of N, O and S, which may optionally be mono- or polysubstituted by identical or different substituents from the group consisting of
an oxo group (=O);
halogen;
$(C_1-C_8)$-alkyl;
cyano;
hydroxyl;
$(C_6-C_{10})$-aryl; and
$(C_1-C_8)$-alkoxy,
and
$R^8$ represents hydroxyl;
$NR^6R^7$ where $R^6$ and $R^7$ are as defined above;
optionally substituted $(C_1-C_8)$-alkyl;
$(C_1-C_8)$-alkoxy;
optionally substituted $(C_6-C_{10})$-aryl;
$(C_6-C_{10})$-aryloxy; or
—O—$(CH_2)_n$—[$(C_6-C_{10})$-aryl] where n=1, 2 or 3,
and
$R^4$ represents straight-chain or branched $(C_1-C_8)$-alkyl or $(C_2-C_8$alkenyl which are optionally mono- or polysubstituted by
optionally substituted $(C_6-C_{10})$-aryloxy;
optionally substituted 5- to 6-membered heteroaryl having up to 3 heteroatoms from the group consisting of N, O and S;
optionally substituted $(C_6-C_{10})$-aryl; or
by a 5- to 7-membered saturated or unsaturated heterocycle having up to 3 heteroatoms from the group consisting of N, O and S, which may optionally be mono- or polysubstituted by identical or different substituents from the group consisting of an oxo group (=O); halogen; $(C_1-C_8)$alkyl; nitro; cyano; hydroxyl; $(C_6-C_{10})$-aryl; and or by $(C_1-C_8)$-alkoxy,
where the heterocycle and the heteroaryl ring may each optionally be fused via two adjacent ring atoms to optionally substituted $(C_6-C_{10})$-aryl,
or a tautomer, salt, hydrate, or alkoxide thereof,
except for the following compounds of the formula (I), in which the radicals $R^1$, $R^2$, $R^3$ and $R^4$ are as defined below:
$R^1=R^2=H$; $R^3$=para-OH; $R^4$=—$CH_2$—Z where Z=CN, C(O)—$OC_2H_5$, 4-Br—$C_6H_4$—CO, 4-n-butyl-$C_6H_4$—CO, H, $C_6H_5$, C(O)—O—$CH_2$—$C_6H_5$, C(O)—$OCH_3$, C(O)—OH, 2-oxo-benzo-pyranyl-3-carbonyl, 4-Cl—$C_6H_4$—CO, 3-Br—$C_6H_4$—CO, 4-$C_6H_5$—$C_6H_4$—CO, 4-$CH_3$—$C_6H_4$—CO, 3,4-$Cl_2$—$C_6H_3$—CO, or C(O)—$NH_2$;
$R^1=R^2=H$; $R^3$=meta-OH; $R^4$=—$CH_2$—Z where Z=4-Br—$C_6H_4$—NH—CO, 2-oxo-benzo-pyranyl-3-carbonyl, 4-Cl—$C_6H_4$—CO;
$R^1=R^2=H$; $R^3$=para-O—C(O)—$CH_3$; $R^4$=—$CH_2$—Z where Z=4-$CH_3$—$C_6H_4$—CO, H, 2-oxo-benzopyranyl-3-carbonyl, $(CH_2)_3$—$CH_3$, 4-$C_6H_5$—$C_6H_4$, $(CH_2)_4$—$CH_3$, $CH_3$, or 2-$CH_3$—$C_6H_4$;
$R^1=R^2=R^3=H$; $R^4$=—$CH_2$—Z where Z=$CH_3$, CN, 2-naphthyl, 4-Br—$C_6H_4$—CO, C(O)—$OCH_3$, C(O)—$OCH_2$—$CH_5$, H, C(O)—$C_6H_5$, or 4-Cl—$C_6H_4$—CO;
$R^1=R^2=H$; $R^3$=para-butoxy; $R^4$=—$CH_2$—Z where Z=4-Cl—$C_6H_5$, C(O)—$OCH_3$, C(O)—$C_6H_5$, CH=$CH_2$, C(O)—$NH_2$, H, 4-Br—$C_6H_4$—CO, 4-Cl—$C_6H_4$—CO, C(O)—$OC_2H_5$, C(O)—O—$CH_2$—$C_6H_5$, 2-oxo-benzopyranyl-3-carbonyl, C(O)—NH—$C_6H_5$, CN;
$R^1=R^2=H$; $R^3$=para-bromo; $R^4$=—$CH_2$—Z where Z=4-Br—$C_6H_4$—CO, 4-Cl—$C_6H_4$—CO, C(O)—$NH_2$, C(O)—$OCH_3$, 4-Cl—$C_6H_5$, 4-Br—$C_6H_4$—NH—CO;
$R^1=R^2=H$; $R^3$=meta-fluoro; $R^4$=—$CH_2$—Z where Z=4-Br—$C_6H_4$—CO, C(O)—$NH_2$, C(O)—O—$CH_2$—$C_6H_5$, CN;
$R^1=R^2=H$; $R^3$=para-chloro; $R^4$=—$CH_2$—Z where Z=2-naphthyl, $CH_3$, 4-Cl—$C_6H_4$—CO, or $C_6H_5$—CO;
$R^1=R^2=H$; $R^3$=para-$OCH_3$; $R^4$=—$CH_2$—Z where Z=2-naphthyl, $CH_3$;
$R^1=R^2=H$; $R^3$=meta-$NO_2$; $R^4$=—$CH_2$—Z where Z=$CH_3$;
$R^1=R^2=H$; $R^3$=ortho-$OCH_3$; $R^4$=—$CH_2$—Z where Z=4-Cl—$C_6H_4$—CO;
$R^1=R^2=H$; $R^3$=ortho-chloro; $R^4$=—$CH_2$—Z where Z=4-Cl—$C_6H_4$—CO, $C_6H_5$—CO, or CH=$CH_2$;
$R^1=R^2=H$; $R^3$=ortho-iodo; $R^4$=—$CH_2$—Z where Z=CH=$CH_2$.

2. The compound of the formula (I) as claimed in claim 1, wherein:
$R^1$, $R^2$, $R^3$ are identical or different and independently of one another are selected from the group consisting of the following substituents:
hydrogen;
hydroxyl;
optionally substituted $(C_1-C_6)$-alkyl;
optionally substituted phenyl or naphthyl;
optionally substituted $(C_1-C_6)$-alkoxy;
—O—$(CH_2)_n$—CH=$CH_2$ where n=1 or 2;
fluorine, chlorine, bromine;
nitro;
cyano;
—C(O)—$R^5$;
—C(O)—$NR^6R^7$;
—$NR^6R^7$;
—$NR^6$—C(O)—$R^8$;
—O—C(O)—$R^8$;
—$SO_2$—$NR^6R^7$; and
—$NR^6$—$SO_2R^8$,
where:
$R^5$ denotes:
hydrogen;
hydroxyl;
optionally substituted $(C_1-C_6)$-alkyl;
optionally substituted $(C_3-C_7)$-cycloalkyl;
optionally substituted $(C_1-C_6)$-alkoxy;
optionally substituted phenyl or naphthyl;
optionally substituted phenyloxy or naphthyloxy; or
—O—$(CH_2)_n$-phenyl where n=1, 2 or 3,
where the phenyl or naphthyl group may be fused via two adjacent ring atoms to optionally substituted $(C_4-C_7)$-cycloalkyl,
or
$R^5$ represents a 5- to 7-membered saturated or unsaturated heterocycle which may be mono- or polysubstituted by
an oxo group (=O);
fluorine, chlorine, bromine;
optionally substituted $(C_1-C_6)$-alkyl;
nitro;
cyano;
hydroxyl;
optionally substituted phenyl or naphthyl; or
by $(C_1-C_6)$-alkoxy, or R⁵ represents optionally substituted 5- to 6-membered heteroaryl having up to 3 heteroatoms from the group consisting of N, O and S,
where the heterocycle and the heteroaryl ring may each optionally be fused via two adjacent ring atoms to optionally substituted phenyl or naphthyl or optionally substituted $(C_4-C_7)$-cycloalkyl, and R⁶ and R⁷ are identical or different and represent hydrogen;
optionally substituted $(C_1-C_6)$-alkyl;
optionally substituted phenyl or naphthyl; or
represent optionally substituted 5- to 6-membered heteroaryl having up to 3 heteroatoms from the group consisting of N, O and S or R⁶ and R⁷ together with the nitrogen atom to which they are optionally attached form a 5- to 7-membered saturated or unsaturated heterocycle having up to 3 heteroatoms from the group consisting of N, O and S, which may optionally be mono- or polysubstituted by identical or different substituents from the group consisting of
an oxo group (=O);
fluorine, chlorine, bromine;
$(C_1-C_6)$-alkyl;
nitro;
cyano;
hydroxyl;
phenyl or naphthyl; and
$(C_1-C_6)$-alkoxy, and R⁸ represents NR⁶R⁷ where R⁶ and R⁷ are as defined above;
optionally substituted $(C_1-C_6)$-alkyl;
$(C_1-C_6)$-alkoxy;
optionally substituted phenyl or naphthyl;
phenyloxy or naphthyloxy; or
—O—$(CH_2)_n$-phenyl where n=1, 2 or 3, and R⁴ represents straight chain or branched $(C_1-C_6)$-alkyl or $(C_2-C_6)$-alkenyl which are optionally mono- or polysubstituted by
optionally substituted phenyloxy or naphthyloxy;
optionally substituted 5- to 6-membered heteroaryl having up to 3 heteroatoms from the group consisting of N, O and S;
optionally substituted phenyl or naphthyl; or
by a 5- to 7-membered saturated or unsaturated heterocycle having up to 3 heteroatoms from the group consisting of N, O and S, which may optionally be mono- or polysubstituted by identical or different substituents from the group consisting of an oxo group (=O); fluorine, chlorine, bromine; $(C_1-C_6)$-alkyl; nitro; cyano; hydroxyl; phenyl or naphthyl; or by $(C_1-C_6)$-alkoxy,
where the heterocycle and the heteroaryl ring may each optionally be fused via two adjacent ring atoms to optionally substituted phenyl or naphthyl,
or a tautomer, salt, hydrate, or alkoxide thereof,
except for the following compounds of the formula (I), in which the radicals R¹, R², R³ and R⁴ are as defined below:

R¹=R²=H; R³=para-OH; R⁴=—CH₂—Z where Z=CN, C(O)—OC₂H₅, 4-Br—C₆H₄—CO, 4-n-butyl-C₆H₄—CO, H, C₆H₅, C(O)—O—CH₂—C₆H₅, C(O)—OCH₃, C(O)—OH, 2-oxo-benzopyranyl-3-carbonyl, 4-Cl—C₆H₄—CO, 3-Br—C₆H₄—CO, 4-C₆H₅—C₆H₄—CO, 4-CH₃—C₆H₄—CO, 3,4-Cl₂—C₆H₃—CO, C(O)—NH₂;

R¹=R²=H; R³=meta-OH; R⁴=—CH₂—Z where Z=4-Br—C₆H₄—NH—CO, 2-oxo-benzo-pyranyl-3-carbonyl, 4-Cl—C₆H₄—CO;

R¹=R²=H; R³=para-O—C(O)—CH₃; R⁴=—CH₂—Z where Z=4-CH₃—C₆H₄—CO, H, 2-oxo-benzopyranyl-3-carbonyl, (CH₂)₃—CH₃, 4-C₆H₅—C₆H₄, (CH₂)₄—CH₃, CH₃, 2-CH₃—C₆H₄;

R¹=R²=R³=H; R⁴=—CH₂—Z where Z=CH₃, CN, 2-naphthyl, 4-Br—C₆H₄—CO, C(O)—OCH₃, C(O)—OCH₂—C₆H₅, H, C(O)—C₆H₅, 4-Cl—C₆H₄—CO;

R¹=R²=H; R³=para-butoxy; R⁴=—CH₂—Z where Z=4-Cl—C₆H₅, C(O)—OCH₃, C(O)—C₆H₅, CH=CH₂, C(O)—NH₂, H, 4-Br—C₆H₄—CO, 4-Cl—C₆H₄—CO, C(O)—OC₃H₅, C(O)—O—CH₂—CH₅, 2-oxo-benzopyranyl-3-carbonyl, C(O)—NH—C₆H₅, CN;

R¹=R²=H; R³=para-bromo; R⁴=—CH₂—Z where Z=4-Br—C₆H₄—CO, 4-Cl—C₆H₄—CO, C(O)—NH₂, C(O)—OCH₃, 4-Cl—C₆H₅, 4-Br—C₆H₄—NH—CO;

R¹=R²=H; R³=meta-fluoro; R⁴=—CH₂—Z where Z=4-Br—C₆H₄—CO, C(O)—NH₂, C(O)—O—CH₂—C₆H₅, CN;

R¹=R²=H; R³=para-chloro; R⁴=—CH₂—Z where Z=2-naphthyl, CH₃, 4-Cl—C₆H₄—CO, C₆H₅—CO;

R¹=R²=H; R³=para-OCH₃; R⁴=—CH₂—Z where Z=2-naphthyl, CH₃;

R¹=R²H; R³=meta-NO₂; R⁴=—CH₂—Z where Z=CH₃;

R¹=R²=H; R³=ortho-OCH₃; R⁴=—CH₂—Z where Z=4-Cl—C₆H₄—CO;

R¹=R²=H; R³=ortho-chloro; R⁴=—CH₂—Z where Z=4-Cl—C₆H₄—CO, C₆H₅—CO, or CH=CH₂.

3. The compound of the formula (I) as claimed in claim 1, wherein:

R¹, R², R³ are identical or different and independently of one another are selected from the group consisting of the following substituents:
hydrogen;
hydroxyl;
optionally substituted $(C_1-C_4)$-alkyl;
optionally substituted phenyl;
optionally substituted $(C_1-C_4)$-alkoxy;
—O—$(CH_2)_n$—CH=CH₂ where n=1;
fluorine, chlorine;
nitro;
cyano;
—C(O)—R⁵;
—C(O)—NR⁶R⁷;
—N⁶R⁷;
—NR⁶—C(O)—R⁸;
—O—C(O)—R⁸;
—SO₂—NR⁶R⁷; and
where:
R⁵ denotes:
hydrogen;
hydroxyl;
optionally substituted $(C_1-C_4)$-alkyl;
optionally substituted $(C_3-C_7)$-cycloalkyl;

optionally substituted $(C_1–C_4)$-alkoxy;
optionally substituted phenyl;
optionally substituted phenyloxy; or
—O—$(CH_2)_n$-phenyl where n=1,
  where the phenyl group may be fused via two adjacent ring atoms to optionally substituted $(C_5–C_6)$-cycloalkyl,
or
$R^5$ represents a 5- to 7-membered saturated or unsaturated heterocycle which for its part may be mono- or polysubstituted by
an oxo group (=O);
fluorine, chlorine;
optionally substituted $(C_1–C_4)$-alkyl;
nitro;
cyano;
hydroxyl;
optionally substituted phenyl; or
by $(C_1–C_4)$-alkoxy,
or
$R^5$ represents optionally substituted 5- to 6-membered heteroaryl having up to 3 heteroatoms from the group consisting of N, O and S, selected from the group consisting of furanyl, pyrrolyl, thienyl, thiazolyl, oxazolyl, imidazolyl, triazolyl, pyridyl, pyrimidyl and pyridazinyl,
  where the heterocycle and the heteroaryl ring may each optionally be fused via two adjacent ring atoms to optionally substituted phenyl or optionally substituted $(C_5–C_6)$-cycloalkyl,
and
$R^6$ and $R^7$ are identical or different and represent
hydrogen;
optionally substituted $(C_1–C_4)$-alkyl;
optionally substituted phenyl; or
represent optionally substituted 5- to 6-membered heteroaryl having up to 3 heteroatoms from the group consisting of N, O and S selected from the group consisting of furanyl, pyrrolyl, thienyl, thiazolyl, oxazolyl, imidazolyl, triazolyl, pyridyl, pyrimidyl and pyridazinyl,
or
$R^6$ and $R^7$ together with the nitrogen atom to which they are optionally attached form a 5- to 7-membered saturated or unsaturated heterocycle having up to 3 heteroatoms from the group consisting of N, O and S, which may optionally be mono- or polysubstituted by identical or different substituents from the group consisting of
an oxo group (=O);
fluorine, chlorine;
$(C_1–C_4)$-alkyl;
nitro;
cyano;
hydroxyl;
phenyl; and
$(C_1–C_4)$-alkoxy,
and
$R^8$ represents $NR^6R^7$ where $R^6$ and $R^7$ are as defined above;
optionally substituted $(C_1–C_4)$-alkyl;
$(C_1–C_4)$-alkoxy;
optionally substituted phenyl;
phenyloxy; or
—O—$(CH_2)_n$-phenyl where n=1,
and
$R^4$ represents straight-chain or branched $(C_1–C_4)$-alkyl or $(C_2–C_4)$-alkenyl which are optionally mono- or polysubstituted by
optionally substituted phenyloxy;
optionally substituted 5- to 6-membered heteroaryl having up to 3 heteroatoms from the group consisting of N, O and S selected from the group consisting of furanyl, pyrrolyl, thienyl, thiazolyl, oxazolyl, imidazolyl, triazolyl, pyridyl pyrimidyl and pyridazinyl;
optionally substituted phenyl; or
by a 5- to 7-membered saturated or unsaturated heterocycle having up to 3 heteroatoms from the group consisting of N, O and S, which may optionally be mono- or polysubstituted by identical or different substituents from the group consisting of an oxo group (=O); fluorine, chlorine; $(C_1–C_4)$-alkyl; nitro; cyano; hydroxyl; phenyl; or by $(C_1–C_4)$-alkoxy,
  where the heterocycle and the heteroaryl ring may each optionally be fused via two adjacent rings atoms to optionally substituted phenyl,
or a tautomer, salt, hydrate, or alkoxide thereof,
except for the following compounds of the formula (I), in which the radicals $R^1$, $R^2$, $R^3$ and $R^4$ are as defined below:
$R^1=R^2=H$; $R^3$=para-OH; $R^4=$—$CH_2$—Z where Z=CN, C(O)—$OC_2H_5$, 4-Br—$C_6H_4$—CO, 4-n-butyl-$C_6H_4$—CO, H, $C_6H_5$, C(O)—O—$CH_2$—$C_6H_5$, C(O)—$OCH_3$, C(O)—OH, 2-oxo-benzo-pyranyl-3-carbonyl, 4-Cl—$C_6H_4$—CO, 3-Br—$C_6H_4$—CO, 4-$C_6H_5$—$C_6H_4$—CO, 4-$CH_3$—$C_6H_4$—CO, 3,4-$Cl_2$—$C_6H_3$—CO, or C(O)—$NH_2$;
$R^1=R^2=H$; $R^3$=meta-OH; $R^4=$—$CH_2$—Z where Z=4-Br—$C_6H_4$—NH—CO, 2-oxo-benzo-pyranyl-3-carbonyl, 4-Cl—$C_6H_4$—CO;
$R^1=R^2=H$; $R^3$=para-O—C(O)—$CH_3$; $R^4=$—$CH_2$—Z where Z=4-$CH_3$—$C_6H_4$—CO, H, 2-oxo-benzopyranyl-3-carbonyl, 4-$C_6H_5$—$C_6H_4$, $CH_3$, 2-$CH_3$—$C_6H_4$;
$R^1=R^2=R^3=H$; $R^4=$—$CH_2$—Z where Z=$CH_3$, CN, 4-Br—$C_6H_4$—CO, C(O)—$OCH_3$, C(O)—$OCH_2$—$C_6H_5$, H, C(O)—$C_6H_5$, 4-Cl—$C_6H_4$—CO;
$R^1=R^2=H$; $R^3$=para-butoxy; $R^4=$—$CH_2$—Z where Z=4-Cl—$C_6H_5$, C(O)—$OCH_3$, C(O)—$C_6H_5$, CH=$CH_2$, C(O)—$NH_2$, H, 4-Br—$C_6H_4$—CO, 4-Cl—$C_6H_4$—CO, C(O) —$OC_2H_5$, C(O)—O—$CH_2$—$C_6H_5$, 2-oxo-benzopyranyl-3-carbonyl, C(O)—NH—$C_6H_5$, CN;
$R^1=R^2=H$; $R^3$=meta-fluoro; $R^4=$—$CH_2$—Z where Z=4-Br—$C_6H_4$—CO, C(O)—$NH_2$, C(O)—O—$CH_2$—$C_6H_5$, CN;
$R^1=R^2=H$; $R^3$ para-chloro; $R^4=$—$CH_2$—Z where Z=$CH_3$, 4-Cl—$C_6H_4$—CO, or $C_6H_5$—CO;
$R^1=R^2=H$; $R^3$=para-$OCH_3$; $R^4=$—$CH_2$—Z where Z=$CH_3$;
$R^1=R^2=H$; $R^3$=meta-$NO_2$; $R^4=$—$CH_2$—Z where Z=$CH_3$;
$R^1=R^2=H$; $R^3$=ortho-$OCH_3$; $R^4=$—$CH_2$—Z where Z=4-Cl—$C_6H_4$—CO;
$R^1=R^2=H$; $R^3$=ortho-chloro; $R^4=$—$CH_2$—Z where Z=4-Cl—$C_6H_4$—CO, $C_6H_5$—CO, or CH=$CH_2$.

4. The compound of the formula (I) as claimed in any of claims 1 to 3, wherein
$R^1$, $R^2$, $R^3$ are identical or different and independently of one another are selected from the group consisting of the following substituents:

hydrogen;
hydroxyl;
methyl;
trifluoromethyl;
methoxy;
radicals of the formulae —O—CH$_2$—CH$_2$—OH, —O—CH$_2$—COOH or —O—CH$_2$—CH=CH$_2$;
fluorine, chlorine or bromine;
nitro;
cyano;
—C(O)OH or C(O)OCH$_3$;
—C(O)NH$_2$;
—NH$_2$;
—NH—C(O)—CH$_3$;
—O—C(O)—CH$_3$ or —O—C(O)—C$_2$H$_5$;
radicals of the formulae

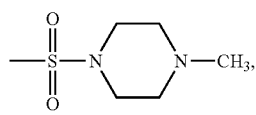

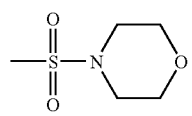

or

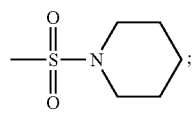

and
—NH—SO$_2$CH$_3$ or —NH—SO$_2$C$_6$H$_5$,
and
R$^4$ represents straight-chain or branched (C$_1$–C$_4$)-alkyl which is optionally mono- or polysubstituted by
  phenyl, which may be substituted by nitro, cyano, fluorine, methoxy, difluoromethoxy, methoxycarbonyl or p-tolylsulfonylmethyl;
  pyridyl, furyl, imidazolyl, benzimidazolyl or thiazolyl, which may in each case be mono- or disubstituted by identical or different substituents from the group consisting of methyl, nitro and chlorine;
  oxadiazolyl which may be substituted by phenyl or methoxyphenyl;
  or
  a radical of the formula

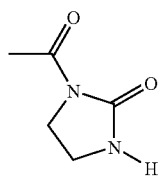

or a tautomer, salt, hydrate, or alkoxide thereof,
except for the following compounds of the formula (I), in which the radicals R$^1$, R$^2$, R$^3$ and R$^4$ are as defined below:
  R$^1$=R$^2$=H;  R$^3$=para-H;  R$^4$=—CH$_2$—Z where Z=H, C$_6$H$_5$, C(O)—OCH$_3$, or C(O)—NH$_2$;

R$^1$=R$^2$=H;  R$^3$=para-O—C(O)—CH$_3$;  R$^4$=—CH$_2$—Z where Z=H, or CH$_3$;
R$^1$=R$^2$=R$^3$=H; R$^4$=—CH$_2$—Z where Z=CH$_3$, or C(O)—OCH$_3$;
R$^1$=R$^2$=H; R$^3$=meta-fluoro; R$^4$=—CH$_2$—Z where Z=C(O)—NH$_2$;
R$^1$=R$^2$=H; R$^3$=para-chloro; R$^4$=—CH$_2$—Z where Z=CH$_3$;
R$^1$=R$^2$=H; R$^3$=para-OCH$_3$; R$^4$=—CH$_2$—Z where Z=CH$_3$;
R$^1$=R$^2$=H; R$^3$=meta-NO$_2$; R$^4$=—CH$_2$—Z where Z=CH$_3$.

5. The compound of the formula (I) as claimed in any of claims 1 to 3, wherein
  R$^1$, R$^2$, R$^3$ are identical or different and independently of one another are selected from the group consisting of the following substituents:
  hydrogen;
  hydroxyl;
  methyl;
  methoxy;
  radicals of the formulae —O—CH$_2$—CH$_2$—OH, —O—CH$_2$—COOH or —O—CH$_2$CH=CH$_2$;
  fluorine or chlorine;
  nitro;
  cyano;
  —C(O)OH or —C(O)OCH$_3$;
  —C(O)NH$_2$;
  —NH$_2$;
  —NH—C(O)CH$_3$;
  —O—C(O)—CH$_3$ or —O—C(O)—C$_2$H$_5$;
  radicals of the formulae

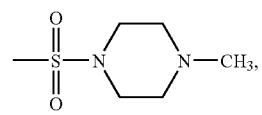

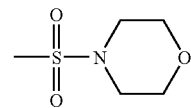

or

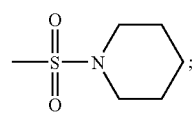

and
—NH—SO$_2$CH$_3$ or —NH—SO$_2$C$_6$H$_5$,
and
R$^4$ represents straight-chain or branched (C$_1$–C$_4$)-alkyl which is optionally mono- or polysubstituted by
  phenyl;
  ortho-nitrophenyl; or a radical of the formula

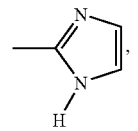

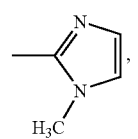

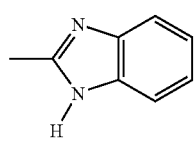

or

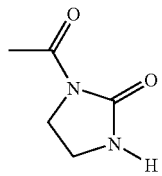

or a tautomer, salt, hydrate, or alkoxide thereof,
except for the following compounds of the formula (I), in which the radicals $R^1$, $R^2$, $R^3$ and $R^4$ are as defined below:
$R^1=R^2=H$; $R^3$=para-OH; $R^4=$—$CH_2$—Z where Z=H, $C_6H_5$, C(O)—$OCH_3$, or C(O)—$NH_2$;
$R^1=R^2=H$; $R^3$=para-O—C(O)—$CH_3$; $R^4=$—$CH_2$—Z where Z=H, or $CH_3$;
$R^1=R^2=R^3=H$; $R^4=$—$CH_2$—Z where Z=$CH_3$, or C(O)—$OCH_3$;
$R^1=R^2=H$; $R^3$=meta-fluoro; $R^4=$—$CH_2$—Z where Z=C(O)—$NH_2$;
$R^1=R^2=H$; $R^3$=para-chloro; $R^4=$—$CH_2$—Z where Z=$CH_3$;
$R^1=R^2H$; $R^3$=para-$OCH_3$; $R^4=$—$CH_2$—Z where Z=$CH_3$;
$R^1=R^2=H$; $R^3$=meta-$NO_2$; $R^4=$—$CH_2$—Z where Z=$CH_3$.

6. A process for preparing the compounds of the formula (I) as claimed in claim 1,
wherein:
a compound of the formula (II)

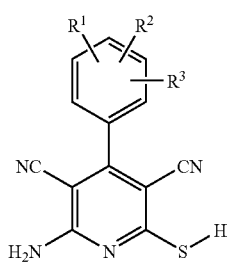
(II)

in which the radicals $R^1$, $R^2$ and $R^3$ are as defined above in claim 1,
is reacted with a compound of the formula (III)

$$R^4—X \quad \quad (III),$$

in which $R^4$ is as defined above in claim 1
and
X represents a nucleofugic group,
in an inert solvent, if appropriate in the presence of a base.

7. The process of claim 6 wherein said nucleofugic group is selected from the group consisting of halogen, mesylate, tosylate, triflate, and 1-imidazolyl.

8. The process of claim 7 wherein said halogen is selected from the group consisting of chlorine, bromine, and iodine.

9. A method of treating a cardiovascular disorder comprising administering to a host in need thereof an effective amount of a compound of the formula (I)

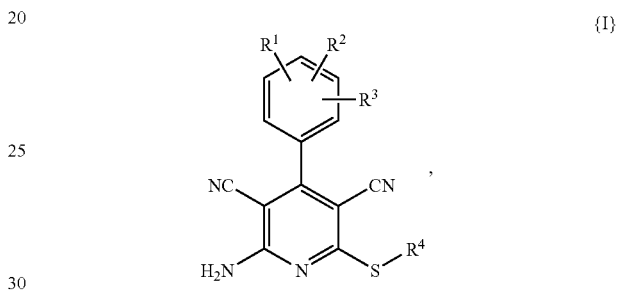
(I)

wherein:
$R^1$, $R^2$, $R^3$ are identical or different and independently of one another are selected from the group consisting of the following substituents:
hydrogen;
hydroxyl;
optionally substituted ($C_1$-$C_8$)-alkyl;
optionally substituted ($C_6$-$C_{10}$)-aryl;
optionally substituted ($C_1$-$C_8$)-alkoxy;
—O—$(CH_2)_n$—CH=$CH_2$ where n=0, 1 or 2;
halogen;
nitro;
cyano;
—C(O)—$R^5$;
—C(O)—$NR^6R^7$;
—$NR^6R^7$;
—$NR^6$—C(O)—$R^8$;
—O—C(O)—$R^8$;
—$SO_2$—$NR^6R^7$; and
—$NR^6$—$SO_2R^8$,
where:
$R^5$ denotes:
hydrogen;
hydroxyl;
optionally substituted ($C_1$-$C_8$)-alkyl;
optionally substituted ($C_3$-$C_7$)-cycloalkyl;
optionally substituted ($C_1$-$C_8$)-alkoxy;
optionally substituted ($C_6$-$C_{10}$)-aryl;
optionally substituted ($C_6$-$C_{10}$)-aryloxy; or
—O—$(CH_2)_n$—[($C_6$-$C_{10}$)-aryl] where n=1, 2 or 3,
where the ($C_6$-$C_{10}$)-aryl group may be fused via two adjacent ring atoms to optionally substituted ($C_4$-$C_7$)-cycloalkyl, or $R^5$ represents a 5- to 7-membered saturated or unsaturated heterocycle which may be mono- or polysubstituted by
an oxo group (=O);
halogen;
optionally substituted $(C_1–C_8)$-alkyl:
nitro;
cyano;
hydroxyl;
optionally substituted $(C_6–C_{10})$-aryl; or
by $(C_1–C_8)$-alkoxy, or $R^5$ represents optionally substituted 5- to 6-membered heteroaryl having up to 3 heteroatoms from the group consisting of N, O and S,
where the heterocycle and the heteroaryl ring may each optionally be fused via two adjacent ring atoms to optionally substituted $(C_6–C_{10})$-aryl or optionally substituted $(C_4–C_7)$-cycloalkyl, and $R^6$ and $R^7$ are identical or different and represent
hydrogen;
optionally substituted $(C_1–C_8)$-alkyl;
optionally substituted $(C_6–C_{10})$-aryl; or
represent optionally substituted 5- to 6-membered heteroaryl having up to 3 heteroatoms from the group consisting of N, O and S or $R^6$ and $R^7$ together with the nitrogen atom to which they are optionally attached form a 5- to 7-membered saturated or unsaturated heterocycle having up to 3 heteroatoms from the group consisting of N, O and S, which may optionally be mono- or polysubstituted by identical or different substituents from the group consisting of
an oxo group (=O);
halogen;
$(C_1–C_8)$-alkyl;
nitro;
cyano;
hydroxyl;
$(C_6–C_{10})$-alkyl; and
$(C_1–C_8)$-alkoxy, and $R^8$ represents hydroxyl;
$NR^6R^7$ where $R^6$ and $R^7$ are as defined above;
optionally substituted $(C_1–C_8)$-alkyl;
$(C_1–C_8)$-alkoxy;
optionally substituted $(C_6–C_{10})$-aryl;
$(C_6–C_{10})$-aryloxy; or
—O—$(CH_2)_n$—[$(C_6–C_{10})$-aryl] where n=1, 2 or 3, and $R^4$ represents straight-chain or branched $(C_1–C_8)$-alkyl or $(C_2–C_8)$-alkenyl which are optionally mono- or polysubstituted by
optionally substituted $(C_6–C_{10})$-aryloxy;
optionally substituted 5- to 6-membered heteroaryl having up to 3 heteroatoms from the group consisting of N, O and S;
optionally substituted $(C_6–C_{10})$-aryl; or
by a 5- to 7-membered saturated or unsaturated heterocycle having up to 3 heteroatoms from the group consisting of N, O and S, which may optionally be mono- or polysubstituted by identical or different substituents from the group consisting of an oxo group (=O); halogen; $(C_1–C_8)$-alkyl; nitro; cyano: hydroxyl; $(C_6–C_{10})$-aryl; or by $(C_1–C_8)$-alkoxy,
where the heterocycle and the heteroaryl ring may each optionally be fused via two adjacent ring atoms to optionally substituted $(C_6–C_{10})$-aryl, or a tautomer, salt, hydrate, or alkoxide thereof.

10. A method of treating a cardiovascular disorder comprising administering to a host in need thereof an effective amount of the compound of the formula (I) as claimed in claim 9,
wherein:
$R^1$, $R^2$, $R^3$ are identical or different and independently of one another are selected from the group consisting of the following substituents:
hydrogen;
hydroxyl;
optionally substituted $(C_1–C_6)$-alkyl;
optionally substituted phenyl or naphthyl;
optionally substituted $(C_1–C_6)$-alkoxy;
—O—$(CH_2)_n$—CH=$CH_2$ where n=1 or 2;
fluorine, chlorine, bromine;
nitro;
cyano;
—C(O)—$R^5$;
—C(O)—$NR^6R^7$;
—$NR^6R^7$;
—$NR^6$—C(O)—$R^8$;
—O—C(O)—$R^8$;
—$SO_2$—$NR^6R^7$; and
—$NR^6$—$SO_2R^8$,
where:
$R^5$ denotes:
hydrogen;
hydroxyl;
optionally substituted $(C_1–C_6)$-alkyl;
optionally substituted $(C_3–C_7)$-cycloalkyl;
optionally substituted $(C_1–C_6)$-alkoxy;
optionally substituted phenyl or naphthyl;
optionally substituted phenyloxy or naphthyloxy; or
—O—$(CH_2)_n$-phenyl where n=1, 2 or 3,
where the phenyl or naphthyl group may be fused via two adjacent ring atoms to optionally substituted $(C_4–C_7)$-cycloalkyl, or $R^5$ represents a 5- to 7-membered saturated or unsaturated heterocycle which may be mono- or polysubstituted by
an oxo group (=O);
fluorine, chlorine, bromine;
optionally substituted $(C_1–C_6)$-alkyl;
nitro;
cyano;
hydroxyl;
optionally substituted phenyl or naphthyl; or
by $(C_1–C_6)$-alkoxy, or $R^5$ represents optionally substituted 5- to 6-membered heteroaryl having up to 3 heteroatoms from the group consisting of N, O and S,
where the heterocycle and the heteroaryl ring may each optionally be fused via two adjacent ring atoms to optionally substituted phenyl or naphthyl or optionally substituted $(C_4–C_7)$-cycloalkyl, and $R^6$ and $R^7$ are identical or different and represent
hydrogen;
optionally substituted $(C_1–C_6)$-alkyl;

optionally substituted phenyl or naphthyl; or
represent optionally substituted 5- to 6-membered heteroaryl having up to 3 heteroatoms from the group consisting of N, O and S
or
$R^6$ and $R^7$ together with the nitrogen atom to which they are optionally attached form a 5- to 7-membered saturated or unsaturated heterocycle having up to 3 heteroatoms from the group consisting of N, O and S, which may optionally be mono- or polysubstituted by identical or different substituents from the group consisting of
an oxo group (=O);
fluorine, chlorine, bromine;
$(C_1-C_6)$-alkyl;
nitro;
cyano;
hydroxyl;
phenyl or naphthyl; and
$(C_1-C_6)$-alkoxy,
and
$R^8$ represents $NR^6R^7$ where $R^6$ and $R^7$ are as defined above;
optionally substituted $(C_1-C_6)$-alkyl;
$(C_1-C_6)$-alkoxy;
optionally substituted phenyl or naphthyl;
phenyloxy or naphthyloxy; or
—O—$(CH_2)_n$-phenyl where n=1, 2 or 3,
and
$R^4$ represents straight-chain or branched $(C_1-C_6)$-alkyl or $(C_2-C_6)$-alkenyl which are optionally mono- or polysubstituted by
optionally substituted phenyloxy or naphthyloxy;
optionally substituted 5- to 6-membered heteroaryl having up to 3 heteroatoms from the group consisting of N, O and S;
optionally substituted phenyl or naphthyl; or
by a 5- to 7-membered saturated or unsaturated heterocycle having up to 3 heteroatoms from the group consisting of N, O and S, which may optionally be mono- or polysubstituted by identical or different substituents from the group consisting of an oxo group (=O); fluorine, chlorine, bromine; $(C_1-C_6)$-alkyl; nitro; cyano; hydroxyl; phenyl or naphthyl; or by $(C_1-C_6)$-alkoxy,
where the heterocycle and the heteroaryl ring may each optionally be fused via two adjacent ring atoms to optionally substituted phenyl or naphthyl,
or a tautomer, salt, hydrate, or alkoxide thereof.

11. A method of treating cardiovascular disorder comprising administering to a host in need thereof an effective amount of the compound of the formula (I) as claimed in claim 10,
wherein:
$R^1$, $R^2$, $R^3$ are identical or different and independently of one another are selected from the group consisting of the following substituents:
hydrogen;
hydroxyl;
optionally substituted $(C_1-C_4)$-alkyl;
optionally substituted phenyl;
optionally substituted $(C_1-C_4)$-alkoxy;
—O—$(CH_2)_n$—CH=$CH_2$ where n=1;
fluorine, chlorine;
nitro;
cyano;
—C(O)—$R^5$;
—C(O)—$NR^6R^7$;
—$NR^6R^7$;
—$NR^6$—C(O)—$R^8$;
—O—(O)—$R^8$;
—$SO_2$—$NR^6R^7$; and
—$NR^6$—$SO_2R^8$,
where:
$R^5$ denotes:
hydrogen;
hydroxyl;
optionally substituted $(C_1-C_4)$-alkyl;
optionally substituted $(C_3-C_7)$-cycloalkyl;
optionally substituted $(C_1-C_4)$-alkoxy;
optionally substituted phenyl;
optionally substituted phenyloxy; or
—O—$(CH_2)_n$-phenyl where n=1,
where the phenyl group may be fused via two adjacent ring atoms to optionally substituted $(C_5-C_6)$-cycloalkyl,
or
$R^5$ represents a 5- to 7-membered saturated or unsaturated heterocycle which may be mono- or polysubstituted by
an oxo group (=O);
fluorine, chlorine;
optionally substituted $(C_1-C_4$alkyl;
nitro;
cyano;
hydroxyl;
optionally substituted phenyl; or
by $(C_1-C_4)$-alkoxy,
or
$R^5$ represents optionally substituted 5- to 6-membered heteroaryl having up to 3 heteroatoms from the group consisting of N, O and S, selected from the group consisting of furanyl, pyrrolyl, thienyl, thiazolyl, oxazolyl, imidazolyl triazolyl, pyridyl, pyrimidyl and pyridazinyl,
where the heterocycle and the heteroaryl ring may each optionally be fused via two adjacent ring atoms to optionally substituted phenyl or optionally substituted $(C_5-C_6)$-cycloalkyl,
and
$R^6$ and $R^7$ are identical or different and represent
hydrogen;
optionally substituted $(C_1-C_4)$-alkyl;
optionally substituted phenyl; or
represent optionally substituted 5- to 6-membered heteroaryl having up to 3 heteroatoms from the group consisting of N, O and S selected from the group consisting of furanyl, pyrrolyl, thienyl thiazolyl, oxazolyl, imidazolyl, triazolyl, pyridyl, pyrimidyl and pyridazinyl,
or
$R^6$ and $R^7$ together with the nitrogen atom to which they are optionally attached form a 5- to 7-membered saturated or unsaturated heterocycle having up to 3 heteroatoms from the group consisting of N, O and S, which may optionally be mono- or polysubstituted by identical or different substituents from the group consisting of
an oxo group (=O);
fluorine, chlorine;
$(C_1-C_4)$-alkyl;
nitro;
cyano;
hydroxyl;

phenyl; and
(C$_1$–C$_4$)-alkoxy,
and
R$^8$ represents NR$^6$R$^7$ where R$^6$ and R$^7$ are as defined above;
optionally substituted (C$_1$–C$_4$)-alkyl;
(C$_1$–C$_4$)-alkoxy;
optionally substituted phenyl;
phenyloxy; or
—O—(CH$_2$)$_n$-phenyl where n=1,
and
R$^4$ represents straight-chain or branched (C$_1$–C$_4$)-alkyl or (C$_2$–C$_4$)-alkenyl which are optionally mono- or polysubstituted by
optionally substituted phenyloxy;
optionally substituted 5- to 6-membered heteroaryl having up to 3 heteroatoms from the group consisting of N, O and S selected from the group consisting of furanyl, pyrrolyl, thienyl, thiazolyl, oxazolyl, imidazolyl, triazolyl, pyridyl, pyrimidyl and pyridazinyl;
optionally substituted phenyl; or
by a 5- to 7-membered saturated or unsaturated heterocycle having up to 3 heteroatoms from the group consisting of N, O and S, which may optionally be mono- or polysubstituted by identical or different substituents from the group consisting of an oxo group (=O); fluorine, chlorine; (C$_1$–C$_4$)-alkyl; nitro; cyano; hydroxyl; phenyl; or by (C$_1$–C$_4$)-alkoxy,
where the heterocycle and the heteroaryl ring may each optionally be fused via two adjacent rings atoms to optionally substituted phenyl,
or a tautomer, salt, hydrate, or alkoxide thereof.

12. A method of treating a cardiovascular disorder comprising administering to a host in need thereof an effective amount of the compound of the formula (I) as claimed in claim 11, wherein:
R$^1$, R$^2$, R$^3$ are identical or different and independently of one another are selected from the group consisting of the following substituents:
hydrogen;
hydroxyl;
methyl;
trifluoromethyl;
methoxy;
radicals of the formulae —O—CH$_2$—CH$_2$—OH, —O—CH$_2$—COOH or —O—CH$_2$—CH=CH$_2$;
fluorine, chlorine or bromine;
nitro;
cyano;
—C(O)OH or —C(O)OCH$_3$;
—C(O)NH$_2$;
—NH$_2$;
—NH—C(O)—CH$_3$;
—O—C(O)—CH$_3$ or —O—C(O)—C$_2$H$_5$;
radicals of the formulae

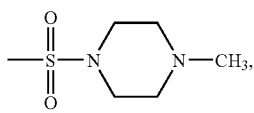

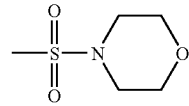

or

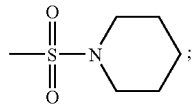

and
—NH—SO$_2$CH$_3$ or —NH—SO$_2$C$_6$H$_5$,
and
R$^4$ represents straight-chain or branched (C$_1$–C$_4$)-alkyl which is optionally mono- or polysubstituted by
phenyl, which may be substituted by nitro, cyano, fluorine, methoxy, difluoromethoxy, methoxycarbonyl or p-tolylsulfonylmethyl;
pyridyl, furyl, imidazolyl, benzimidazolyl or thiazolyl, which may in each case be mono- or disubstituted by identical or different substituents from the group consisting of methyl, nitro and chlorine;
oxadiazolyl which may be substituted by phenyl or methoxyphenyl;
or
a radical of the formula

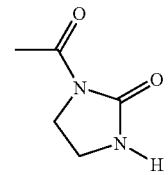

or a tautomer, salt, hydrate, or alkoxide thereof.

13. A method of treating a cardiovascular disorder comprising administering to a host in need thereof an effective amount of the compound of the formula (I) as claimed in claim 12, wherein:
R$^1$, R$^2$, R$^3$ are identical or different and independently of one another are selected from the group consisting of the following substituents:
hydrogen;
hydroxyl;
methyl;
methoxy;
radicals of the formulae —O—CH$_2$—CH$_2$—OH, —O—CH$_2$—COOH or —CH$_2$—CH=CH$_2$;
fluorine or chlorine;
nitro;
cyano;
—C(O)OH or —C(O)OCH$_3$;
—C(O)NH$_2$;
—NH$_2$;
—NH—C(O)CH$_3$;
—O—C(O)—CH$_3$ or —O—C(O)—C$_2$H$_5$;

radicals of the formulae

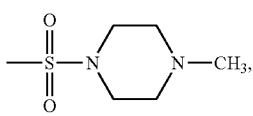

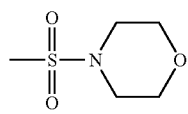

or

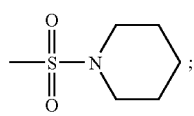

and
—NH—SO$_2$CH$_3$ or —NH—SO$_2$C$_6$H$_5$,
and
R$^4$ represents straight-chain or branched (C$_1$–C$_4$)-alkyl which is optionally mono- or polysubstituted by
phenyl;
ortho-nitrophenyl; or
a radical of the formula

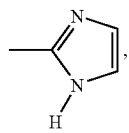

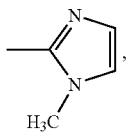

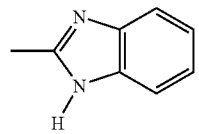

or

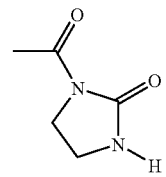

or a tautomer, salt, hydrate, or alkoxide thereof.

14. A pharmaceutical composition, comprising at least one compound of the formula (I) as defined in claim 1 plus a pharmaceutically acceptable carrier or excipient.

15. A pharmaceutical composition, comprising at least one selective adenosine receptor ligand of claim 1 selected from the group consisting of an adenosine A1 receptor ligand, adenosine A2a receptor ligand and adenosine A2b receptor ligand, plus a pharmaceutically acceptable carrier or excipient.

16. A method of treating a cardiovascular disorder comprising administering to a host in need thereof an effective amount of a pharmaceutical composition as claimed in claim 14 or 15.

17. A method of treating a cardiovascular disorder comprising administering to a host in need thereof an effective amount of a selective adenosine receptor ligand of claim 1 selected from the group consisting of adenosine A1 receptor ligand, adenosine A2a receptor ligand, and adenosine A2b receptor ligand.

* * * * *